United States Patent
Rothberg et al.

(10) Patent No.: US 6,231,812 B1
(45) Date of Patent: *May 15, 2001

(54) METHOD AND APPARATUS FOR INDENTIFYING, CLASSIFYING, OR QUANTIFYING PROTEIN SEQUENCES IN A SAMPLE WITHOUT SEQUENCING

(75) Inventors: Jonathan Marc Rothberg, Branford, CT (US); Michael W. Deem, Cambridge, MA (US); John W. Simpson, Madison, CT (US)

(73) Assignee: CuraGen Corporation, New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/322,617

(22) Filed: May 28, 1999

Related U.S. Application Data

(60) Continuation of application No. 08/942,406, filed on Oct. 1, 1997, which is a division of application No. 08/547,214, filed on Oct. 24, 1995, now Pat. No. 5,871,697.

(51) Int. Cl.[7] .................................................. G01N 15/06
(52) U.S. Cl. ................................ 422/68.1; 435/5; 435/6; 707/6; 702/19
(58) Field of Search .............................. 707/6; 422/68.1; 435/5, 6; 702/19

(56) References Cited

U.S. PATENT DOCUMENTS

| 4,555,019 | 11/1985 | Spendel et al. ....................... 206/223 |
| 4,987,066 | 1/1991 | Epplen ..................................... 435/6 |

(List continued on next page.)

FOREIGN PATENT DOCUMENTS

| 0 392 546 A3 | 10/1990 | (EP) . |
| 0 534 858 A1 | 3/1993 | (EP) . |
| 0 645 169 A1 | 3/1995 | (EP) . |
| WO 93/06239 | 4/1993 | (WO) . |
| WO 93/24655 | 12/1993 | (WO) . |
| WO 95/13369 | 5/1995 | (WO) . |
| WO 95/20681 | 8/1995 | (WO) . |
| WO 95/21944 | 8/1995 | (WO) . |
| WO 97/05286 | 2/1997 | (WO) . |
| WO 97/10363 | 3/1997 | (WO) . |

OTHER PUBLICATIONS

Adams et al., 1991, Science 252:1651–11656.
Adams et al., 1992, Nature 355:632–634.

(List continued on next page.)

*Primary Examiner*—Jack Choules
(74) *Attorney, Agent, or Firm*—Pennie & Edmonds LLP

(57) ABSTRACT

This invention provides methods by which biologically derived DNA sequences in a mixed sample or in an arrayed single sequence clone can be determined and classified without sequencing. The methods make use of information on the presence of carefully chosen target subsequences, typically of length from 4 to 8 base pairs, and preferably the length between target subsequences in a sample DNA sequence together with DNA sequence databases containing lists of sequences likely to be present in the sample to determine a sample sequence. The preferred method uses restriction endonucleases to recognize target subsequences and cut the sample sequence. Then carefully chosen recognition moieties are ligated to the cut fragments, the fragments amplified, and the experimental observation made. Polymerase chain reaction (PCR) is the preferred method of amplification. Another embodiment of the invention uses information on the presence or absence of carefully chosen target subsequences in a single sequence clone together with DNA sequence databases to determine the clone sequence. Computer implemented methods are provided to analyze the experimental results and to determine the sample sequences in question and to carefully choose target subsequences in order that experiments yield a maximum amount of information.

39 Claims, 23 Drawing Sheets

U.S. PATENT DOCUMENTS

| | | | |
|---|---|---|---|
| 5,093,245 | 3/1992 | Keith et al. | 435/91.2 |
| 5,171,534 | 12/1992 | Smith et al. | 94/1 |
| 5,175,082 | 12/1992 | Jeffreys | 435/6 |
| 5,202,231 | 4/1993 | Drmanac et al. | 501/1 |
| 5,262,311 | 11/1993 | Pardee et al. | 435/91.2 |
| 5,366,877 | 11/1994 | Keith et al. | 435/91.2 |
| 5,459,037 | 10/1995 | Sutcliffe et al. | 435/6 |
| 5,523,208 | 6/1996 | Kohler | 435/6 |
| 5,604,100 | 2/1997 | Perlin et al. | 435/6 |
| 5,632,041 | 5/1997 | Peterson et al. | 712/16 |
| 5,706,498 | 1/1998 | Fujimiya et al. | 707/6 |
| 5,733,729 | 3/1998 | Lipshutz et al. | 435/6 |
| 5,871,697 | 2/1999 | Rothberg et al. | 422/68.1 |
| 5,972,693 | 10/1999 | Rothberg et al. | 435/287.2 |

OTHER PUBLICATIONS

AFLP Analysis System I AFLP Starter Primer Kit, Instruction Manual, Life Technology.
Anon, 1995, Nature Medicine 1(2):102.
Ayala et al., 1995, BioTechniques 18(5):842–850.
Bassam et al., 1991, Anal Biochem 196:80–83.
Broude et al., 1994, Proc Natl Acad Sci 91:3072–3076.
Caetano–Anolles, 1994, Plant Mol Biol 25:1011–1026.
Celis et al., 1994, Cell Biology (Academic Press, New York, NY).
Chevet et al., 1995, Nucleic Acids Res 23(16):3343–3344.
Chomczynski and Sacchi, 1987, Anal Biochem 162:156–159.
Chomczynski, 1993, BioTechniques 15(3):532–536.
CLONETECHniques, Jan. 1996.
Dorper and Winnacker, 1983, Nucleic Acids Res 11(9):2575–2584.
Drmanac et al., 1991, Int Conf Electrophor, Supercomput Hum Gen, Cantor (ed.), pp. 60–74.
Drmanac et al., 1993, Science 260:1649–1652.
Drmanac et al., 1992, Electrophoresis 13:566–573.
Egholm et al., 1993, Nature 365:566–567.
Eigen et al., 1994, Proc Natl Acad Sci 91:5740–5747.
Fischer et al., 1995, Proc Natl Acad Sci 92:5331–5335.
Gautier et al., 1987, Nucleic Acids Res 15:6625–6641.
Gubler et al., 1983, Gene 25:263–269.
Guo et al., 1994, Nucleic Acids Res 22:5456–5465.
Hedgpeth et al., 1972, Proc Natl Acad Sci 69:3448–3452.
Hoheisel, 1994, TIG 10(3).
Holtke et al., 1992, BioTechniques 12(1):104–113.
Ito et al., 1994, FEBS Lett 351:231–236.
Ivanova and Belyavsky, 1995, Nucleic Acids Res 23:2954–2958.
Ju et al., 1995, Proc Natl Acad Sci 92:4347–4351.
Kato et al., 1994, Gene 243–250.
Kato, 1995, Nucleic Acids Res 23(18):3685–3690.
Kricka et al., 1995, Molecular Probing, Blotting and Sequencing Chapter I and Table IX (Academic Press, New York, NY.
Krol et al., 1988, BioTechniques 6:958–976.
Lamture, 1994, Nucleic Acids Res 22:2121–2125.
Langer et al., 1981, Proc Natl Acad Sci 78(11):6633–6637.
Lennon et al., 1991, Trends in Genetics 7(10):314–317.
Liang et al., 1992, Science 257:967–971.
Liang et al., 1994, Nucleic Acids Res 22(25):5763–5764.
Liang et al., 1995, Curr Opin Immunol 7:274–280.
Lisitsyn, 1993, Science 259:946–950.
Maier et al., 1994, Nucleic Acids Res 22(16):3423–3424.
Maniatis, 1982, Molecular Cloning: A Laboratory Manual (Cold Spring Harbor, NY) pp. 124–125, 286–288.
McClelland et al., 1995, TIG 11(6):242–246.
McClelland et al., 1993, Exs 67:103–115.
Meier–Ewert et al., 1993, Nature 361:375–376.
Mou et al., 1994, Biochem Biophys Res Comm 199(2):564–569.
Mutter et al., 1995, Nucleic Acids Res 23:1411–1418.
Okayama and Berg, 1982, Mol Cell Biol 2(2):161–170.
Olesen et al., 1993, BioTechniques 15(3):480–485.
OLIGO Version 4.0 for Macintosh, Reference Manual, Eqn. I, p. 2.
Olson, 1993, Proc Natl Acad Sci 90:4338–4344.
Pease et al.. 1994, Proc Natl Acad Sci 91:5022–5026.
Prashar and Weissman, 1996, Proc Natl Acad Sci 93:659–663.
Press et al., 1986, Numerical Recipes—The Art of Scientific Computing, §10.9, (Cambridge University Press, Cambridge, U.K.).
Sanger et al., 1977, Proc Natl Acad Sci 74(12):5436–5467.
Sarin et al., 1988, Proc Natl Acad Sci 85:7448–7451.
Schmidt and Mueller, 1996, Nucleic Acids Res 24(9):1789–1791.
Sedgewick, 1990, Algorithms in C, chapter 19, Addison–Wesley, Reading, MA.
Simpson, 1995, Technical Report.
Smith and Birnstiel, 1976, Nucleic Acids Res 3:2387–2399.
Soares et al., 1994, Proc Natl Acad Sci 91:9228–32.
Sokolov and Prockop, 1994, Nucleic Acids Res 22(19):4009–4015.
Song and Osborn, 1994, Plant Mol Biol 26:1065–1071.
Stein et al., 1988, Nucleic Acids Res 16:3209.
Stimson et al., 1995, Proc Natl Acad Sci 92:6379–6383.
Tatari et al., 1995, Proc Natl Acad Sci 92:8803–8807.
Titus et al., 1982, J Immunol Meth 50:193–204.
Ushijima et al., 1995, Mutation Research 334:283–292.
Velculescu et al., 1995, Science 270:484–487.
Watson et al., 1992 Recombinant DNA, Chapter 7 (W.H. Freeman, New York).
Welsh et al., 1992, Nucleic Acids Res 20:4965–4970.
Woolley and Mathies, 1994, Proc Natl Acad Sci 91:11348–11352.
Zon, 1988, Pharm Res 5:539–549.
Mathieu–Daude et al., 1996, Nuc. Acids Res. 24:1504–1507.
Matsubara and Okubo, 1995, Jpn. J. Pharmacol. 69:181–185.
U.S. application No. 09/298,237, Rothberg et al., filed Apr. 22, 1999.
U.S. application No. 08/942,406, Rothberg et al., filed Oct. 1, 1997.
Brenner and Livak, 1989, Proc. Natl Acad. Sci. 86:8902–8906.
Unrau and Deugau, 1994, Gene 145:163–169.
Keele, J.W. et al., 1994, J. Computational Biol. 1(1):65–79.
Okubo, K., 1992, Nature Genetics 2:173–179.
Matsubara et al., 1993, Current Opin. Biotechnol. 4:672–677.

FIG. 2A
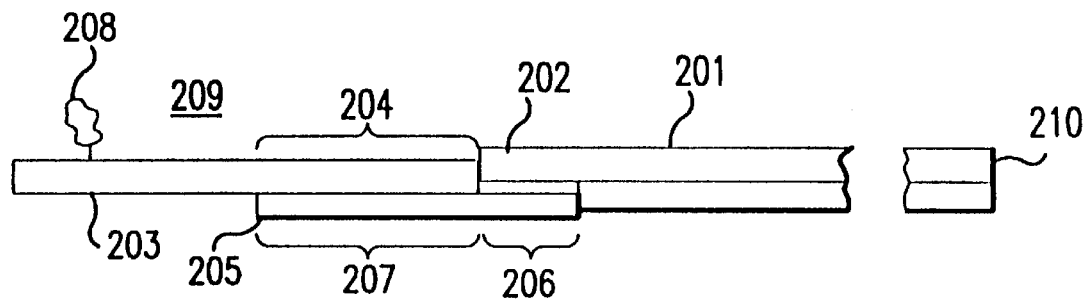
5'-AGC ACT CTC CAG CCT CTC ACC GAA-3' (SEQ ID NO:1)
250    3'- AG TGG CTT CTAG-5' (SEQ ID NO:7)
5'-ACC GAC GTC GAC TAT CCA TGA AGC-3' (SEQ ID NO:42)
251    3'-GT ACT TCG TCGA-5' (SEQ ID NO:44)
FIG. 2B
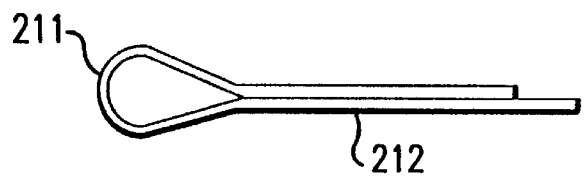
FIG. 2C

5'-AGCACTCTCCAGCCTCTCACCGAGCATG (SEQ ID NO.55)
3'-AGTGGCTC

| L | (RE1, RE1)$_{R1}$ | (RE1, RE2)$_{R1}$ | (RE2, RE2)$_{R2}$ | (RE3, RE3)$_{R2}$ | (RE3, RE4)$_{R2}$ | ... |
|---|---|---|---|---|---|---|
| ... | | | | | | |
| 52 | A01 | | | | | |
| ... | | | | | | |
| 151 | T163 | | | | | |
| ... | | | | | | |
| 175 | | A01,T163 | | A01,S003 | | |
| ... | | | | | | |
| 222 | | T163,Q012 | | | | |
| ... | | | | | | |
| 402 | | | | | | |
| ... | | | | | | |
| 532 | | | | | Q012,S003 | |
| ... | | | | | | |

VECTORS OF CUTS

MERGED AND SORTED VECTORS OF CUTS

FRAGMENTS

FRAGMENTS SEQUENCES

FIG.10D 1411
([RE1,RE1,N,52] , [RE2,RE2,y,151] ,
    [RE1,RE2,N,175] , [RE1,RE2,N,222])
                    1412

SORTED FRAGMENT VECTOR

FIG.10E

| ℓ | [RE1,RE1] | [RE1,RE2] | [RE2,RE2] | |
|---|---|---|---|---|
| ⋮ | | | | |
| 52 | +A01 | | 1412 | |
| ⋮ | | | | |
| 151 | | | +A01 | |
| ⋮ | | | | |
| 175 | | +A01 | | |
| ⋮ | | | | |
| 222 | | +A01 | | |

DIGEST TABLE

FIG.10F

METHOD AND APPARATUS FOR INDENTIFYING, CLASSIFYING, OR QUANTIFYING PROTEIN SEQUENCES IN A SAMPLE WITHOUT SEQUENCING

This is a continuation of application Ser. No. 08/942,406 filed Oct. 1, 1997, which in turn is a divisional of application Ser. No. 08/547,214, filed Oct. 24, 1995, now U.S. Pat. No. 5,871,697, each of which is hereby incorporated by reference in its entirety.

This invention was made with United States Government support under award number 70NANB5H1036 awarded by the National Institute of Standards and Technology. The United States Government has certain rights in the invention.

TABLE OF CONTENTS

1. FIELD OF THE INVENTION
2. BACKGROUND
3. SUMMARY OF THE INVENTION
4. BRIEF DESCRIPTION OF THE DRAWINGS
5. DETAILED DESCRIPTION
   5.1. QUANTITATIVE EXPRESSION ANALYSIS
   5.2. RE EMBODIMENTS OF QEA
      5.2.1. FIRST ALTERNATIVE RE EMBODIMENT
      5.2.2. SECOND ALTERNATIVE RE EMBODIMENT
   5.3. PCR EMBODIMENT OF QEA
   5.4. QEA ANALYSIS AND DESIGN METHODS
      5.4.1. QEA EXPERIMENTAL ANALYSIS METHODS
      5.4.2. QEA EXPERIMENTAL DESIGN METHODS
      5.4.3. QEA AMBIGUITY RESOLUTION
   5.5. COLONY CALLING
   5.6. CC ANALYSIS AND DESIGN METHODS
      5.6.1. CC EXPERIMENTAL ANALYSIS METHODS
      5.6.2. CC EXPERIMENTAL DESIGN METHODS
      5.6.3. CC QUANTITATIVE ALTERNATIVE
   5.7. APPARATUS FOR PERFORMING THE METHODS OF THE INVENTION
6. EXAMPLES
   6.1. SUBSEQUENCE HIT AND LENGTH INFORMATION
   6.2. RESTRICTION ENDONUCLEASES
   6.3. RNA EXTRACTION AND cDNA SYNTHESIS
   6.4. QEA PREFERRED RE METHOD
      6.4.1. cDNA PREPARATION
      6.4.2. PREFERRED RE/LIGASE AND AMPLIFICATION REACTIONS
      6.4.3. PREFERRED AUTOMATED RE/LIGASE REACTIONS
      6.4.4. ALTERNATIVE RE/LIGASE AND AMPLIFICATION REACTIONS
      6.4.5. OPTIONAL POST-AMPLIFICATION STEPS
   6.5. QEA BY THE PCR EMBODIMENT
   6.6. EXAMPLE OF SIMULATED ANNEALING
   6.7. QEA RESULTS
      6.7.1. QUERY MODE QEA RESULTS
      6.7.2. TISSUE MODE QEA RESULTS
   6.8. COLONY CALLING
   6.9. PREFERRED QEA ADAPTERS AND REs PAIRS
   6.10. FLUORESCENT LABELS
7. SPECIFIC EMBODIMENTS, CITATION OF REFERENCES

1. FIELD OF THE INVENTION

The field of this invention is DNA sequence classification, identification or determination, and quantification; more particularly it is the quantitative classification, comparison of expression, or identification of preferably all DNA sequences or genes in a sample without performing any sequencing.

2. BACKGROUND

Over the past ten years, as biological and genomic research have revolutionized our understanding of the molecular basis of life, it has become increasingly clear that the temporal and spatial expression of genes is responsible for all life's processes, processes occurring in both health and in disease. Science has progressed from an understanding of how single genetic defects cause the traditionally recognized hereditary disorders, such as the thalassemias, to a realization of the importance of the interaction of multiple genetic defects along with environmental factors in the etiology of the majority of more complex disorders, such as cancer. In the case of cancer, current scientific evidence demonstrates the key causative roles of altered expression of and multiple defects in several pivotal genes. Other complex diseases have similar etiology. Thus the more complete and reliable a correlation that can be established between gene expression and health or disease states, the better diseases can be recognized, diagnosed and treated.

This important correlation is established by the quantitative determination and classification of DNA expression in tissue samples, and such a method which is rapid and economical would be of considerable value. Genomic DNA ("gDNA") sequences are those naturally occurring DNA sequences constituting the genome of a cell. The state of gene, or gDNA, expression at any time is represented by the composition of total cellular messenger RNA ("mRNA"), which is synthesized by the regulated transcription of gDNA. Complementary DNA ("cDNA") sequences are synthesized by reverse transcription from mRNA. cDNA from total cellular mRNA also represents, albeit approximately, gDNA expression in a cell at a given time. Consequently, rapid and economical detection of all the DNA sequences in particular cDNA or gDNA samples is desired, particularly so if such detection was rapid, precise, and quantitative.

Heretofore, gene specific DNA analysis techniques have not been directed to the determination or classification of substantially all genes in a DNA sample representing total cellular mRNA and have required some degree of sequencing. Generally, existing cDNA, and also gDNA, analysis techniques have been directed to the determination and analysis of one or two known or unknown genetic sequences at one time. These techniques have used probes synthesized to specifically recognize by hybridization only one particular DNA sequence or gene. (See, e.g., Watson et al., 1992, *Recombinant DNA*, chap 7, W. H. Freeman, New York.) Further, adaptation of these methods to the problem of recognizing all sequences in a sample would be cumbersome and uneconomical.

One existing method for finding and sequencing unknown genes starts from an arrayed cDNA library. From a particular tissue or specimen, mRNA is isolated and cloned into an appropriate vector, which is then plated in a manner so that the progeny of individual vectors bearing the clone of one cDNA sequence can be separately identified. A replica of such a plate is then probed, often with a labeled DNA oligomer selected to hybridize with the cDNA representing the gene of interest. Thereby, those colonies bearing the cDNA of interest are found and isolated, the cDNA harvested and subject to sequencing. Sequencing can then be done by the Sanger dideoxy chain termination method (Sanger et al., 1977, "DNA sequencing with chain terminating inhibitors", Proc. Natl. Acad. Sci. USA 74(12):5463–5467) applied to inserts so isolated.

The DNA oligomer probes for the unknown gene used for colony selection are synthesized to hybridize, preferably, only with the cDNA for the gene of interest. One manner of achieving this specificity is to start with the protein product of the gene of interest. If a partial sequence of 5 to 10-mer peptide fragment from an active region of this protein can be determined, corresponding 15 to 30-mer degenerate oligonucleotides can be synthesized which code for this peptide. This collection of degenerate oligonucleotides will typically be sufficient to uniquely identify the corresponding gene. Similarly, any information leading to 15 to 30 long nucleotide subsequences can be used to create a single gene probe.

Another existing method, which searches for a known gene in a cDNA or gDNA prepared from a tissue sample, also uses single gene or single sequence probes which are complementary to unique subsequences of the already known gene sequences. For example, the expression of a particular oncogene in sample can be determined by probing tissue derived cDNA with a probe derived from a subsequence of the oncogene's expressed sequence tag. Similarly the presence of a rare or difficult to culture pathogen, such as the TB bacillus or the HIV, can be determined by probing gDNA with a hybridization probe specific to a gene of the pathogen. The heterozygous presence of a mutant allele in a phenotypically normal individual, or its homozygous presence in a fetus, can be determined by probing with an allele specific probe complementary only to the mutant allele (See, e.g., Guo et al., 1994, Nucleic Acid Research, 22:5456–65).

All existing methods using single gene probes, of which the preceding examples are typical, if applied to determine all genes expressed in a given tissue sample, would require many thousands to tens of thousands of individual probes. It is estimated a single human cell typically expresses approximately to 15,000 to 15,000 genes simultaneously and that the most complex tissue, e.g. the brain, can express up to half the human genome (Liang et al., 1992, "Differential Display of Eukaryotic Messenger RNA by Means of the Polymerase Chain Reaction, Science, 257:967–971). Such an application requiring such a number of probes is clearly too cumbersome to be economic or, even, practical.

Another class of existing methods, known as sequencing by hybridization ("SBH"), in contrast, use combinatorial probes which are not gene specific (Drmanac et al., 1993, Science, 260:1649–52; U.S. Pat. No. 5,202,231, Apr. 13, 1993, to Drmanac et al). An exemplary implementation of SBH to determine an unknown gene requires that a single cDNA clone be probed with all DNA oligomers of a given length, say, for example, all 6-mers. Such a set of all oligomers of a given length synthesized without any selection is called a combinatorial probe library. From knowledge of all hybridization results for a combinatorial library, say all the 4096 6-mer probe results, a partial DNA sequence for the cDNA clone can be reconstructed by algorithmic manipulations. Complete sequences are not determinable because, at least, repeated subsequences cannot be fully determined. SBH adapted to the classification of known genes is called oligomer sequence signatures ("OSS") (Lennon et al., 1991, Trends In Genetics, 7(10):314–317). This technique classifies a single clone based on the pattern of probe hits against an entire combinatorial library, or a significant sub-library. It requires that the tissue sample library be arrayed into clones, each clone comprising only one pure sequence from the library. It cannot be applied to mixtures.

These exemplary existing methods are all directed to finding one sequence in an array of clones each expressing a single sequence from a tissue sample. They are not directed to rapid, economical, quantitative, and precise characterization of all the DNA sequences in a mixture of sequences, such as a particular total cellular cDNA or gDNA sample. Their adaptation to such a task would be prohibitive. Determination by sequencing the DNA of a clone, much less an entire sample of thousands of sequences, is not rapid or inexpensive enough for economical and useful diagnostics. Existing probe-based techniques of gene determination or classification, whether the genes are known or unknown, require many thousands of probes, each specific to one possible gene to be observed, or at least thousands or even tens of thousands of probes in a combinatorial library. Further, all of these methods require the sample be arrayed into clones each expressing a single gene of the sample.

In contrast to the prior exemplary existing gene determination and classification techniques, another existing technique, known as differential display, attempts to fingerprint a mixture of expressed genes, as is found in a pooled cDNA library. This fingerprint, however, seeks merely to establish whether two samples are the same or different. No attempt is made to determine the quantitative, or even qualitative, expression of particular, determined genes (Liang et al., 1995, Current Opinions in Immunology 7:274–280; Liang et al., 1992, Science 257:967–71; Welsh et al., Nucleic Acid Res., 1992, 20:4965–70; McClelland et al., 1993, Exs, 67:103–15; Lisitsyn, 1993, Science, 259:946–50). Differential display uses the polymerase chain reaction ("PCR") to amplify DNA subsequences of various lengths, which are defined by being between the hybridization sites of arbitrarily selected primers. Ideally, the pattern of lengths observed is characteristic of the tissue from which the library was prepared. Typically, one primer used in differential display is oligo(dT) and the other is one or more arbitrary oligonucleotides designed to hybridize within a few hundred base pairs of the poly-dA tail of a cDNA in the library. Thereby, on electrophoretic separation, the amplified fragments of lengths up to a few hundred base pairs should generate bands characteristic and distinctive of the sample. Changes in tissue gene expression may be observed as changes in one or more bands.

Although characteristic banding patterns develop, no attempt is made to link these patterns to the expression of particular genes. The second arbitrary primer cannot be traced to a particular gene. First, the PCR process is less than ideally specific. One to a few base pair ("bp") mismatches ("bubbles") are permitted by the lower stringency annealing step typically used and are tolerated well enough so that a new chain can be initiated by the Taq polymerase, often used in PCR reactions. Second, the location of a single subsequence or its absence is insufficient information to distinguish all expressed genes. Third, length information from the arbitrary primer to the poly-dA tail is generally not found to be characteristic of a sequence due to variations in the processing of the 3' untranslated regions of genes, the variation in the poly-adenylation process and variability in priming to the repetitive sequence at a precise point. Thus, even the bands that are produced often are smeared by the non-specific background sequences present. Also known PCR biases to high G+C content and short sequences further limit the specificity of this method. Thus this technique is generally limited to "fingerprinting" samples for a similarity or dissimilarity determination and is precluded from use in quantitative determination of the differential expression of identifiable genes.

Existing methods for gene or DNA sequence classification or determination are in need of improvement in their ability to perform rapid and economical as well as quantitative and specific determination of the components of a cDNA mixture prepared from a tissue sample. The preceding background review identifies the deficiencies of several exemplary existing methods.

3. SUMMARY OF THE INVENTION

It is an object of this invention to provide methods for rapid, economical, quantitative, and precise determination or classification of DNA sequences, in particular genomic or complementary DNA sequences, in either arrays of single sequence clones or mixtures of sequences such as can be derived from tissue samples, without actually sequencing the DNA. Thereby, the deficiencies in the background arts just identified are solved. This object is realized by generating a plurality of distinctive and detectable signals from the DNA sequences in the sample being analyzed. Preferably, all the signals taken together have sufficient discrimination and resolution so that each particular DNA sequence in a sample may be individually classified by the particular signals it generates, and with reference to a database of DNA sequences possible in the sample, individually determined. The intensity of the signals indicative of a particular DNA sequence depends quantitatively on the amount of that DNA present. Alternatively, the signals together can classify a predominant fraction of the DNA sequences into a plurality of sets of approximately no more than two to four individual sequences.

It is a further object that the numerous signals be generated from measurements of the results of as few a number of recognition reactions as possible, preferably no more than approximately 5–400 reactions, and most preferably no more than approximately 20–50 reactions. Rapid and economical determinations would not be achieved if each DNA sequence in a sample containing a complex mixture required a separate reaction with a unique probe. Preferably, each recognition reaction generates a large number of or a distinctive pattern of distinguishable signals, which are quantitatively proportional to the amount of the particular DNA sequences present. Further, the signals are preferably detected and measured with a minimum number of observations, which are preferably capable of simultaneous performance.

The signals are preferably optical, generated by fluorochrome labels and detected by automated optical detection technologies. Using these methods, multiple individually labeled moieties can be discriminated even though they are in the same filter spot or gel band. This permits multiplexing reactions and parallelizing signal detection. Alternatively, the invention is easily adaptable to other labeling systems, for example, silver staining of gels. In particular, any single molecule detection system, whether optical or by some other technology such as scanning or tunneling microscopy, would be highly advantageous for use according to this invention as it would greatly improve quantitative characteristics.

According to this invention, signals are generated by detecting the presence (hereinafter called "hits") or absence of short DNA subsequences (hereinafter called "target" subsequences) within a nucleic acid sequence of the sample to be analyzed. The presence or absence of a subsequence is detected by use of recognition means, or probes, for the subsequence. The subsequences are recognized by recognition means of several sorts, including but not limited to restriction endonucleases ("REs"), DNA oligomers, and PNA oligomers. REs recognize their specific subsequences by cleavage thereof; DNA and PNA oligomers recognize their specific subsequences by hybridization methods. The preferred embodiment detects not only the presence of pairs of hits in a sample sequence but also include a representation of the length in base pairs between adjacent hits. This length representation can be corrected to true physical length in base pairs upon removing experimental biases and errors of the length separation and detection means. An alternative embodiment detects only the pattern of hits in an array of clones, each containing a single sequence ("single sequence clones").

The generated signals are then analyzed together with DNA sequence information stored in sequence databases in computer implemented experimental analysis methods of this invention to identify individual genes and their quantitative presence in the sample.

The target subsequences are chosen by further computer implemented experimental design methods of this invention such that their presence or absence and their relative distances when present yield a maximum amount of information for classifying or determining the DNA sequences to be analyzed. Thereby it is possible to have orders of magnitude fewer probes than there are DNA sequences to be analyzed, and it is further possible to have considerably fewer probes than would be present in combinatorial libraries of the same length as the probes used in this invention. For each embodiment, target subsequences have a preferred probability of occurrence in a sequence, typically between 5% and 50%. In all embodiments, it is preferred that the presence of one probe in a DNA sequence to be analyzed is independent of the presence of any other probe.

Preferably, target subsequences are chosen based on information in relevant DNA sequence databases that characterize the sample. A minimum number of target subsequences may be chosen to determine the expression of all genes in a tissue sample ("tissue mode"). Alternatively, a smaller number of target subsequences may be chosen to quantitatively classify or determine only one or a few sequences of genes of interest, for example oncogenes, tumor suppressor genes, growth factors, cell cycle genes, cytoskeletal genes, etc ("query mode").

A preferred embodiment of the invention, named quantitative expression analysis ("QEA"), produces signals comprising target subsequence presence and a representation of the length in base pairs along a gene between adjacent target subsequences by measuring the results of recognition reactions on cDNA (or gDNA) mixtures. Of great importance, this method does not require the cDNA be inserted into a vector to create individual clones in a library. Creation of these libraries is time consuming, costly, and introduces bias into the process, as it requires the cDNA in the vector to be transformed into bacteria, the bacteria arrayed as clonal colonies, and finally the growth of the individual transformed colonies.

Three exemplary experimental methods are described herein for performing QEA: a preferred method utilizing a novel RE/ligase/amplification procedure; a PCR based method; and a method utilizing a removal means, preferably biotin, for removal of unwanted DNA fragments. The preferred method generates precise, reproducible, noise free signatures for determining individual gene expression from DNA in mixtures or libraries and is uniquely adaptable to automation, since it does not require intermediate extractions or buffer exchanges. A computer implemented gene calling step uses the hit and length information measured in conjunction with a database of DNA sequences to determine which genes are present in the sample and the relative levels of expression. Signal intensities are used to determine relative amounts of sequences in the sample. Computer implemented design methods optimize the choice of the target subsequences.

A second specific embodiment of the invention, termed colony calling ("CC"), gathers only target subsequence presence information for all target subsequences for arrayed, individual single sequence clones in a library, with cDNA libraries being preferred. The target subsequences are carefully chosen according to computer implemented design methods of this invention to have a maximum information content and to be minimum in number. Preferably from 10–20 subsequences are sufficient to characterize the expressed cDNA in a tissue. In order to increase the specificity and reliability of hybridization to the typically short DNA subsequences, preferable recognition means are PNAs. Degenerate sets of longer DNA oligomers having a common, short, shared, target sequence can also be used as a recognition means. A computer implemented gene calling step uses the pattern of hits in conjunction with a database of DNA sequences to determine which genes are present in the sample and the relative levels of expression.

The embodiments of this invention preferably generate measurements that are precise, reproducible, and free of noise. Measurement noise in QEA is typically created by generation or amplification of unwanted DNA fragments, and special steps are preferably taken to avoid any such unwanted fragments. Measurement noise in colony calling is typically created by mis-hybridization of probes, or recognition means, to colonies. High stringency reaction conditions and DNA mimics with increased hybridization specificity may be used to minimize this noise. DNA mimics are polymers composed of subunits capable of specific, Watson-Crick-like hybridization with DNA. Also useful to minimize noise in colony calling are improved hybridization detection methods. Instead of the conventional detection methods based on probe labeling with fluorochromes, new methods are based on light scattering by small 100–200 μm particles that are aggregated upon probe hybridization (Stimson et al., 1995, "Real-time detection of DNA hybridization and melting on oligonucleotide arrays by using optical wave guides", Proc. Natl. Acad. Sci. USA, 92:6379–6383). In this method, the hybridization surface forms one surface of a light pipe or optical wave guide, and the scattering induced by these aggregated particles causes light to leak from the light pipe. In this manner hybridization is revealed as an illuminated spot of leaking light on a dark background. This latter method makes hybridization detection more rapid by eliminating the need for a washing step between the hybridization and detection steps. Further by using variously sized and shaped particles with different light scattering properties, multiple probe hybridizations can be detected from one colony.

Further, the embodiments of the invention can be adapted to automation by eliminating non-automatable steps, such as extractions or buffer exchanges. The embodiments of the invention facilitate efficient analysis by permitting multiple recognition means to be tested in one reaction and by utilizing multiple, distinguishable labeling of the recognition means, so that signals may be simultaneously detected and measured. Preferably, for the QEA embodiments, this labeling is by multiple fluorochromes. For the CC embodiments, detection is preferably done by the light scattering methods with variously sized and shaped particles.

An increase in sensitivity as well as an increase in the number of resolvable fluorescent labels can be achieved by the use of fluorescent, energy transfer, dye-labeled primers. Other detection methods, preferable when the genes being identified will be physically isolated from the gel for later sequencing or use as experimental probes, include the use of silver staining gels or of radioactive labeling. Since these methods do not allow for multiple samples to be run in a single lane, they are less preferable when high throughput is needed.

Because this invention achieves rapid and economical determination of quantitative gene expression in tissue or other samples, it has considerable medical and research utility. In medicine, as more and more diseases are recognized to have important genetic components to their etiology and development, it is becoming increasingly useful to be able to assay the genetic makeup and expression of a tissue sample. For example, the presence and expression of certain genes or their particular alleles are prognostic or risk factors for disease (including disorders). Several examples of such diseases are found among the neurodegenerative diseases, such as Huntington's disease and ataxia-telangiectasia. Several cancers, such as neuroblastoma, can now be linked to specific genetic defects. Finally, gene expression can also determine the presence and classification of those foreign pathogens that are difficult or impossible to culture in vitro but which nevertheless express their own unique genes.

Disease progression is reflected in changes in genetic expression of an affected tissue. For example, expression of particular tumor promoter genes and lack of expression of particular tumor suppressor genes is now known to correlate with the progression of certain tumors from normal tissue, to hyperplasia, to cancer in situ, and to metastatic cancer. Return of a cell population to a normal pattern of gene expression, such as by using anti-sense technology, can correlate with tumor regression. Therefore, knowledge of gene expression in a cancerous tissue can assist in staging and classifying this disease.

Expression information can also be used to chose and guide therapy. Accurate disease classification and staging or grading using gene expression information can assist in choosing initial therapies that are increasingly more precisely tailored to the precise disease process occurring in the particular patient. Gene expression information can then track disease progression or regression, and such information can assist in monitoring the success or changing the course of an initial therapy. A therapy is favored that results in a regression towards normal of an abnormal pattern of gene expression in an individual, while therapy which has little effect on gene expression or its progression can need modification. Such monitoring is now useful for cancers and will become useful for an increasing number of other diseases, such as diabetes and obesity. Finally, in the case of direct gene therapy, expression analysis directly monitors the success of treatment.

In biological research, rapid and economical assay for gene expression in tissue or other samples has numerous applications. Such applications include, but are not limited to, for example, in pathology examining tissue specific genetic response to disease, in embryology determining developmental changes in gene expression, in pharmacology assessing direct and indirect effects of drugs on gene expression. In these applications, this invention can be applied, e.g., to in vitro cell populations or cell lines, to in vivo animal models of disease or other processes, to human samples, to purified cell populations perhaps drawn from actual wild-type occurrences, and to tissue samples containing mixed cell populations. The cell or tissue sources can advantageously be a plant, a single celled animal, a multicellular animal, a bacterium, a virus, a fungus, or a yeast, etc. The animal can advantageously be laboratory animals used in research, such as mice engineered or bread to have certain genomes or disease conditions or tendencies. The in vitro cell populations or cell lines can be exposed to various exogenous factors to determine the effect of such factors on gene expression. Further, since an unknown signal pattern is indicative of an as yet unknown gene, this invention has important use for the discovery of new genes. In medical research, by way of further example, use of the methods of this invention allow correlating gene expression with the presence and progress of a disease and thereby provide new methods of diagnosis and new avenues of therapy which seek to directly alter gene expression.

This invention includes various embodiments and aspects, several of which are described below.

In a first embodiment, the invention provides a method for identifying, classifying, or quantifying one or more nucleic acids in a sample comprising a plurality of nucleic acids having different nucleotide sequences, said method comprising probing said sample with one or more recognition means, each recognition means recognizing a different target nucleotide subsequence or a different set of target nucleotide subsequences; generating one or more signals from said sample probed by said recognition means, each generated signal arising from a nucleic acid in said sample and comprising a representation of (i) the length between occurrences of target subsequences in said nucleic acid and (ii) the identities of said target subsequences in said nucleic acid or the identities of said sets of target subsequences among which is included the target subsequences in said nucleic acid; and searching a nucleotide sequence database to determine sequences that match or the absence of any sequences that match said one or more generated signals, said database comprising a plurality of known nucleotide sequences of nucleic acids that may be present in the sample, a sequence from said database matching a generated signal when the sequence from said database has both (i) the same length between occurrences of target subsequences as is represented by the generated signal and (ii) the same target subsequences as is represented by the generated signal, or target subsequences that are members of the same sets of target subsequences represented by the generated signal, whereby said one or more nucleic acids in said sample are identified, classified, or quantified.

This invention further provides in the first embodiment additional methods wherein each recognition means recognizes one target subsequence, and wherein a sequence from said database matches a generated signal when the sequence from said database has both the same length between occurrences of target subsequences as is represented by the generated signal and the same target subsequences as represented by the generated signal, or optionally wherein each recognition means recognizes a set of target subsequences, and wherein a sequence from said database matches a generated signal when the sequence from said database has both the same length between occurrences of target subsequences as is represented by the generated signal, and target subsequences that are members of the sets of target subsequences represented by the generated signal.

This invention further provides in the first embodiment additional methods further comprising dividing said sample of nucleic acids into a plurality of portions and performing the methods of this object individually on a plurality of said portions, wherein a different one or more recognition means are used with each portion.

This invention further provides in the first embodiment additional methods wherein the quantitative abundance of a nucleic acid comprising a particular nucleotide sequence in the sample is determined from the quantitative level of the one or more signals generated by said nucleic acid that are determined to match said particular nucleotide sequence.

This invention further provides in the first embodiment additional methods wherein said plurality of nucleic acids are DNA, and optionally wherein the DNA is cDNA, and optionally wherein the cDNA is prepared from a plant, an single celled animal, a multicellular animal, a bacterium, a virus, a fungus, or a yeast, and optionally wherein the cDNA is of total cellular RNA or total cellular poly(A) RNA.

This invention further provides in the first embodiment additional methods wherein said database comprises substantially all the known expressed sequences of said plant, single celled animal, multicellular animal, bacterium, or yeast.

This invention further provides in the first embodiment additional methods wherein the recognition means are one or more restriction endonucleases whose recognition sites are said target subsequences, and wherein the step of probing comprises digesting said sample with said one or more restriction endonucleases into fragments and ligating double stranded adapter DNA molecules to said fragments to produce ligated fragments, each said adapter DNA molecule comprising (i) a shorter stand having no 5' terminal phosphates and consisting of a first and second portion, said first portion at the 5' end of the shorter strand being complementary to the overhang produced by one of said restriction endonucleases and (ii) a longer strand having a 3' end subsequence complementary to said second portion of the shorter strand; and wherein the step of generating further comprises melting the shorter strand from the ligated fragments, contacting the sample with a DNA polymerase, extending the ligated fragments by synthesis with the DNA polymerase to produce blunt-ended double stranded DNA fragments, and amplifying the blunt-ended fragments by a method comprising contacting said blunt-ended fragments with a DNA polymerase and primer oligodeoxynucleotides, said primer oligodeoxynucleotides comprising the longer adapter strand, and said contacting being at a temperature not greater than the melting temperature of the primer oligodeoxynucleotide from a strand of the blunt-ended fragments complementary to the primer oligodeoxynucleotide and not less than the melting temperature of the shorter strand of the adapter nucleic acid from the blunt-ended fragments.

This invention further provides in the first embodiment additional methods wherein the recognition means are one or more restriction endonucleases whose recognition sites are said target subsequences, and wherein the step of probing further comprises digesting the sample with said one or more restriction endonucleases.

This invention further provides in the first embodiment additional methods further comprising identifying a fragment of a nucleic acid in the sample which generates said one or more signals; and recovering said fragment, and optionally wherein the signals generated by said recovered fragment do not match a sequence in said nucleotide sequence database, and optionally further comprising using at least a hybridizable portion of said fragment as a hybridization probe to bind to a nucleic acid that can generate said fragment upon digestion by said one or more restriction endonucleases.

This invention further provides in the first embodiment additional methods wherein the step of generating further comprises after said digesting removing from the sample both nucleic acids which have not been digested and nucleic acid fragments resulting from digestion at only a single terminus of the fragments, and optionally wherein prior to digesting, the nucleic acids in the sample are each bound at one terminus to a biotin molecule or to a hapten molecule, and said removing is carried out by a method which comprises contacting the nucleic acids in the sample with streptavidin or avidin or with an anti-hapten antibody, respectively, affixed to a solid support.

This invention further provides in the first embodiment additional methods wherein said digesting with said one or more restriction endonucleases leaves single-stranded nucleotide overhangs on the digested ends.

This invention further provides in the first embodiment additional methods wherein the step of probing further comprises hybridizing double-stranded adapter nucleic acids with the digested sample fragments, each said adapter nucleic acid having an end complementary to said overhang generated by a particular one of the one or more restriction endonucleases, and ligating with a ligase a strand of said adapter nucleic acids to the 5' end of a strand of the digested sample fragments to form ligated nucleic acid fragments.

This invention further provides in the first embodiment additional methods wherein said digesting with said one or more restriction endonucleases and said ligating are carried out in the same reaction medium, and optionally wherein said digesting and said ligating comprises incubating said reaction medium at a first temperature and then at a second temperature, in which said one or more restriction endonucleases are more active at the first temperature than the second temperature and said ligase is more active at the second temperature that the first temperature, or wherein said incubating at said first temperature and said incubating at said second temperature are performed repetitively.

This invention further provides in the first embodiment additional methods wherein the step of probing further comprises prior to said digesting removing terminal phosphates from DNA in said sample by incubation with an alkaline phosphatase, and optionally wherein said alkaline phosphatase is heat labile and is heat inactivated prior to said digesting.

This invention further provides in the first embodiment additional methods wherein said generating step comprises amplifying the ligated nucleic acid fragments, and optionally wherein said amplifying is carried out by use of a nucleic acid polymerase and primer nucleic acid strands, said primer nucleic acid strands being capable of priming nucleic acid synthesis by said polymerase, and optionally wherein the primer nucleic acid strands have a G+C content of between 40% and 60%.

This invention further provides in the first embodiment additional methods wherein each said adapter nucleic acid has a shorter strand and a longer strand, the longer strand being ligated to the digested sample fragments, and said generating step comprises prior to said amplifying step the melting of the shorter strand from the ligated fragments, contacting the ligated fragments with a DNA polymerase, extending the ligated fragments by synthesis with the DNA polymerase to produce blunt-ended double stranded DNA fragments, and wherein the primer nucleic acid strands comprise a hybridizable portion the sequence of said longer strands, or optionally comprise the sequence of said longer strands, each different primer nucleic acid strand priming amplification only of blunt ended double stranded DNA fragments that are produced after digestion by a particular restriction endonuclease.

This invention further provides in the first embodiment additional methods wherein each primer nucleic acid strand is specific for a particular restriction endonuclease, and further comprises at the 3' end of and contiguous with the longer strand sequence the portion of the restriction endonuclease recognition site remaining on a nucleic acid fragment terminus after digestion by the restriction endonuclease, or optionally wherein each said primer specific for a particular restriction endonuclease further comprises at its 3' end one or more nucleotides 3' to and contiguous with the remaining portion of the restriction endonuclease recognition site, whereby the ligated nucleic acid fragment amplified is that comprising said remaining portion of said restriction endonuclease recognition site contiguous to said one or more additional nucleotides, and optionally such that said primers comprising a particular said one or more additional nucleotides can be distinguishably detected from said primers comprising a different said one or more additional nucleotides.

This invention further provides in the first embodiment additional methods wherein during said amplifying step the primer nucleic acid strands are annealed to the ligated nucleic acid fragments at a temperature that is less than the melting temperature of the primer nucleic acid strands from strands complementary to the primer nucleic acid strands but greater than the melting temperature of the shorter adapter strands from the blunt-ended fragments.

This invention further provides in the first embodiment additional methods wherein the recognition means are oligomers of nucleotides, nucleotide-mimics, or a combination of nucleotides and nucleotide-mimics, which are specifically hybridizable with the target subsequences, and optionally further provides additional methods wherein the step of generating comprises amplifying with a nucleic acid polymerase and with primers comprising said oligomers, whereby fragments of nucleic acids in the sample between hybridized oligomers are amplified.

This invention further provides in the first embodiment additional methods wherein said signals further comprise a representation of whether an additional target subsequence is present on said nucleic acid in the sample between said occurrences of target subsequences, and optionally wherein said additional target subsequence is recognized by a method comprising contacting nucleic acids in the sample with oligomers of nucleotides, nucleotide-mimics, or mixed nucleotides and nucleotide-mimics, which are hybridizable with said additional target subsequence.

This invention further provides in the first embodiment additional methods wherein the step of generating comprises suppressing said signals when an additional target subsequence is present on said nucleic acid in the sample between said occurrences of target subsequences, and optionally wherein, when the step of generating comprises amplifying nucleic acids in the sample, said additional target subsequence is recognized by a method comprising contacting nucleic acids in the sample with (a) oligomers of nucleotides, nucleotide-mimics, or mixed nucleotides and nucleotide-mimics, which hybridize with said additional target subsequence and disrupt the amplifying step; or (b) restriction endonucleases which have said additional target subsequence as a recognition site and digest the nucleic acids in the sample at the recognition site.

This invention further provides in the first embodiment additional methods wherein the step of generating further comprises separating nucleic acid fragments by length, and optionally wherein the step of generating further comprises detecting said separated nucleic acid fragments, and optionally wherein said detecting is carried out by a method comprising staining said fragments with silver, labeling said fragments with a DNA intercalating dye, or detecting light emission from a fluorochrome label on said fragments.

This invention further provides in the first embodiment additional methods wherein said representation of the length between occurrences of target subsequences is the length of fragments determined by said separating and detecting steps.

This invention further provides in the first embodiment additional methods wherein said separating is carried out by use of liquid chromatography, mass spectrometry, or electrophoresis, and optionally wherein said electrophoresis is carried out in a slab gel or capillary configuration using a denaturing or non-denaturing medium.

This invention further provides in the first embodiment additional methods wherein a predetermined one or more nucleotide sequences in said database are of interest, and wherein the target subsequences are such that said sequences of interest generate at least one signal that is not generated by any other sequence likely to be present in the sample, and optionally wherein the nucleotide sequences of interest are a majority of sequences in said database.

This invention further provides in the first embodiment additional methods wherein the target subsequences have a probability of occurrence in the nucleotide sequences in said database of from approximately 0.01 to approximately 0.30.

This invention further provides in the first embodiment additional methods wherein the target subsequences are such that the majority of sequences in said database contain on average a sufficient number of occurrences of target subsequences in order to on average generate a signal that is not generated by any other nucleotide sequence in said database, and optionally wherein the number of pairs of target subsequences present on average in the majority of sequences in said database is no less than 3, and wherein the average number of signals generated from the sequences in said database is such that the average difference between lengths represented by the generated signals is greater than or equal to 1 base pair.

This invention further provides in the first embodiment additional methods wherein the target subsequences have a probability of occurrence, p, approximately given by the solution of $$\frac{R(R+1)p^2}{2} = A$$

and $$\frac{L}{Np^2} = B$$

wherein N=the number of different nucleotide sequences in said database; L=the average length of said different nucleotide sequences in said database; R=the number of recognition means; A=the number of pairs of target subsequences present on average in said different nucleotide sequences in said database; and B=the average difference between lengths represented by the signals generated from the nucleic acids in the sample, and optionally wherein A is greater than or equal to 3 and wherein B is greater than or equal to 1.

This invention further provides in the first embodiment additional methods wherein the target subsequences are selected according to the further steps comprising determining a pattern of signals that can be generated and the sequences capable of generating each such signal by simulating the steps of probing and generating applied to each sequences in said database of nucleotide sequences; ascertaining the value of said determined pattern according to an information measure; and choosing the target subsequences in order to generate a new pattern that optimizes the information measure, and optionally wherein said choosing step selects target subsequences which comprise the recognition sites of the one or more restriction endonucleases, and optionally wherein said choosing step selects target subsequences which comprise the recognition sites of the one or more restriction endonucleases contiguous with one or more additional nucleotides.

This invention further provides in the first embodiment additional methods wherein a predetermined one or more of the nucleotide sequences present in said database of nucleotide sequences are of interest, and the information measure optimized is the number of such said sequences of interest which generate at least one signal that is not generated by any other nucleotide sequence present in said database, and optionally wherein said nucleotide sequences of interest are a majority of the nucleotide sequences present in said database.

This invention further provides in the first embodiment additional methods wherein said choosing step is by exhaustive search of all combinations of target subsequences of length less than approximately 10, or wherein said step of choosing target subsequences is by a method comprising simulated annealing.

This invention further provides in the first embodiment additional methods wherein the step of searching further comprises determining a pattern of signals that can be generated and the sequences capable of generating each such signal by simulating the steps of probing and generating applied to each sequence in said database of nucleotide sequences; and finding the one or more nucleotide sequences in said database that are able to generate said one or more generated signals by finding in said pattern those signals that comprise a representation of the (i) the same lengths between occurrences of target subsequences as is represented by the generated signal and (ii) the same target subsequences as is represented by the generated signal, or target subsequences that are members of the same sets of target subsequences represented by the generated signal.

This invention further provides in the first embodiment additional methods wherein the step of determining further comprises searching for occurrences of said target subsequences or sets of target subsequences in nucleotide sequences in said database of nucleotide sequences; finding the lengths between occurrences of said target subsequences or sets of target subsequences in the nucleotide sequences of said database; and forming the pattern of signals that can be generated from the sequences of said database in which the target subsequences were found to occur.

This invention further provides in the first embodiment additional methods wherein said restriction endonucleases generate 5' overhangs at the terminus of digested fragments and wherein each double stranded adapter nucleic acid comprises a shorter nucleic acid strand consisting of a first and second contiguous portion, said first portion being a 5' end subsequence complementary to the overhang produced by one of said restriction endonucleases; and a longer nucleic acid strand having a 3' end subsequence complementary to said second portion of the shorter strand.

This invention further provides in the first embodiment additional methods wherein said shorter strand has a melting temperature from a complementary strand of less than approximately 68° C., and has no terminal phosphate, and optionally wherein said shorter strand is approximately 12 nucleotides long.

This invention further provides in the first embodiment additional methods wherein said longer strand has a melting temperature from a complementary strand of greater than approximately 68° C., is not complementary to any nucleotide sequence in said database, and has no terminal phosphate, and optionally wherein said ligated nucleic acid fragments do not contain a recognition site for any of said restriction endonucleases, and optionally wherein said longer strand is approximately 24 nucleotides long and has a G+C content between 40% and 60%.

This invention further provides in the first embodiment additional methods wherein said one or more restriction endonucleases are heat inactivated before said ligating.

This invention further provides in the first embodiment additional methods wherein said restriction endonucleases generate 3' overhangs at the terminus of the digested fragments and wherein each double stranded adapter nucleic acid comprises a longer nucleic acid strand consisting of a first and second contiguous portion, said first portion being a 3' end subsequence complementary to the overhang produced by one of said restriction endonucleases; and a shorter nucleic acid strand complementary to the 3' end of said second portion of the longer nucleic acid stand.

This invention further provides in the first embodiment additional methods wherein said shorter strand has a melting temperature from said longer strand of less than approximately 68° C., and has no terminal phosphates, and optionally wherein said shorter strand is 12 base pairs long.

This invention further provides in the first embodiment additional methods wherein said longer strand has a melting temperature from a complementary strand of greater than approximately 68° C., is not complementary to any nucleotide sequence in said database, has no terminal phosphate, and wherein said ligated nucleic acid fragments do not contain a recognition site for any of said restriction endonucleases, and optionally wherein said longer strand is 24 base pairs long and has a G+C content between 40% and 60%.

In a second embodiment, the invention provides a method for identifying or classifying a nucleic acid comprising probing said nucleic acid with a plurality of recognition means, each recognition means recognizing a target nucleotide subsequence or a set of target nucleotide subsequences, in order to generate a set of signals, each signal representing whether said target subsequence or one of said set of target subsequences is present or absent in said nucleic acid; and searching a nucleotide sequence database, said database comprising a plurality of known nucleotide sequences of nucleic acids that may be present in the sample, for sequences matching said generated set of signals, a sequence from said database matching a set of signals when the sequence from said database (i) comprises the same target subsequences as are represented as present, or comprises target subsequences that are members of the sets of target subsequences represented as present by the generated sets of signals and (ii) does not comprise the target subsequences represented as absent or that are members of the sets of target subsequences represented as absent by the generated sets of signals, whereby the nucleic acid is identified or classified, and optionally wherein the set of signals are represented by a hash code which is a binary number.

This invention further provides in the second embodiment additional methods wherein the step of probing generates quantitative signals of the numbers of occurrences of said target subsequences or of members of said set of target subsequences in said nucleic acid, and optionally wherein a sequence matches said generated set of signals when the sequence from said database comprises the same target subsequences with the same number of occurrences in said sequence as in the quantitative signals and does not comprise the target subsequences represented as absent or target subsequences within the sets of target subsequences represented as absent.

This invention further provides in the second embodiment additional methods wherein said plurality of nucleic acids are DNA.

This invention further provides in the second embodiment additional methods wherein the recognition means are detectably labeled oligomers of nucleotides, nucleotide-mimics, or combinations of nucleotides and nucleotide-mimics, and the step of probing comprises hybridizing said nucleic acid with said oligomers, and optionally wherein said detectably labeled oligomers are detected by a method comprising detecting light emission from a fluorochrome label on said oligomers or arranging said labeled oligomers to cause light to scatter from a light pipe and detecting said scattering, and optionally wherein the recognition means are oligomers of peptido-nucleic acids, and optionally wherein the recognition means are DNA oligomers, DNA oligomers comprising universal nucleotides, or sets of partially degenerate DNA oligomers.

This invention further provides in the second embodiment additional methods wherein the step of searching further comprises determining a pattern of sets of signals of the presence or absence of said target subsequences or said sets of target subsequences that can be generated and the sequences capable of generating each set of signals in said pattern by simulating the step of probing as applied to each sequence in said database of nucleotide sequences; and finding one or more nucleotide sequences that are capable of generating said generated set of signals by finding in said pattern those sets that match said generated set, where a set of signals from said pattern matches a generated set of signals when the set from said pattern (i) represents as present the same target subsequences as are represented as present target subsequences that are members of the sets of target subsequences represented as present by the generated sets of signals and (ii) represents as absent the target subsequences represented as absent or that are members of the sets of target subsequences represented as absent by the generated sets of signals.

This invention further provides in the second embodiment additional methods wherein the target subsequences are selected according to the further steps comprising determining (i) a pattern of sets of signals representing the presence or absence of said target subsequences or of said sets of target subsequences that can be generated, and (ii) the sequences capable of generating each set of signals in said pattern by simulating the step of probing as applied to each sequence in said database of nucleotide sequences; ascertaining the value of said pattern generated according to an information measure; and choosing the target subsequences in order to generate a new pattern that optimizes the information measure.

This invention further provides in the second embodiment additional methods wherein the information measure is the number of sets of signals in the pattern which are capable of being generated by one or more sequences in said database, or optionally wherein the information measure is the number of sets of signals in the pattern which are capable of being generated by only one sequence in said database.

This invention further provides in the second embodiment additional methods wherein said choosing step is by a method comprising exhaustive search of all combination of target subsequences of length less than approximately 10, or optionally wherein said choosing step is by a method comprising simulated annealing.

This invention further provides in the second embodiment additional methods wherein the step of determining by simulating further comprises searching for the presence or absence of said target subsequences or sets of target subsequences in each nucleotide sequence in said database of nucleotide sequences; and forming the pattern of sets of signals that can be generated from said sequences in said database, and optionally where the step of searching is carried out by a string search, and optionally wherein the step of searching comprises counting the number of occurrences of said target subsequences in each nucleotide sequence.

This invention further provides in the second embodiment additional methods wherein the target subsequences have a probability of occurrence in a nucleotide sequence in said database of nucleotide sequences of from 0.01 to 0.6, or optionally wherein the target subsequences are such that the presence of one target subsequence in a nucleotide sequence in said database of nucleotide sequences is substantially independent of the presence of any other target subsequence in the nucleotide sequence, or optionally wherein fewer than approximately 50 target subsequences are selected.

In a third embodiment, the invention provides a programmable apparatus for analyzing signals comprising an inputting device for inputting one or more actual signals generated by probing a sample comprising a plurality of nucleic acids with recognition means, each recognition means recognizing a target nucleotide subsequence or a set of target nucleotide subsequences, said signals comprising a representation of (i) the length between occurrences of said target subsequences in a nucleic acid of said sample, and (ii) the identities of said target subsequences in said nucleic acid, or the identities of said sets of target subsequences among which is included the target subsequences in said nucleic acid; a searching device operatively coupled to said accepting device for searching a sequence in a nucleotide sequence database for occurrences of said target subsequences or target subsequences that are members of said sets of target subsequences, and for the length between such occurrences, said database comprising a plurality of known nucleotide sequences that may be present in said sample; a comparing device operatively coupled to said accepting device and to said searching device for finding a match between said one or more actual signals and a sequence in said database, said one or more actual signals matching a sequence from said database when the sequence from said database has both (i) the same length between occurrences of target subsequences as is represented by said one or more actual signals and (ii) the same target subsequences as is represented by said one or more actual signals or target subsequences that are members of the same sets of target subsequences represented by said one or more actual signals; and a control device operatively coupled to said comparing device for causing said comparing to be done for sequences in the database and for outputting those database sequences that match said one or more actual signals, and optionally wherein said searching device searches for said target subsequences or a set of target nucleotide subsequences in said database sequences by performing a string comparison of the nucleotides in said subsequences with those in said database sequence.

This invention further provides in the third embodiment that said control device further comprises causing said searching device to search substantially all sequences in said database in order to determine a pattern of signals that can be generated by probing said sample with said recognition means, and wherein said control device further causes said comparing device to find any matches between said one or more actual signals and said pattern of signals, said one or more actual signals matching a signal in said pattern of signals when the signal from said pattern represents (i) the same length between occurrences of target subsequences as is represented by said one or more actual signals and (ii) the same target subsequences as is represented by said one or more actual signals or target subsequences that are members of the same sets of target subsequences represented by said one or more actual signals.

This invention further provides in the third embodiment that said sample of nucleic acids comprises cDNA from RNA of a cell or tissue type, and said database comprises DNA sequences that are likely to be expressed by d cell or tissue type.

This invention further provides in the third embodiment a computer readable memory that can be used to direct a programmable apparatus to function for analyzing signals according to steps comprising inputting one or more actual signals generated by probing a sample comprising a plurality of nucleic acids with recognition means, each recognition means recognizing a target nucleotide subsequence or a set of target nucleotide subsequences, said signals comprising a representation of (i) the length between occurrences of said target subsequences in a nucleic acid of said sample, and (ii) the identities of said target subsequences in said nucleic acid, or the identities of said sets of target subsequences among which is included the target subsequences in said nucleic acid; searching a sequence in a nucleotide sequence database for occurrences of said target subsequences or target subsequences that are members of said sets of target subsequences, and for the length between such occurrences, said database comprising a plurality of known nucleotide sequences that may be present in said sample; matching said one or more actual signals and a sequence in said database when the sequence in said database has both (i) the same length between occurrences of target subsequences as is represented by said one or more actual signals and (ii) the same target subsequences as is represented by said one or more actual signals, or target subsequences that are members of the same sets of target subsequences as is represented by said one or more actual signals; and repetitively performing said searching and matching steps for the majority of sequences in the database and outputting those database sequences that match said one or more actual signals, or alternatively a computer readable memory for directing a programmable apparatus to function in the manner of the third object.

In a fourth embodiment, the invention provides a programmable apparatus for selecting target subsequences comprising an initial selection device for selecting initial target subsequences or initial sets of target subsequences; a first control device; a search device operatively coupled to said initial selection device and to said first control device (i) for searching sequences in a nucleotide sequence database for occurrences of said initial target subsequences or occurrences of target subsequences that are members of said initial sets of target subsequences and for the length between such occurrences and (ii) for determining an initial pattern of signals that can be generated from said selected initial target subsequences or said initial sets of target subsequences, said database comprising a plurality of known nucleotide sequences, said signals comprising a representation of (i) the length between said occurrences in a sequence in said database, and (ii) the identities of said initial target subsequences that occur in said sequence in said database, or the identities of target subsequences that are members of the same initial sets of target subsequences that occur in said sequence in said database; and an ascertaining device operatively coupled to said searching device and to said first control device for ascertaining the value of said determined initial pattern according to an information measure; and wherein said first control device causes further target subsequences to be selected and causes the search device to determine a further pattern of signals and the ascertaining device to ascertain a further value of said information measure and accepts the further target subsequences when said further pattern optimizes said further value of said information measure.

This invention further provides in the fourth object that a predetermined one or more of the sequences in said database are of interest, and wherein said ascertaining device ascertains the value of an information measure by counting the number of such sequences of interest which generate in said determined pattern at least one signal that is not generated by any other sequence in said database, and optionally that said one or more of the sequences of interest comprise substantially all the sequences in said database.

This invention further provides in the fourth embodiment that said first control device optimizes the value of said information measure according to a method of exhaustive search, wherein said first control device selects further target subsequences of length less than approximately 10 and accepts the further target subsequences if said further value of said information measure is greater than the previous value.

This invention further provides in the fourth embodiment that said first control device optimizes the value of said information measure according to a method comprising simulated annealing, wherein said first control device repeatedly selects further target subsequences and accepts the further target subsequences if said further value of said information measure is not decreased by greater than a probabilistic factor dependent on a simulated-temperature, and wherein said programmable apparatus further comprises a second control device operatively coupled to said first control device for decreasing said simulated-temperature as said first control device selects further target subsequences, and optionally wherein said probabilistic factor is an exponential function of the negative of the decrease in the information measure divided by said simulated-temperature.

This invention further provides in the fourth embodiment that the database comprises a majority of known DNA sequences that are likely to be expressed by one or more cell types.

This invention further provides in the fourth embodiment a computer readable memory that can be used to direct a programmable apparatus to function for selecting target subsequences according to steps comprising selecting initial target subsequences or initial sets of target subsequences; searching a sequence in a nucleotide sequence database for occurrences of said initial target subsequences or occurrences of target subsequences that are members of said initial sets of target subsequences and for the length between such occurrences, said database comprising a plurality of known nucleotide sequences that may be present in said sample; determining an initial pattern of signals that can be generated from said selected initial target subsequences or said initial sets of target subsequences, said signals comprising a representation of (i) the length between said occurrences in a sequence in said database, and (ii) the identities of said initial target subsequences that occur in said sequence in said database, or the identities of target subsequences that are members of the initial sets of target subsequences that occur in said sequence in said database; ascertaining the value of said determined initial pattern according to an information measure; and repetitively performing said selecting, searching, determining, and ascertaining steps to determine a further pattern of signals and a further value of said information measure, and accepting the further target subsequences when said further pattern optimizes said further value of said information measure, or alternatively a computer readable memory for directing a programmable apparatus to function in the manner of the fourth object.

In a fifth embodiment, the invention provides a programmable apparatus for displaying data comprising a selecting device for selecting target subsequences or sets of target subsequences, such that recognition means for recognizing said target subsequences or said sets of target subsequences can be used to generate signals by probing a sample comprising a plurality of nucleic acids, said signals comprising a representation of (i) the length between occurrences of said target subsequences in a nucleic acid of said sample and (ii) the identities of said target subsequences in said nucleic acid or the identities of said sets of target subsequences among which are included the target subsequences in said nucleic acid; an inputting device for inputting one or more actual signals generated by probing said sample with said recognition means; an analyzing device for analyzing signals operatively coupled to said selecting and inputting devices that determines which sequences in a nucleotide sequence database can generate said actual signals when subject to said recognition means, said database comprising a plurality of known nucleotide sequences that may be present in said sample; an input/output device operatively coupled to said selecting, inputting, and analyzing devices that inputs user requests and controls the selecting device to select target subsequences or sets of target subsequences, controls the inputting device to accept actual signals, controls the analyzing device to find the sequences in said database that can generate said actual signals, and displays output comprising said actual signals and said sequences in said database that can generate said actual signals.

This invention further provides in the fifth embodiment that said sample is a cDNA sample prepared from a tissue specimen, and the apparatus further comprises a storage device operatively coupled to the input/output device for storing indications of the origin of said tissue specimen and information concerning said tissue specimen, and wherein said indications can be displayed upon user input, and optionally that the indications and information concerning said tissue specimen comprises histological information comprising tissue images.

This invention further provides in the fifth embodiment additional apparatus further comprising one or more instrument devices for probing said sample with said recognition means and for generating said actual signals; and a control device operatively coupled to said one or more instrument devices and to said input/output device for controlling the operation of said instrument devices, wherein said user can input control commands for control of said instrument devices and receive output concerning the status of said instrument devices, and optionally wherein one or more of said selecting, inputting, analyzing, and input/output devices are physically collocated with each other, or are physically spaced apart from each other and are connected by a communication medium for exchanges of commands and information.

This invention further provides in the fifth embodiment a computer readable memory that can be used to direct a programmable apparatus to function for displaying data according to steps comprising selecting target subsequences or sets of target subsequences, such that recognition means for recognizing said target subsequences or said sets of target subsequences can be used to generate signals by probing a sample comprising a plurality of nucleic acids, said signals comprising a representation of (i) the length between occurrences of said target subsequences in a nucleic acid of said sample and (ii) the identities of said target subsequences in said nucleic acid or the identities of said sets of target subsequences among which are included the target subsequences in said nucleic acid inputting one or more actual signals generated by probing said sample with said recognition means analyzing said one or more actual signals to determine which sequences in a nucleotide sequence database can generate said actual signals when subject to said recognition means, said database comprising a plurality of known nucleotide sequences that may be present in said sample; and inputting user requests to control said selecting step to select target subsequences or sets of target subsequences, said inputting step to input actual signals, and said analyzing step to find the sequences in said database that can generate said actual signals, and outputting in response to further user requests information comprising said actual signals and said sequences in said database that can generate said actual signals, or alternatively a computer readable memory for directing a programmable apparatus to function in the manner of the fifth object.

In a sixth embodiment, the invention provides a method for identifying, classifying, or quantifying DNA molecules in a sample of DNA molecules having a plurality of different nucleotide sequences, the method comprising the steps of digesting said sample with one or more restriction endonucleases, each said restriction endonuclease recognizing a subsequence recognition site and digesting DNA at said recognition site to produce fragments with 5' overhangs; contacting said fragments with shorter and longer oligodeoxynucleotides, each said shorter oligodeoxynucleotide hybridizable with a said 5' overhang and having no terminal phosphates, each said longer oligodeoxynucleotide hybridizable with a said shorter oligodeoxynucleotide; ligating said longer oligodeoxynucleotides to said 5' overhangs on said DNA fragments to produce ligated DNA fragments; extending said ligated DNA fragments by synthesis with a DNA polymerase to produce blunt-ended double stranded DNA fragments; amplifying said blunt-ended double stranded DNA fragments by a method comprising contacting said DNA fragments with a DNA polymerase and primer oligodeoxynucleotides, each said primer oligodeoxynucleotide having a sequence comprising that of one of the longer oligodeoxynucleotides; determining the length of the amplified DNA fragments; and searching a DNA sequence database, said database comprising a plurality of known DNA sequences that may be present in the sample, for sequences matching one or more of said fragments of determined length, a sequence from said database matching a fragment of determined length when the sequence from said database comprises recognition sites of said one or more restriction endonucleases spaced apart by the determined length, whereby DNA molecules in said sample are identified, classified, or quantified.

This invention further provides in the sixth embodiment additional methods wherein the sequence of each primer oligodeoxynucleotide further comprises 3' to and contiguous with the sequence of the longer oligodeoxynucleotide the portion of the recognition site of said one or more restriction endonucleases remaining on a DNA fragment terminus after digestion, said remaining portion being 5' to and contiguous with one or more additional nucleotides, and wherein a sequence from said database matches a fragment of determined length when the sequence from said database comprises subsequences that are the recognition sites of said one or more restriction endonucleases contiguous with said one or more additional nucleotides and when the subsequences are spaced apart by the determined length.

This invention further provides in the sixth embodiment additional methods wherein said determining step further comprises detecting the amplified DNA fragments by a method comprising staining said fragments with silver.

This invention further provides in the sixth embodiment additional methods wherein said oligodeoxynucleotide primers are detectably labeled, wherein the determining step further comprises detection of said detectable labels, and wherein a sequence from said database matches a fragment of determined length when the sequence from said database comprises recognition sites of the one or more restriction endonucleases, said recognition sites being identified by the detectable labels of said oligodeoxynucleotide primers, said recognition sites being spaced apart by the determined length, and optionally wherein said determining step further comprises detecting the amplified DNA fragments by a method comprising labeling said fragments with a DNA intercalating dye or detecting light emission from a fluorochrome label on said fragments.

This invention further provides in the sixth embodiment additional steps further comprising, prior to said determining step, the step of hybridizing the amplified DNA fragments with a detectably labeled oligodeoxynucleotide complementary to a subsequence, said subsequence differing from said recognition sites of said one or more restriction endonucleases, wherein the determining step further comprises detecting said detectable label of said oligodeoxynucleotide, and wherein a sequence from said database matches a fragment of determined length when the sequence from said database further comprises said subsequence between the recognition sites of said one or more restriction endonucleases.

This invention further provides in the sixth embodiment additional methods wherein the one or more restriction endonucleases are pairs of restriction endonucleases, the pairs being selected from the group consisting of Acc56I and HindIII, Acc65I and NgoMI, BamHI and EcoRI, BglII and HindIII, BglII and NgoMI, BsiWI and BspHI, BspHI and BstYI, BspHI and NgoMI, BsrGI and EcoRI, EagI and EcoRI, EagI and HindIII, EagI and NcoI, HindIII and NgoMI, NgoMI and NheI, NgoMI and SpeI, BglII and BspHI, Bsp120I and NcoI, BssHII and NgoMI, EcoRI and HindIII, and NgoMI and XbaI, or wherein the step of ligating is performed with T4 DNA ligase.

This invention further provides in the sixth embodiment additional methods wherein the steps of digesting, contacting, and ligating are performed simultaneously in the same reaction vessel, or optionally wherein the steps of digesting, contacting, ligating, extending, and amplifying are performed in the same reaction vessel.

This invention further provides in the sixth embodiment additional methods wherein the step of determining the length is performed by electrophoresis.

This invention further provides in the sixth embodiment additional methods wherein the step of searching said DNA database further comprises determining a pattern of fragments that can be generated and for each fragment in said pattern those sequences in said DNA database that are capable of generating the fragment by simulating the steps of digesting with said one or more restriction endonucleases, contacting, ligating, extending, amplifying, and determining applied to each sequence in said DNA database; and finding the sequences that are capable of generating said one or more fragments of determined length by finding in said pattern one or more fragments that have the same length and recognition sites as said one or more fragments of determined length.

This invention further provides in the sixth embodiment additional methods wherein the steps of digesting and ligating go substantially to completion.

This invention further provides in the sixth embodiment additional methods wherein the DNA sample is cDNA prepared from mRNA, and optionally wherein the DNA is of RNA from a tissue or a cell type derived from a plant, a single celled animal, a multicellular animal, a bacterium, a virus, a fungus, a yeast, or a mammal, and optionally wherein the mammal is a human, and optionally wherein the mammal is a human having or suspected of having a diseased condition, and optionally wherein the diseased condition is a malignancy.

In a seventh embodiment, this invention provides additional methods for identifying, classifying, or quantifying DNA molecules in a sample of DNA molecules with a plurality of nucleotide sequences, the method comprising the steps of digesting said sample with one or more restriction endonucleases, each said restriction endonuclease recognizing a subsequence recognition site and digesting DNA to produce fragments with 3' overhangs; contacting said fragments with shorter and longer oligodeoxynucleotides, each said longer oligodeoxynucleotide consisting of a first and second contiguous portion, said first portion being a 3' end subsequence complementary to the overhang produced by one of said restriction endonucleases, each said shorter oligodeoxynucleotide complementary to the 3' end of said second portion of said longer oligodeoxynucleotide stand; ligating said longer oligodeoxynucleotide to said DNA fragments to produce a ligated fragment; extending said ligated DNA fragments by synthesis with a DNA polymerase to form blunt-ended double stranded DNA fragments; amplifying said double stranded DNA fragments by use of a DNA polymerase and primer oligodeoxynucleotides to produce amplified DNA fragments, each said primer oligodeoxynucleotide having a sequence comprising that of a longer oligodeoxynucleotides; determining the length of the amplified DNA fragments; and searching a DNA sequence database, said database comprising a plurality of known DNA sequences that may be present in the sample, for sequences matching one or more of said fragments of determined length, a sequence from said database matching a fragment of determined length when the sequence from said database comprises recognition sites of said one or more restriction endonucleases spaced apart by the determined length, whereby DNA sequences in said sample are identified, classified, or quantified.

In an eighth embodiment, this invention provides additional methods of detecting one or more differentially expressed genes in an in vitro cell exposed to an exogenous factor relative to an in vitro cell not exposed to said exogenous factor comprising performing the methods the first embodiment of this invention wherein said plurality of nucleic acids comprises cDNA of RNA of said in vitro cell exposed to said exogenous factor; performing the methods of the first embodiment of this invention wherein said plurality of nucleic acids comprises cDNA of RNA of said in vitro cell not exposed to said exogenous factor; and comparing the identified, classified, or quantified cDNA of said in vitro cell exposed to said exogenous factor with the identified, classified, or quantified cDNA of said in vitro cell not exposed to said exogenous factor, whereby differentially expressed genes are identified, classified, or quantified.

In a ninth embodiment, this invention provides additional methods of detecting one or more differentially expressed genes in a diseased tissue relative to a tissue not having said disease comprising performing the methods of the first embodiment of this invention wherein said plurality of nucleic acids comprises cDNA of RNA of said diseased tissue such that one or more cDNA molecules are identified, classified, and/or quantified; performing the methods of the first embodiment of this invention wherein said plurality of nucleic acids comprises cDNA of RNA of said tissue not having said disease such that one or more cDNA molecules are identified, classified, and/or quantified; and comparing said identified, classified, and/or quantified cDNA molecules of said diseased tissue with said identified, classified, and/or quantified cDNA molecules of said tissue not having the disease, whereby differentially expressed cDNA molecules are detected.

This invention further provides in the ninth embodiment additional methods wherein the step of comparing further comprises finding cDNA molecules which are reproducibly expressed in said diseased tissue or in said tissue not having the disease and further finding which of said reproducibly expressed cDNA molecules have significant differences in expression between the tissue having said disease and the tissue not having said disease, and optionally wherein said finding cDNA molecules which are reproducibly expressed and said significant differences in expression of said cDNA molecules in said diseased tissue and in said tissue not having the disease are determined by a method comprising applying statistical measures, and optionally wherein said statistical measures comprise determining reproducible expression if the standard deviation of the level of quantified expression of a cDNA molecule in said diseased tissue or said tissue not having the disease is less than the average level of quantified expression of said cDNA molecule in said diseased tissue or said tissue not having the disease, respectively, and wherein a cDNA molecule has significant differences in expression if the sum of the standard deviation of the level of quantified expression of said cDNA molecule in said diseased tissue plus the standard deviation of the level of quantified expression of said cDNA molecule in said tissue not having the disease is less than the absolute value of the difference of the level of quantified expression of said cDNA molecule in said diseased tissue minus the level of quantified expression of said cDNA molecule in said tissue not having the disease.

This invention further provides in the ninth embodiment additional methods wherein the diseased tissue and the tissue not having the disease are from one or more mammals, and optionally wherein the disease is a malignancy, and optionally wherein the disease is a malignancy selected from the group consisting of prostate cancer, breast cancer, colon cancer, lung cancer, skin cancer, lymphoma, and leukemia.

This invention further provides in the ninth embodiment additional methods wherein the disease is a malignancy and the tissue not having the disease has a premalignant character.

In a tenth embodiment, this invention provides methods of staging or grading a disease in a human individual comprising performing the methods of the first embodiment of this invention in which said plurality of nucleic acids comprises cDNA of RNA prepared from a tissue from said human individual, said tissue having or suspected of having said disease, whereby one or more said cDNA molecules are identified, classified, and/or quantified; and comparing said one or more identified, classified, and/or quantified cDNA molecules in said tissue to the one or more identified, classified, and/or quantified cDNA molecules expected at a particular stage or grade of said disease.

In an eleventh embodiment, this invention provides additional methods for predicting a human patient's response to therapy for a disease, comprising performing the methods of the first embodiment of this invention in which said plurality of nucleic acids comprises cDNA of RNA prepared from a tissue from said human patient, said tissue having or suspected of having said disease, whereby one or more cDNA molecules in said sample are identified, classified, and/or quantified; and ascertaining if the one or more cDNA molecules thereby identified, classified, and/or quantified correlates with a poor or a favorable response to one or more therapies, and optionally which further comprises selecting one or more therapies for said patient for which said identified, classified, and/or quantified cDNA molecules correlates with a favorable response.

In a twelfth embodiment, this invention provides additional methods for evaluating the efficacy of a therapy in a mammal having a disease, the method comprising performing the methods of the first embodiment of this invention wherein said plurality of nucleic acids comprises cDNA of RNA of said mammal prior to a therapy; performing the method of the first embodiment of this invention wherein said plurality of nucleic acids comprises cDNA of RNA of said mammal subsequent to said therapy; comparing one or more identified, classified, and/or quantified cDNA molecules in said mammal prior to said therapy with one or more identified, classified, and/or quantified cDNA molecules of said mammal subsequent to therapy; and determining whether the response to therapy is favorable or unfavorable according to whether any differences in the one or more identified, classified, and/or quantified cDNA molecules after therapy are correlated with regression or progression, respectively, of the disease, and optionally wherein the mammal is a human.

In a thirteenth embodiment, this invention provides a kit comprising one or more containers having one or more restriction endonucleases; one or more containers having one or more shorter oligodeoxynucleotide strands; one or more containers having one or more longer oligodeoxynucleotide strands hybridizable with said shorter strands, wherein either the longer or the shorter oligodeoxynucleotide strands each comprise a sequence complementary to an overhang produced by at least one of said one or more restriction endonucleases; and instructions packaged in association with said one or more containers for use of said restriction endonucleases, shorter strands, and longer strands for identifying, classifying, or quantifying one or more DNA molecules in a DNA sample, said instructions comprising (i) digest said sample with said restriction endonucleases into fragments, each fragment being terminated on each end by a recognition site of said one or more restriction endonucleases; (ii) contact said shorter and longer strands and said digested fragments to form double stranded DNA adapters annealed to said digested fragments, (iii) ligate said longer strand to said fragments; (iv) generate one or more signals by separating and detecting such of said fragments that are digested on each end, each signal comprising a representation of the length of the fragment and the identity of the recognition sites on both termini of the fragments; and (v) search a nucleotide sequence database to determine sequences that match or the absence of any sequences that match said one or more generated signals, said database comprising a plurality of known nucleotide sequences of nucleic acids that may be present in the sample, a sequence from said database matching a generated signal when the sequence from said database has both (i) the same length between occurrences of said recognition sites of said one or more restriction endonucleases as is represented by the generated signal and (ii) the same recognition sites of said one of more restriction endonucleases as is represented by the generated signal.

This invention further provides in the thirteenth embodiment a kit wherein said one or more restriction endonucleases generate 5' overhangs at the terminus of digested fragments, wherein each said shorter oligodeoxynucleotide strand consists of a first and second contiguous portion, said first portion being a 5' end subsequence complementary to the overhang produced by one of said restriction endonucleases, and wherein each said longer oligodeoxynucleotide strand comprises a 3' end subsequence complementary to said second portion of said shorter oligodeoxynucleotide strand, or optionally wherein said one or more restriction endonucleases generate 3' overhangs at the terminus of the digested fragments, wherein each said longer oligodeoxynucleotide strand consists of a first and second contiguous portion, said first portion being a 3' end subsequence complementary to the overhang produced by one of said restriction endonucleases, and wherein each said shorter oligodeoxynucleotide strand is complementary to the 3' end of said second portion of said longer oligodeoxynucleotide stand.

This invention further provides in the thirteenth embodiment a kit wherein said instructions further comprise those signals expected from one or more DNA molecules of interest when said sample is digested with a particular one or more restriction endonucleases selected from among said one or more restriction endonucleases in said kit, and optionally wherein said one or more DNA molecules of interest are cDNA molecules differentially expressed in a disease condition.

This invention further provides in the thirteenth embodiment a kit wherein the restriction endonucleases are selected from the group consisting of Acc65I, AflIII, AgeI, ApaLI, ApoI, AscI, AvrI, BamHI, BclI, BglII, BsiWI, Bsp120I, BspEI, BspHI, BsrGI, BssHII, BstYI, EagI, EcoRI, HindIII, MluI, NcoI, NgoMI, NheI, NotI, SpeI, and XbaI.

This invention further provides in the thirteenth embodiment a kit further comprising one or more containers having one or more double stranded adapter DNA molecules formed by annealing said longer and said shorter oligonucleotide strands.

This invention further provides in the thirteenth embodiment a kit further comprising the computer readable memory of claim 106, or optionally further comprising the computer readable memory of claim 114, or optionally further comprising the computer readable memory of claim 122.

This invention further provides in the thirteenth embodiment a kit further comprising in a container a DNA ligase, or optionally further comprising in a container a phosphatase capable of removing terminal phosphates from a DNA sequence.

This invention further provides in the thirteenth embodiment a kit further comprising one or more primers, each said primer consisting of a single stranded oligodeoxynucleotide comprising the sequence of one of said longer strands; and a DNA polymerase, and optionally wherein each of said one or more primers further comprises (a) a first subsequence that is the portion of the recognition site of one of said one or more restriction endonucleases remaining at the terminus of a fragment after digestion, and (b) a second subsequence of one or two additional nucleotides contiguous with and 3' to said first subsequence, wherein said primer is detectably labeled such that primers with differing said one or two additional nucleotides have different labels that can be distinguishably detected.

This invention further provides in the thirteenth embodiment a kit wherein said instructions further comprise: detect such of said fragments digested on each end by a method comprising staining said fragments with silver, labeling said fragments with a DNA intercalating dye, or detecting light emission from a fluorochrome label on said fragments.

This invention further provides in the thirteenth embodiment a kit further comprising reagents for performing a cDNA sample preparation step; reagents for performing a step of digestion by one or more restriction endonucleases; reagents for performing a ligation step; and reagents for performing a PCR amplification step.

4. BRIEF DESCRIPTION OF THE DRAWINGS

These and other features, aspects, and advantages of the present invention will become better understood by reference to the accompanying drawings, following description, and appended claims, where:

FIG. 1 shows exemplary results of the signals generated by the QEA method of this invention;

FIGS. 2A, 2B, and 2C show DNA adapters for an RE/ligation implementation of the QEA method of this invention, where the restriction endonucleases generate 5' overhangs, open blocks indicating strands of DNA;

FIGS. 3A and 3B show the DNA adapters for an RE/ligation implementation of the QEA method of this invention, where the restriction endonucleases generate 3' overhangs;

FIGS. 4A, 4B, and 4C show an exemplary biotin alternative embodiment of the QEA method;

FIGS. 8A and 8B show an overview of a method for determining a simulated database of experimental results for the QEA embodiment of this invention;

Figure 9:
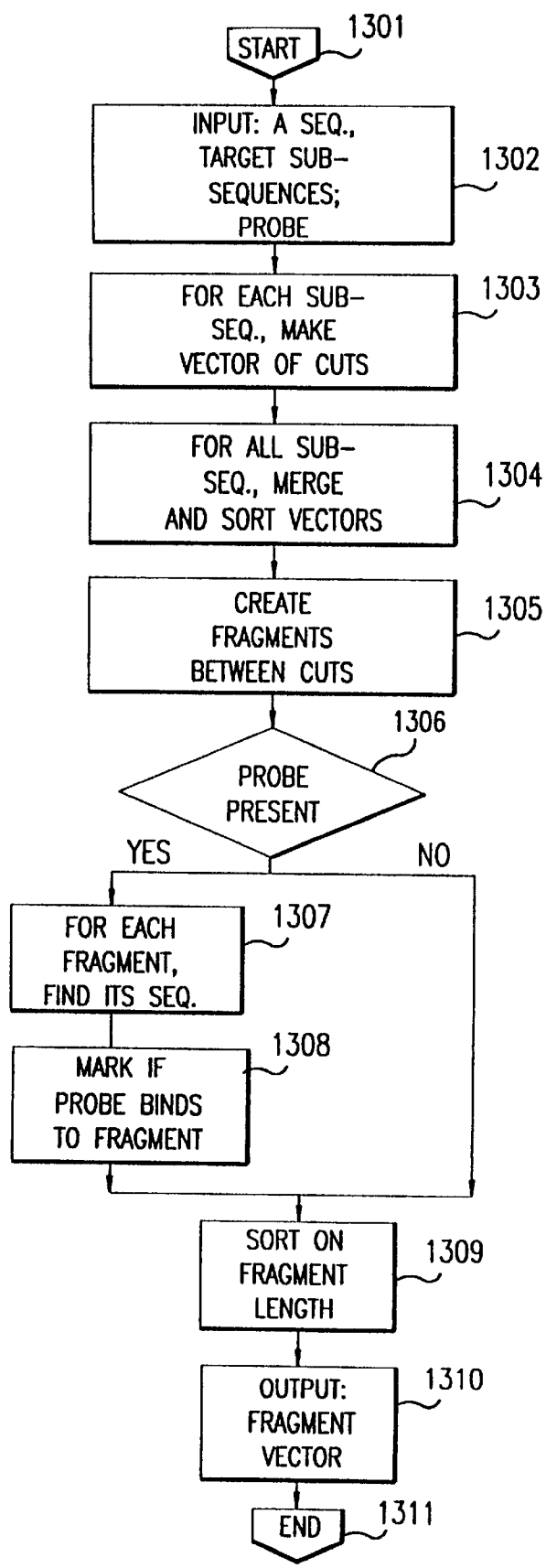
FIG. 9 shows the detail of a method for simulating a QEA reaction.
Figure 11:
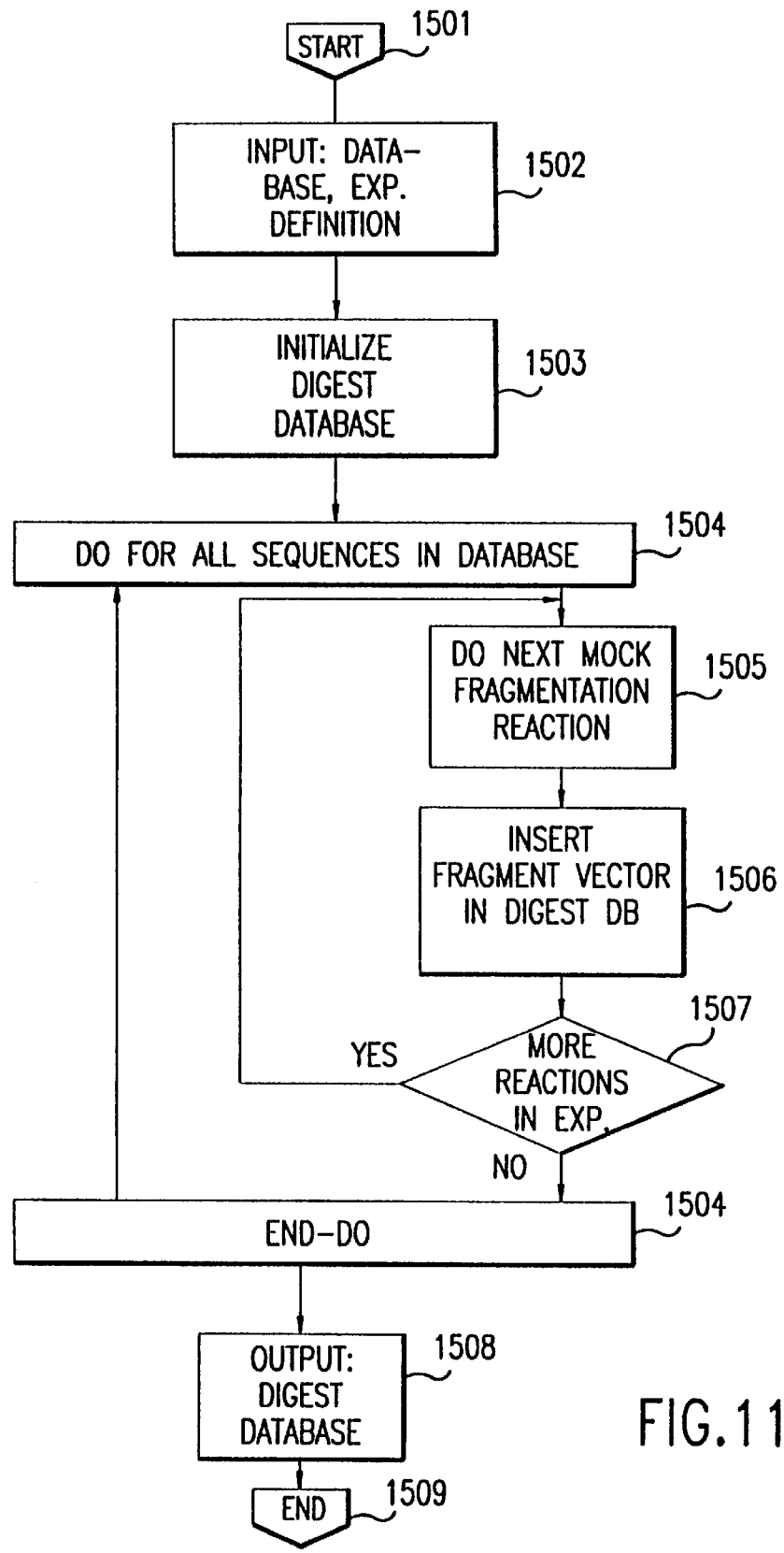
Figure 12A:
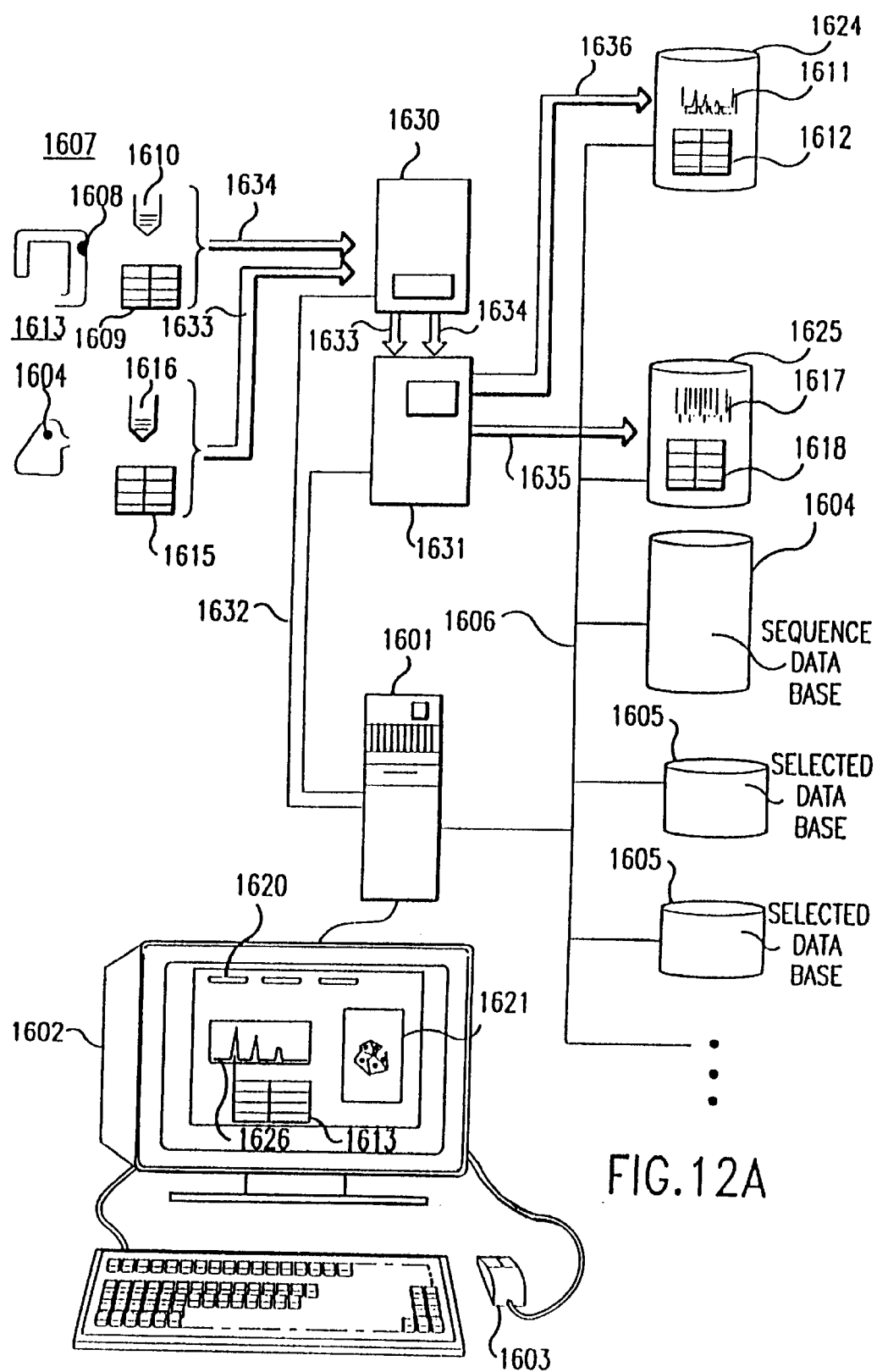
Figure 12B:
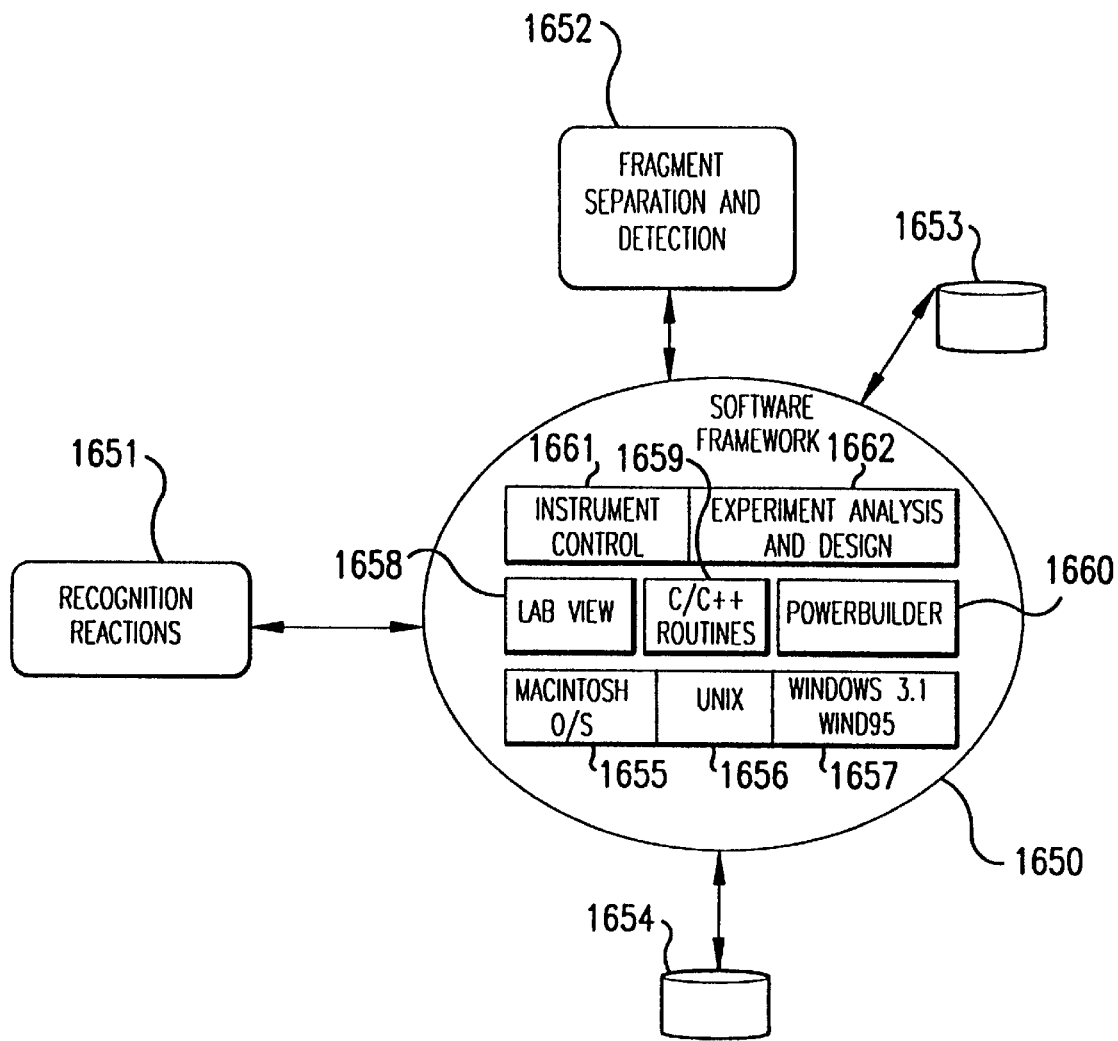
Figure 12C:
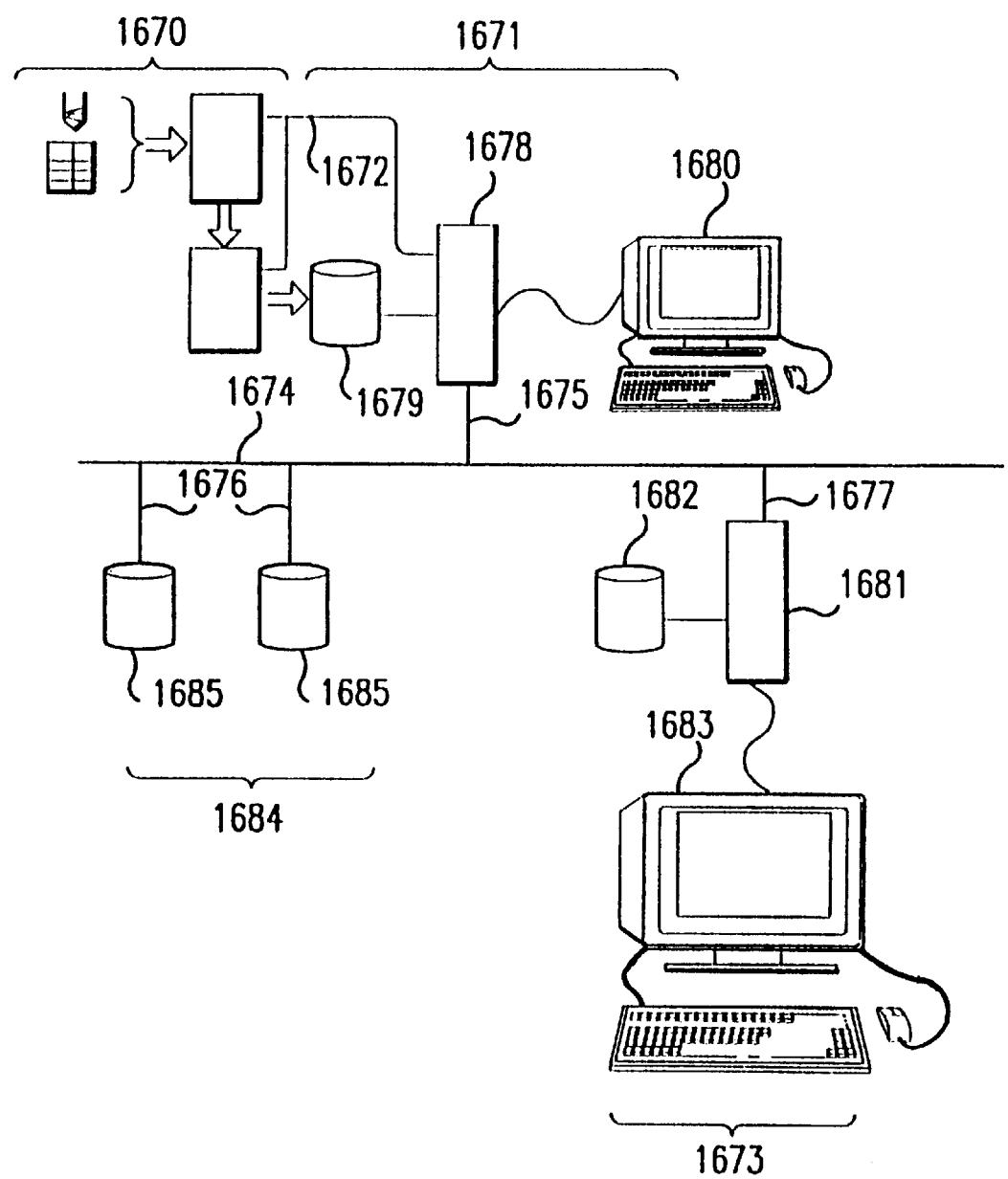
Figure 13A:
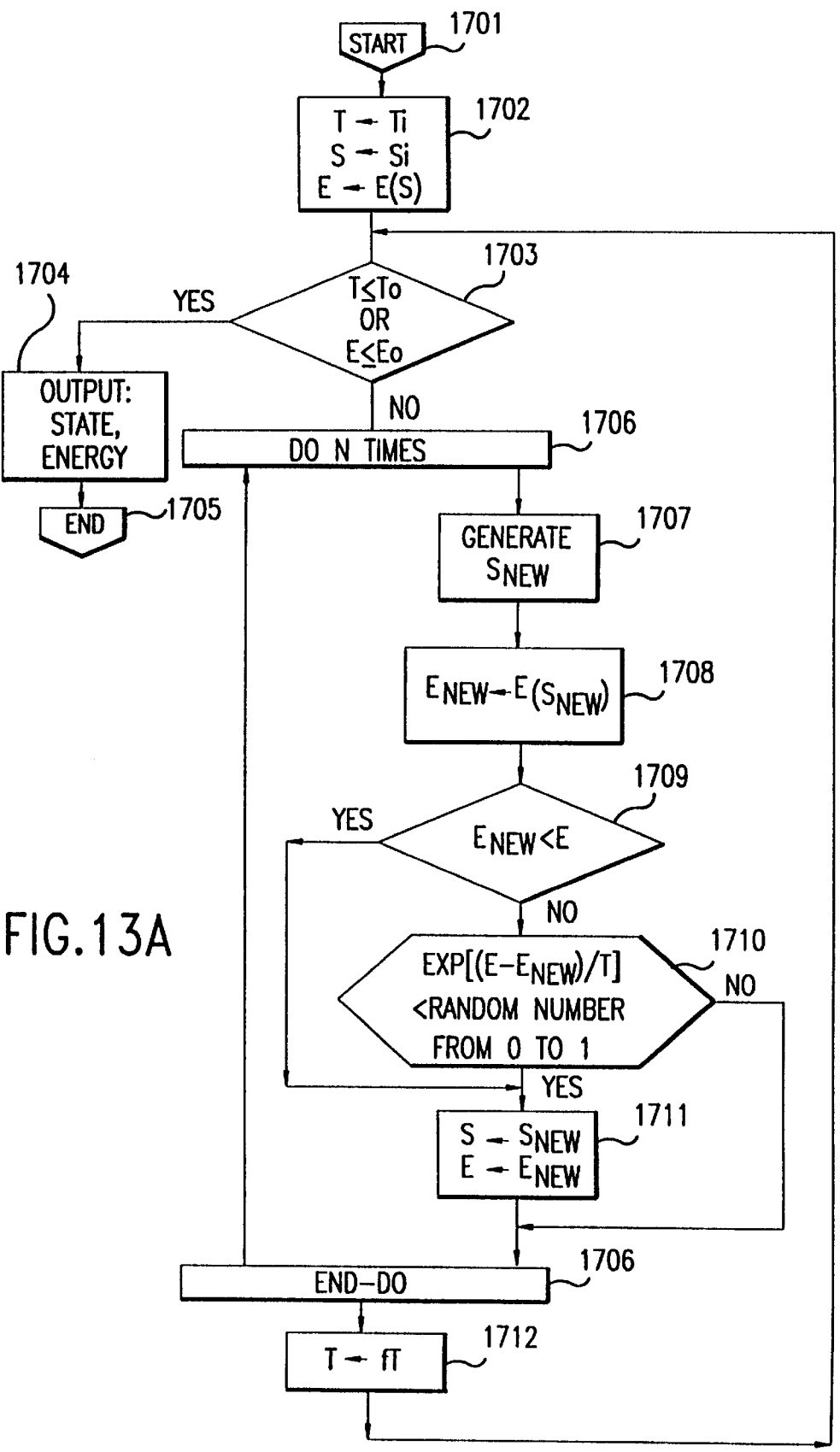
Figure 13B:
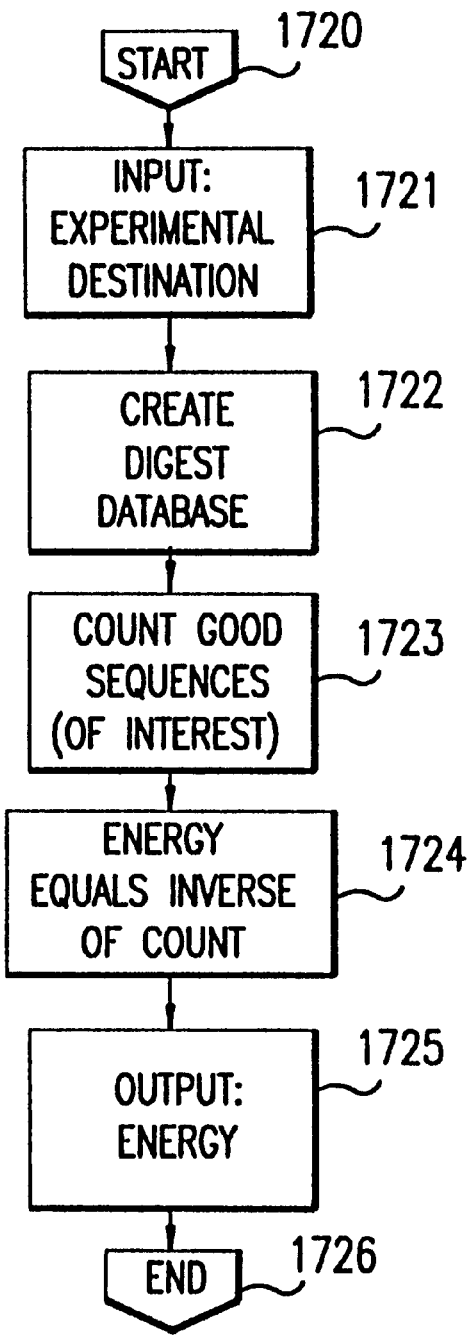
Figure 14:
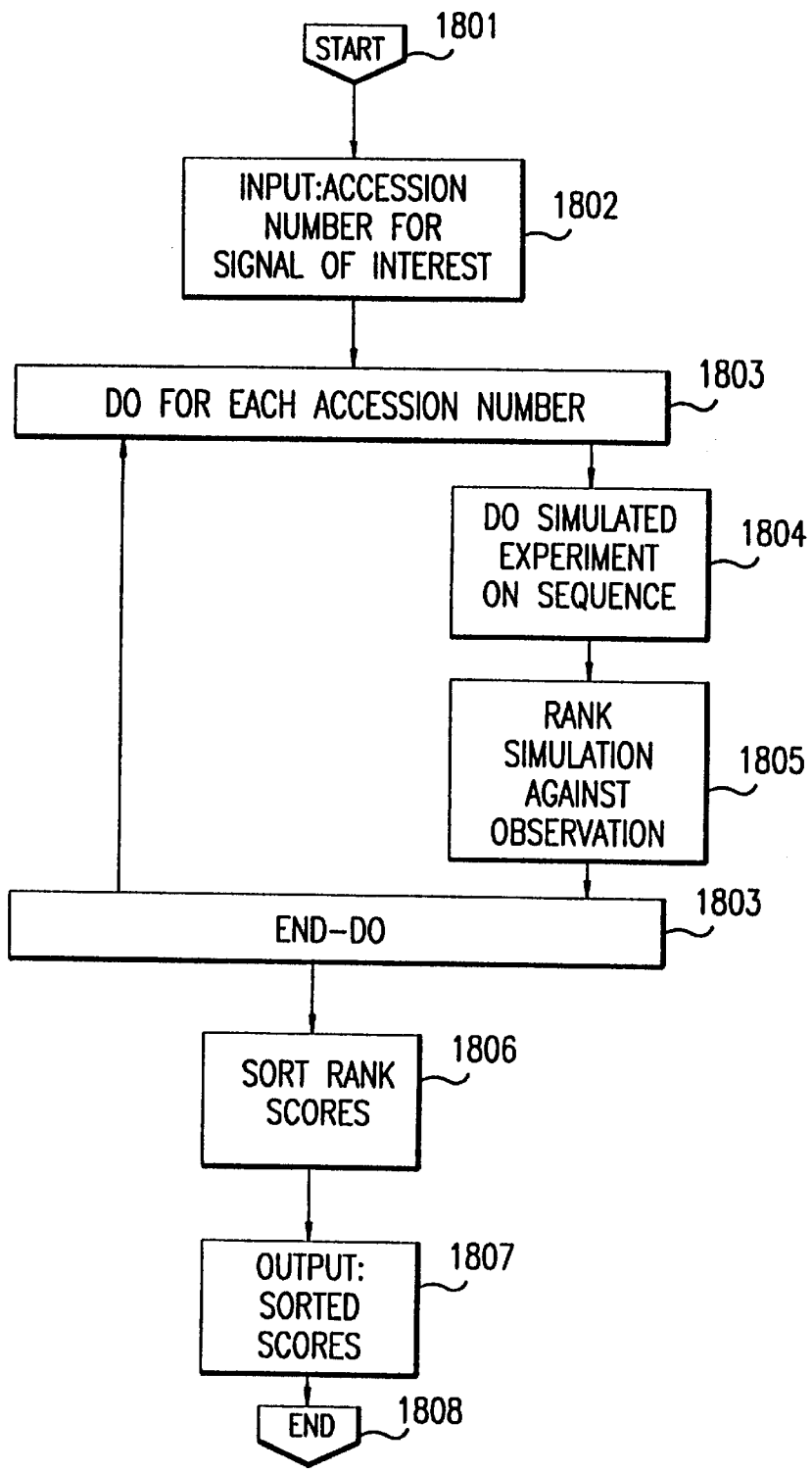
Figure 15:
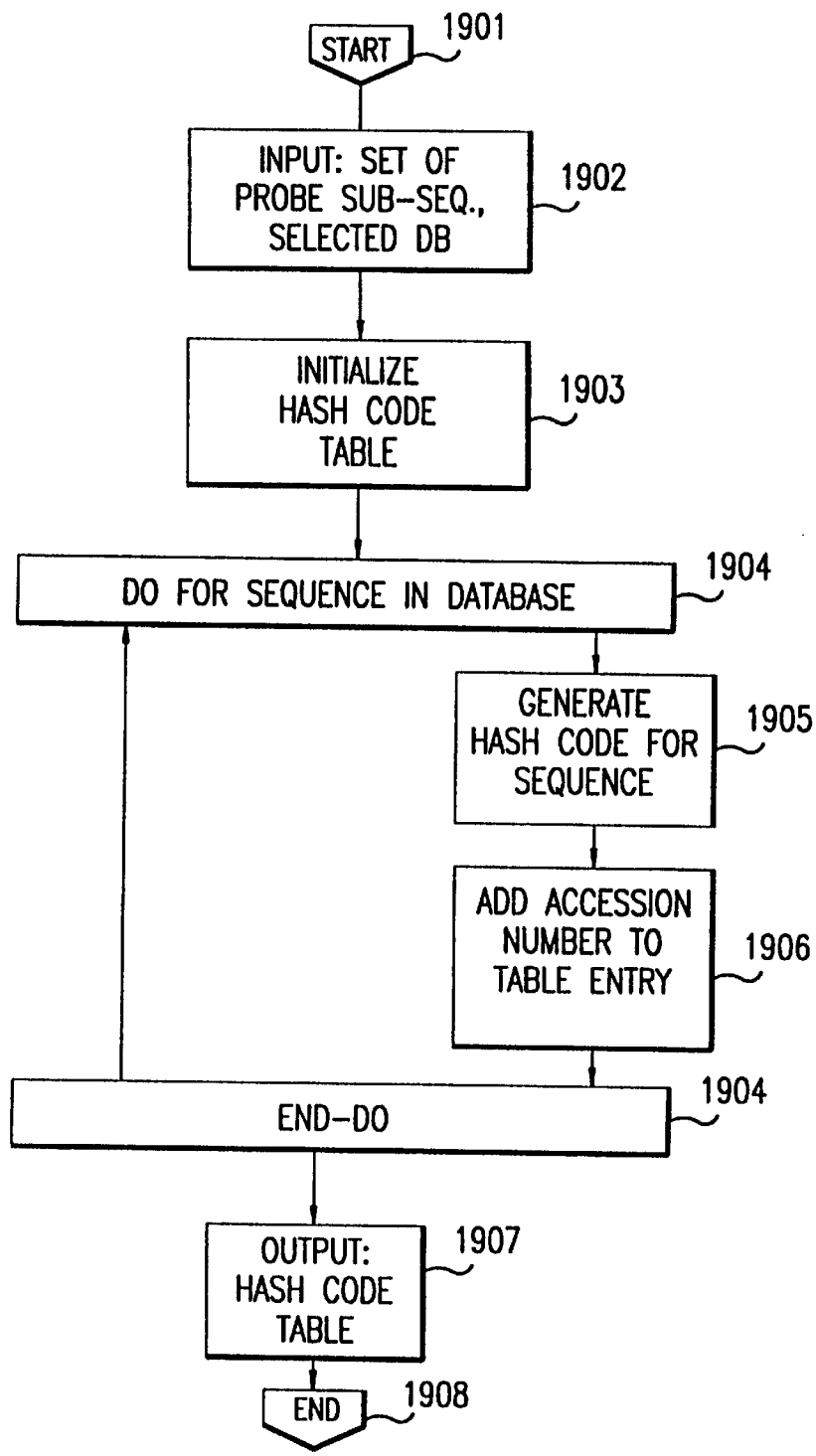

FIGS. 10A–F show exemplary results of the action of the method of FIG. 9;

FIG. 11 shows the detail of a method for determining a simulated database of experimental results for a QEA embodiment of this invention;

FIGS. 12A, 12B, and 12C show an exemplary computer system apparatus, and an alternative embodiment, implementing methods of this invention;

FIG. 13A shows exemplary detail of an experimental design method for QEA and CC embodiments of this invention and FIG. 13B shows exemplary detail of an experimental design method for a QEA embodiment of this invention;

FIG. 14 shows an exemplary method for ordering the DNA sequences found to be likely causes of a QEA signal in the order of their likely presence in the sample;

FIG. 15 shows the detail of a method for determining a simulated database of experimental results for a CC embodiment of this invention;

FIGS. 16A, 16B, 16C, and 16D show exemplary reaction temperature profiles for preferred manual and automated implementations of a preferred RE embodiment of a QEA method.

5. DETAILED DESCRIPTION

According to the present invention, to uniquely identify an expressed gene sequence, full or partial, and many components of genomic DNA it is not necessary to determine actual, complete nucleotide sequences of samples. Full sequences provide far more information than is needed to merely classify or determine a gene according to the invention. For example, in the human genome, it is known that there are approximately $10^5$ expressed genes. Since the average length of a coding sequence is approximately 2000 nucleotides, the total number of possible sequences is approximately $4^{2000}$, or about $10^{1200}$. The actual number of expressed human genes is an unimaginably small fraction ($10^{-1195}$) of the total number of possible DNA sequences. Even sequencing a 50 bp fragment of a cDNA sequence generates about $10^{25}$ times more information than is needed for classification of that sequence. Use of the present invention allows direct classification of expressed gene sequences with far less information than either a complete or a partial sequence determination of a sample.

In computer science, codes which compactly identify a few members from among a large set of possibilities are called hash codes. An object of this invention is to construct hash codes for expressed DNA sequences, or alternatively for any other existing set of DNA sequences. In a fully populated code without any unassigned code words, all human genes could be coded by an approximately 17 bit binary number ($2^{17}=1.3\times10^5$). A 20 bit code would be about 10% filled or 90% sparse ($2^{20}=1.0\times10^6$).

In this invention codes are constructed from signals which represent the presence of short nucleic acid (preferably DNA) subsequences (hereinafter called "target subsequences") in the sample sequence and, preferably, in a QEA embodiment, include a representation of the length along the sample sequence between adjacent target subsequences. The presence of these subsequences is recognized by subsequence recognition means, including, but not limited to, REs, DNA binding proteins, and oligomers ("probes") hybridizable to DNA of, for example, PNAs or DNAS. The subsequence recognition means allow recognition of specific DNA subsequences by the ability to specifically bind to or react with such subsequences. The invention, and particularly its computer methods, are adaptable to any subsequence recognition means available in the art. Acceptable subsequence detection means preferably precisely and reproducibly recognize target subsequences and generate a recognition signal of adequate signal to noise ratio for all genes, however rare, in a sample, and can also provide information on the length between target subsequences.

The signals contain representations of target subsequence occurrences and, preferably, a representation of the length between target subsequence occurrences. In various embodiments of this invention these representations may differ. In embodiments where the target subsequences are exactly recognized, as where REs are used, subsequence representation may simply be the actual identity of the subsequences. In other embodiments where subsequence recognition is less exact, as where short oligomers are used, this representation may be "fuzzy". It may, for example, consist of all subsequences which differ by one nucleotide from the target, or some other set of possible subsequences, perhaps weighted by the probability that each member of the set is the actual subsequence in the sample sequence. Further, the length representation may depend on the separation and detection means used to generate the signals. In the case of electrophoretic separation, the length observed electrophoretically may need to be corrected, perhaps up to 5 to 10%, for mobility differences due to average base composition differences or due to effects of any labeling moiety used for detection. As these corrections may not be known until target sequence recognition, the signal may contain the electrophoretic length in bp and not the true physical length in bp. For simplicity and without limitation, in most of the following description unless otherwise noted the signals are presumed to represent the information conveyed exactly, as if generated by exact recognition means and error or bias free separation and detection means. However, in particular embodiments, target subsequences may be represented in a fuzzy fashion and length, if present, with separation and detection bias present.

Target subsequences recognized are typically of contiguous sequence. This is required for all known REs. However, oligomers recognizing discontinuous subsequences can be used and can be constructed by inserting degenerate nucleotides in any discontinuous region. For example, a set of 16 oligomers recognizing AGC--TAT, with a two nucleotide skip between the two portions of the recognition subsequence, could be constructed as TCGNNATA, where N is any nucleotide. Alternately, such discontiguous subsequences can be recognized by one oligomer of the form TCGiiATA, where "i" is inosine, or any other "universal" nucleotide, capable of hybridizing with any naturally occurring base.

This invention is adaptable to analyzing any DNA sample for which exists an accompanying database listing possible sequences in the sample. More generally, the invention is adaptable to analyzing the sequences of any biopolymer, built of a small number of repeating units, whose naturally occurring representatives are far fewer that the number of possible, physical polymers and in which small subsequences can be recognized. Thus it is applicable to not only naturally occurring DNA polymers but also to naturally occurring RNA polymers, proteins, glycans, etc. Typically and without limitation, however, the invention is applied to the analysis of cDNA samples from any in vivo or in vitro sources. cDNA can be synthesized either from total cellular RNA or from specific sub-pools of RNA. These RNA sub-pools can be produced by RNA pre-purification, for example, the separation of mRNA of the endoplasmic reticulum from cytoplasmic mRNA, which thereby enriches mRNA primarily encoding for cell surface or extracellular proteins (Celis et al., 1994, Cell Biology, Academic Press, New York, N.Y.). Such enriched mRNAs have increased diagnostic or therapeutic utility due to their encoded protein's cell-surface or extracellular roles, such as being a receptor. Such pre-purified RNA pools can be used in all embodiments of this invention.

First strand cDNA synthesis can use any priming method known in the art, for example, oligo(dT) primers, random hexamer primers, phasing primers, mixtures thereof, etc. Phasing primers, containing either an A,C, or G at the 3' end, can be used in separate cDNA synthesis reactions to split the cDNA first strands into 3 pools, each generated from poly (A) RNA having a T, G, or C, respectively, 5' to the poly(A) tail. Fifteen mixtures can be synthesized by using all 15 possible oligo(dT) primers containing a pair of non-T nucleotides at the 3' end.

Two specific embodiments of the invention are respectively termed "quantitative expression analysis" ("QEA") and "colony calling" ("CC").

The specific embodiment, QEA, probes a sample with recognition means, the recognition means generating signals, a preferred signal being a triple comprising an indication of the presence of a first target subsequence, an indication of the presence of a second target subsequence, and a representation of the length between the target subsequences in the sample nucleic acids sequence. Each pair of target subsequences may occur more than once in a sample nucleic acid, in which case the associated lengths are between adjacent target subsequence occurrences.

The QEA embodiment is preferred for classifying and determining sequences in cDNA mixtures, but is also adaptable to samples with only one sequence. It is preferred for mixtures because it affords the relative advantage over prior art methods that cloning of sample nucleic acids is not required. Typically, enough distinguishable signals are generated from pairs of target subsequences to recognize a desired sequence in a sample mixture. For example, first, any pair of target subsequences may hit more than once in a single DNA molecule to be analyzed, thereby generating several signals with differing lengths from one DNA molecule. Second, even if the pair of target subsequences hits only once in two different DNA molecules to be analyzed, the lengths between the hits may differ and thus distinguishable signals may be generated.

The target subsequences used in QEA are preferably optimally chosen by methods of this invention from DNA sequence databases containing sequences likely to occur in the sample to be analyzed. Efforts of the Human Genome Project in the United States, efforts abroad, and efforts of private companies in the sequencing of the human genome sequences, both expressed and genetic, are being collected in several available databases (listed in § 5.1).

In a QEA "query mode" experiment, the focus is on determining the expression of several genes, perhaps 1–100, of interest and of known sequence. A minimal number of target subsequences is chosen to generate signals, with the goal that each of the several genes is discriminated by at least one unique signal, which also discriminates it from all the other genes likely to occur in the sample. In other words, the experiment is designed so that each gene generates at least one signal unique to it (a "good" gene, see infra). In a QEA "tissue mode" experiment, the focus is on determining the expression of as many as possible, preferably a majority, of the genes in a tissue, without the need for any prior knowledge or interest in their expression. Target subsequences are optimally chosen to discriminate the maximum number of sample DNA sequences into classes comprising one or preferably at most a few sequences. Signals are generated and detected as determined by the threshold and sensitivity of a particular experiment. Some important determinants of threshold and sensitivity are the initial amount of mRNA and thus of cDNA, the amount of molecular amplification performed during the experiment, and the sensitivity of the detection means. Preferably, enough signals are produced and detected so that the computer methods of this invention can uniquely determine the expression of a majority, or more preferably most, of the genes expressed in a tissue.

QEA signals are generated by methods utilizing recognition means that include, but are not limited to REs in a preferred RE/ligase method or in a method utilizing a removal means, preferably contacting streptavidin linked to a solid phase with biotin-labeled DNA, for removal of unwanted DNA fragments, and nucleotide oligomer primers in a PCR method.

A preferred embodiment of the RE/ligase method is as follows. The method employs recognition reactions with a pair (or more) of REs which recognize target subsequences with high specificity and cut the sequence at the recognition sites leaving fragments with sticky ends characteristic of the particular RE. To each sticky end, special primers are ligated which are distinctively labeled with fluorochromes identifying the particular RE making the cut, and thus the particular target subsequence. A DNA polymerase is used to form blunt-ended DNA fragments. The labeled fragments are then PCR amplified using the same special primers a number of times preferably just sufficient to detect signals from all sequences of interest while making relatively small signals from the linearly amplifying singly cut fragments. The amplified fragments are then separated by length using gel electrophoresis, and the length and labeling of the fragments is optically detected. Optionally, single stranded fragments can be removed by a binding hydroxyapatite, or other single strand specific, column or by digestion by a single strand specific nuclease. Also, this invention is adaptable to other functionally equivalent amplification and length separation means. In this manner, the identity of the REs cutting a fragment, and thereby the subsequences present, as well as the length between the cuts is determined.

In a preferred PCR method for QEA, a suitable collection of target subsequences is chosen by the computer implemented QEA experimental design methods and PCR primers distinctively labeled with fluorochromes are synthesized to hybridize with these subsequences. The primers are designed as described in § 5.3 to reliably recognize short subsequences while achieving a high specificity in PCR amplification. Using these primers, a minimum number of PCR amplification steps amplifies those fragments between the primed subsequences existing in DNA sequences in the sample. The labeled, amplified fragments are separated by gel electrophoresis and detected.

In an exemplary QEA method utilizing a removal means, which has improved quantitative characteristics and is also adapted to highly sensitive detection systems, cDNA is synthesized from a tissue sample using at least one internally biotinylated primer. The cDNA is then cyclized, cut with a pair of REs, and specifically labeled primers are ligated to the cut ends, as discussed in § 5.2.2. The singly cut ends attached to the biotinylated synthesis primers are removed with streptavidin or avidin beads leaving highly pure labeled double cut cDNA fragments without any singly cut and labeled background fragments. With a sufficiently sensitive optical detection system, these pure doubly cut and labeled fragments can be separated by length (e.g. by electrophoresis or column chromatography) and directly detected without amplification. If amplification is needed, absence of the DNA singly cut fragment background improves signal to noise ratio permitting fewer amplification steps and, thereby, decreased PCR amplification bias.

Optional alternatives can provide increased discrimination in QEA experiments. Two sequences producing two fragments of identical end subsequences and length can be discriminated by recognizing a third subsequence present in one of the fragments but not in the other. In one alternative, a labeled probe recognizing this third subsequence can be added before detection to generate unique signals from the fragment containing that subsequence. In another alternative, a probe can be added before amplification which prevents amplification of the fragment with the third subsequence and which thereby removes (suppresses) its signal. By way of example, such a probe can be either an RE for recognizing and cutting the fragment with the third subsequence or a PNA, or modified DNA, probe which will hybridize with the third subsequence and prevent its PCR amplification.

The signals generated from the recognition reactions of a QEA experiment are analyzed by computer methods of this invention. The analysis methods simulate a QEA experiment using a database either of substantially all known DNA sequences or of substantially all, or at least a majority of, the DNA sequences likely to be present in a sample to be analyzed and a description of the reactions to be performed. The simulation results in a digest database which contains for all possible signals that can be generated the sample sequences responsible. Thereby, finding the sequences that can generate a signal involves a look-up in the simulated digest database. Computer implemented design methods optimize the choice of target subsequences in the QEA reactions in order to maximize the information produced in an experiment. For the tissue mode, the methods maximize the number of sequences having unique signals by which their quantitative presence can be unambiguously determined. For the query mode, the methods maximize only the number of sequences of interest having unique signals, ignoring other sequences that might be present in a sample.

A second specific embodiment, colony calling ("CC"), generates subsequence hit data without length information. Since this method requires only hybridizations, it is preferred for gene identification in arrayed single-sequence clones constructed from a tissue library. This embodiment constructs a binary code in which each bit of the code represents the presence or absence of one target subsequence. By probing four to eight target subsequences in parallel, such as by using distinguishable fluorescent labeling of the multiple probes, in view of the adequacy of a 20 bit code, the presence or absence of any expressed human gene should be determinable in just three to five separate probe steps. Such a compact method with such economy in signal generation is highly useful. Alternatively, recent real time hybridization detection methods (Stimson et al., 1995, Proc. Natl. Acad. Sci. USA, 92:6379–6383) based on optical wave guides can be used for detection. These methods make hybridization detection more efficient both by eliminating the washing step otherwise needed between hybridization and detection and by speeding up the detection step.

The hash code generated by the probe hybridization reactions is interpreted by computer implemented methods of this invention. The analysis methods simulate a CC experiment using a list of the target subsequences and a database of the DNA sequences likely to be present in a sample to be analyzed. The simulation results in a hash code table which contains for each hash code all possible sequences that can generate that code. Thereby, interpretation of a detected hash code requires a look-up in the table to find the possible sequences.

It is preferable that subsequences be carefully chosen in order that a minimum set of targets be obtained, preferably no more than approximately 20, that produce the maximum amount of information. Computer implemented methods of this invention determine optimum sets of target subsequences for a given database of sequences likely to occur in the sample by optimizing the number of non-empty hash codes in the simulated hash code table.

Maximum information is obtained when the target subsequences occur completely randomly in the possible sample sequences, that is, when their likelihood of occurrence is approximately 50% and the presence of one subsequence is independent of the presence of any other subsequence. Therefore, target subsequences chosen to generate a signal should preferably occur in the DNA sequence sample to be analyzed less than about 50% and at least more often than 5–10%, preferably more often than 10–15%. The most preferable occurrence probability is from 25–50%. Also the presence of one target subsequence is preferably probabilistically independent of the presence of any other subsequence.

Using data on expressed RNA from human DNA sequence databases, this means that sub-sequences are preferably less than about 5 to 8 bp long for cDNA classification. Typically, the resulting preferable target subsequences are 4 to 6 bp long. Longer sequences occur too infrequently to be preferred for use. However, for classifying gDNA, longer subsequences, up to 20 to 40 bp, are preferably used, because gDNA fragments are normally of much greater length, from at least 5 kilobases ("kb") for plasmid inserts to more the 100 kb for P1 inserts, and thus would typically have more sequence variability, requiring longer target subsequences.

The preferred hybridization probes for short target subsequences are labeled peptido-nucleic acids (PNAs). Alternatively sets of degenerate, longer DNA oligonucleotides are used which include as a common subsequence the target subsequence. These degenerate sets achieve improved hybridization specificity as compared to 4 to 6-mers. Sets of probes, each probe distinctively and distinguishably labeled with a fluorochrome, are hybridized in conditions of high stringency to arrayed DNA sequence clones and optically detected to detect the presence of target subsequences. For example, in an embodiment wherein five fluorochromes are simultaneously distinguished and 20 subsequences observations are required for gene identification (a 20 bit code), any gene in a colony can be identified in only four hybridization steps. Alternately, efficient hybridization detection means based on optical wave guide detection of DNA hybridization can be used. By using differently sized and shaped particles associated with different probes, the resultant differences in light scattering can be used to detect hybridization of multiple probes simultaneously with these wave guide methods.

Target subsequences can be chosen to discriminate not only single genes but also, more coarsely, sets of genes. Fewer target subsequences can be chosen so that a particular pattern of hits will indicate the presence of a gene of a particular type. Types of genes of interest might be oncogenes, tumor suppressor genes, growth factors, cell cycle genes, or cytoskeletal genes, etc.

In embodiments of this invention where high stringency hybridization are specified, such conditions generally comprise a low salt concentration, equivalent to a concentration of SSC (173.5 g. NaCl, 88.2 g. Na Citrate, $H_2O$ to 1 l.) of less than approximately 1 mM, and a temperature near or above the $T_m$ of the hybridizing DNA. In contrast, conditions of low stringency generally comprise a high salt concentration, equivalent to a concentration of SSC of greater than approximately 150 mM, and a temperature below the $T_m$ of the hybridizing DNA.

In embodiments of this invention where DNA oligomers are specified for performing functions, including hybridization and chain elongation priming, alternatively oligomers can be used that comprise those of the following nucleotide mimics which perform similar functions. Nucleotide mimics are subunits (other than classical nucleotides) which can be polymerized to form molecules capable of specific, Watson-Crick-like base pairing with DNA. The oligomers can be DNA or RNA or chimeric mixtures or derivatives or modified versions thereof. The oligomers can be modified at the base moiety, sugar moiety, or phosphate backbone. The oligomers may include other appending groups such as peptides, hybridization-triggered cleavage agents (see, e.g., Krol et al., 1988, BioTechniques 6:958–976), or intercalating agents (see, e.g., Zon, 1988, Pharm. Res. 5:539–549). The oligomers may be conjugated to another molecule, e.g., a peptide, hybridization triggered cross-linking agent, transport agent, hybridization-triggered cleavage agent, etc.

The oligomers may also comprise at least one nucleotide mimic that is a modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylgueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. The oligomers may comprise at least one modified sugar moiety selected from the group including but not limited to arabinose, 2-fluoroarabinose, xylulose, and hexose. The oligomers may comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The oligomer may be an α-anomeric oligomer. An α-anomeric oligomer forms specific double-stranded hybrids with complementary RNA in which, contrary to the usual β-units, the strands run parallel to each other (Gautier et al., 1987, Nucl. Acids Res. 15:6625–6641).

Oligomers of the invention may be synthesized by standard methods known in the art, e.g. by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. U.S.A. 85:7448–7451), etc.

In specific embodiments of this invention it is preferable to use oligomers that can specifically hybridize to subsequences of a DNA sequence too short to achieve reliably specific recognition, such that a set of target subsequences is recognized. Further where PCR is used, as Taq polymerase tolerates hybridization mismatches, PCR specificity is generally less than hybridization specificity. Where such oligomers recognizing short subsequences are preferable, they may be constructed in manners including but not limited to the following. To achieve reliable hybridization to shorter DNA subsequences, degenerate sets of DNA oligomers may be used which are constructed of a total length sufficient to achieve specific hybridization with each member of the set containing a shorter sequence complementary to the common subsequence to be recognized. Alternatively, a longer DNA oligomer may be constructed with a shorter sequence complementary to the subsequence to be recognized and with additional universal nucleotides or nucleotide mimics, which are capable of hybridizing to any naturally occurring nucleotide. Nucleotide mimics are sub-units which can be polymerized to form molecules capable of specific, Watson-Crick-like base pairing with DNA. Alternatively, the oligomers may be constructed from DNA mimics which have improved hybridization energetics compared to naturally occurring nucleotides.

A preferred mimic is a peptido-nucleic acid ("PNA") based on a linked N-(2-aminoethyl)glycine backbone to which normal DNA bases have been attached (Egholm et al., 1993, Nature, 365:566–67). This PNA obeys specific Watson-Crick base pairing but with greater free energy of binding and correspondingly higher melting temperatures. Suitable oligomers may be constructed entirely from PNAs or from mixed PNA and DNA oligomers.

In embodiments of this invention where DNA fragments are separated by length, any length separation means known in the art can be used. One alternative separation means employs a sieving medium for separation by fragment length coupled with a force for propelling the DNA fragments though the sieving medium. The sieving medium can be a polymer or gel, such a polyacrylamide or agarose in suitable concentrations to separate 10–1000 bp DNA fragments. In this case the propelling force is a voltage applied across the medium. The gel can be disposed in electrophoretic configurations comprising thick or thin plates or capillaries. The gel can be non-denaturing or denaturing. Alternately, the sieving medium can be such as used for chromatographic separation, in which case a pressure is the propelling force. Standard or high performance liquid chromatographic ("HPLC") length separation means may be used. An alternative separation means employs molecular characteristics such as charge, mass, or charge to mass ratio. Mass spectrographic means capable of separating 10–1000 bp fragments may be used.

DNA fragment lengths determined by such a separation means represent the physical length in base pairs between target subsequences, after adjustment for biases or errors introduced by the separation means and length changes due to experimental variables (e.g., presence of a detectable label, ligation to an adopter molecule). A represented length is the same as the physical length between occurrences of target subsequences in a sequence from said database when both said lengths are equal after applying corrections for biases and errors in said separation means and corrections based on experimental variables. For example, represented lengths determined by electrophoresis can be adjusted for mobility biases due to average base composition or mobility changes due to an attached labeling moiety and/or adapter strand by conventional software programs, such as Gene Scan Software from Applied Biosystems, Inc. (Foster City, Calif.).

In embodiments of this invention where DNA fragments must be labeled and detected, any compatible labeling and detection means known in the art can be used. Advances in fluorochromes, in optics, and in optical sensing now permit multiply labeled DNA fragments to be distinguished even if they completely overlap in space, as in a spot on a filter or a band in a gel. Results of several recognition reactions or hybridizations can be multiplexed in the same gel lane or filter spot. Fluorochromes are available for DNA labeling which permit distinguishing 6–8 separate products simultaneously (Ju et al., 1995, Proc. Natl. Acad Sci. USA, 92:4347–4351).

Exemplary fluorochromes adaptable to this invention and methods of using such fluorochromes to label DNA are described in § 6.10.

Single molecule detection by fluorescence is now becoming possible (Eigen et al., 1994, Proc. Natl. Acad Sci. USA, 91:5740–5747), and can be adapted for use.

In embodiments of this invention where intercalating DNA dyes are utilized to detect DNA, any such dye known in the art is adaptable. In particular such dyes include but are not limited to ethidium bromide, propidium iodide, Hoechst 33258, Hoechst 33342, acridine orange, and ethidium bromide homodimers. Such dyes also include POPO, BOBO, YOYO, and TOTO from Molecular Probes (Eugene, Oreg.).

Finally alternative sensitive detection means available include silver staining of polyacrylamide gels (Bassam et al., 1991, Analytic Biochemistry, 196:80–83), and the use of intercalating dyes. In this case the gel can be photographed and the photograph scanned by scanner devices conventional in the computer art to produce a computer record of the separated and detected fragments. A further alternative is to blot an electrophoretic separating gel onto a filter (e.g., nitrocellulose) and then to apply any visualization means known in the art to visualize adherent DNA. See, e.g., Kricka et al., 1995, Molecular Probing, Blotting, and Sequencing, Academic Press, New York. In particular, visualization means requiring secondary reactions with one or more reagents or enzymes can be used, as can any means employed in the CC embodiment.

A preferred separation and detection apparatus for use in this invention is found in copending U.S. patent application Ser. No. 08/438,231 filed May 9, 1995, which is hereby incorporated by reference in its entirety. Other detection means adaptable to this invention include the commercial electrophoresis machines from Applied Biosystems Inc. (Foster City, Calif.), Pharmacia (ALF), Hitachi, Licor. The Applied Biosystems machine is preferred among these as it is the only machine capable of simultaneous 4 dye resolution.

In the following subsections and the accompanying examples sections the QEA and the CC embodiments are described in detail.

5.1. QUANTITATIVE EXPRESSION ANALYSIS

This embodiment preferably generates one or more signals unique to each cDNA sequence in a mixture of cDNAs, such as may be derived from total cellular RNA or total cellular mRNA from a tissue sample, and to quantitatively relate the strength of such a signal or signals to the relative amount of that cDNA sequence in the sample or library. Less preferably, the signals uniquely determine only sets of a small number of sequences, typically 2–10 sequences. QEA signals comprise an indication of the presence of pairs of target subsequences and the length between pairs of adjacent subsequences in a DNA sample. Signals are generated in a manner permitting straightforward automation with existing laboratory robots. For simplicity of disclosure, and not by way of limitation, the detailed description of this method is directed to the analysis of samples comprising a plurality of cDNA sequences. It is equally applicable to samples comprising a single sequence or samples comprising sequences of other types of DNA or nucleic acids generally.

While described in terms of cDNA hereinbelow, it will be understood that the DNA sample can be cDNA and/or genomic DNA, and preferably comprises a mixture of DNA sequences. In specific embodiments, the DNA sample is an aliquot of cDNA of total cellular RNA or total cellular mRNA, most preferably derived from human tissue. The human tissue can be diseased or normal. In one embodiment, the human tissue is malignant tissue, e.g., from prostate cancer, breast cancer, colon cancer, lung cancer, lymphatic or hematopoietic cancers, etc. In another embodiment, the tissue may be derived from in vivo animal models of disease or other biologic processes. In this cases the diseases modeled can usefully include, as well as cancers, diabetes, obesity, the rheumatoid or autoimmune diseases, etc. In yet another embodiment, the samples can be derived from in vitro cultures and models. This invention can also be advantageously applied to examine gene expression in plants, yeasts, fungi, etc.

The cDNA, or the mRNA from which it is synthesized, must be present at some threshold level in order to generate signals, this level being determined to some degree by the conditions of a particular QEA experiment. For example, such a threshold is that preferably at least 1000, and more preferably at least 10,000, mRNA molecules of the sequence to be detected be present in a sample. In the case where one or only a few mRNAs of a type of interest are present in each cell of a tissue from which it is desired to derive the sample mRNA, at least a corresponding number of such cells should be present in the initial tissue sample. In a specific embodiment, the mRNA detected is present in a ratio to total sample RNA of $1:10^5$ to $1:10^6$. With a lower ratio, more molecular amplification can be performed during a QEA experiment.

The cDNA sequences occurring in a tissue derived pool include short untranslated sequences and translated protein coding sequences, which, in turn, may be a complete protein coding sequence or some initial portion of a coding sequence, such as an expressed sequence tag. A coding sequence may represent an as yet unknown sequence or gene or an already known sequence or gene entered into a DNA sequence database. Exemplary sequence databases include those made available by the National Center for Biotechnology Information ("NCBI") (Bethesda, Md.) (GenBank) and by the European Bioinformatics Institute ("EMBL") (Hinxton Hall, UK).

The QEA method is also applicable to samples of genomic DNA in a manner similar to its application to cDNA. In gDNA samples, information of interest includes occurrence and identity of translocations, gene amplifications, loss of heterozygosity for an allele, etc. This information is of interest in cancer diagnosis and staging. In cancer patients, amplified sequences might reflect an oncogene, while loss of heterozygosity might reflect a tumor suppressor gene. Such sequences of interest can be used to select target subsequences and to predict signals generated by a QEA experiment. Even without prior knowledge of the sequences of interest, detection and classification of QEA signal patterns is useful for the comparison of normal and diseased states or for observing the progression of a disease state. Gene expression information concerning the progression of a disease state is useful in order to elucidate the genetic mechanisms behind disease, to find useful diagnostic markers, to guide the selection and observe the results of therapies, etc. Signal differences identify the gene or genes involved, whether already known or yet to be sequenced.

Classification of QEA signal patterns, in an exemplary embodiment, can involve statistical analysis to determine significant differences between patterns of interest. This can involve first grouping samples that are similar in one or more characteristics, such characteristics including, for example, epidemiological history, histopathological state, treatment history, etc. Signal patterns from similar samples are then compared, e.g., by finding the average and standard deviation of each individual signals. Individual signal which are of limited variability, for which the standard deviation is less than the average, then represent genetic constants of samples of this particular characteristic. Such limited variability signals from one set of tissue samples can then be compared to limited variability signals from another set of tissue samples. Signals which differ in this comparison then represent significant differences in the genetic expression between the tissue samples and are of interest in reflecting the biological differences between the samples, such as the differences caused by the progression of a disease. For example, a significant difference in expression is detected with the difference in the genetic expression between two tissues exceed the sum of the standard deviation of the expressions in the tissues. Other standard statistical comparisons can also be used to establish level of expression and the significance of differences in levels of expressions.

Target subsequence choice is important in the practice of this invention. The two primary considerations for selecting subsequences are, first, redundancy, that is, that there be enough subsequence pair hits per gene that a unique signal is likely to be generated for each sample sequence, and second, resolution, that is, that there not be so many primer pairs hitting with very similar lengths in a sample that the signals cannot be discriminated. For sufficient redundancy, it is preferable that there be on average, approximately three pair hits per gene or DNA sequence in the sample. It is highly preferable that there be at least one pair hit per each gene In test of a database of eukaryotic expressed sequences, it has been found that an average value of three hits per gene appears to be generally a sufficient guarantee of this minimum criterion.

Sufficient resolution depends on the separation and detection means chosen. For a particular choice of separation and detection means, a recognition reaction preferably should not generate more fragments than can be separated and distinguishably detected. In a preferred embodiment, gel electrophoresis is the separation means used to separate DNA fragments by length. Existing electrophoretic techniques allow an effective resolution of three base pair ("bp") length differences in sequences of up to 1000 bp length. Given knowledge of fragment base composition, effective resolution down to 1 bp is possible by predicting and correcting for the small differences in mobility due to differing base composition. However and without limitation, an easily achievable three bp resolution is assumed by way of example in the description of the invention herein. It is preferable for increased detection efficiency that the distinguishably labeled products from as many recognition reactions as possible be combined for separation in one gel lane. This combination is limited by the number of labels distinguishable by the employed detection means. Any alternative means for separation and detection of DNA fragments by length, preferably with resolution of three bp or better, can be employed. For example, such separation means can be thick or thin plate or column electrophoresis, column chromatography or HPLC, or physical means such as mass spectroscopy.

The redundancy and resolution criteria are probabilistically expressed in Eqns. 1 and 2 in an approximation adequate to guide subsequence choice. In these equations the number of genes in the cDNA sequence mixture is N, the average gene length is L, the number of target subsequence pairs is M (the number of pairs of recognition means), and the probability of each target subsequence hitting a typical gene is p. Since each target subsequences is preferably selected to independently hit each pooled sequence, the probability of an arbitrary subsequence pair hitting is then $p^2$. Eqn. 1 expresses the redundancy condition of three hits per gene, assuming the probabilities of target subsequence hits are independent.

$$Mp^2 = 3 \quad (1)$$

Eqn 2 expresses the resolution condition of having fragments with lengths no closer on average than 3 base pairs. This equation approximates the actual fragment length distribution with a uniform distribution.

$$\frac{L}{Np^2} = 3 \quad (2)$$

Given expected values of N, the number of sequences in the library or pool to analyze (library complexity), and L, the average expressed sequence (or gene) length, Eqns 1 and 2 are solved for the subsequence hit probability and number of subsequences required. This solution depends on the particular redundancy and resolution criteria dictated by the particular experimental method chosen to implement QEA. Alternative values may be required for other implementations of this embodiment.

For example, it is estimated that the entire human genome contains approximately $10^5$ protein coding sequences with an average length of 2000. The solution of Eqns 1 and 2 for these parameters is p=0.082 and M=450. Thereby the gene expression of all genes in all human tissues can be analyzed with 450 target subsequence pairs, each subsequence having an independent probability of occurrence of 8.2%. In an embodiment in which eight fluorescently labeled subsequence pairs can be optically distinguished and detected per electrophoresis lane, such as is possible when using the separation and detection apparatus described in copending U.S. patent application Ser. No. 08/438,231 filed May 9, 1995, 450 reactions can be analyzed in only 57 lanes. Thereby only one electrophoresis plate is needed in order to completely determine all human genome expression levels. Since the best commercial machines known to the applicants can discriminate only four fluorescent labels in one lane, a corresponding increase in the number of lanes is required to perform a complete genome analysis with such machines.

As a further example, it is estimated that a typically complex human tissue expresses approximately 15,000 genes. The solution for N=15000 and L=2000 is p=0.21 and M=68. Thus expression in a typical tissue can be analyzed with 68 target subsequence pairs, each subsequence having an independent probability of occurrence of 21%. Assuming 4 subsequence pairs can be run per gel electrophoresis lane, the 68 reactions can be analyzed in 17 lanes in order to determine the gene expression frequencies in any human tissue. Thus it is clear that this method leads to greatly simplified quantitative gene expression analysis within the capabilities of existing electrophoretic systems.

These equations provide an adequate guide to picking subsequence pairs. Typically, preferred probabilities of target subsequence occurrence are from approximately 0.01 to 0.30. Probabilities of occurrence of subsequences and RE recognition sites can be determined from databases of DNA sample sequences. Example 6.2 lists these probabilities for exemplified RE recognition sites. Appropriate target subsequences can be selected from these tables. Computer implemented QEA experimental design methods can then optimize this initial selection.

Another use of QEA is to compare directly the expression of only a few genes, typically 1 to 10, between two different tissues, the query mode, instead of seeking to determine the expression of all genes in a tissue, the tissue mode. In this query mode, a few target subsequences are selected to identify the genes of interest both among themselves and from all other sequences possibly present. The computer design methods described hereinbelow can make this selection. If 4 subsequence pairs are sufficient for identification, then the fragments from the 4 recognition reactions performed on each tissue are preferably separated and detected on two separate lanes in the same gel. If 2 subsequence pairs are sufficient for identification, the two tissues are preferably analyzed in the same gel lane. Such comparison of signals from the same gel improves quantitative results by eliminating measurement variability due to differences between separate electrophoretic runs. For example, expression of a few target genes in diseased and normal tissue samples can be rapidly and reliably analyzed.

The query mode of QEA is also useful even if the sequences of the particular genes of interest are not yet known. For example, fluorescent traces produced by subjecting separate samples to gel electrophoretic separation means and then fluorescent detection means are compared to identify feature differences. Such differentially expressed features created in a particular recognition reaction are then retrieved from the gel by methods known in the art (e.g. electro-elution from the gel) and their contained DNA fragments are analyzed by conventional techniques, such as by sequencing. If partial, such sequences can then be used as probes (e.g. in PCR or Southern blot hybridization) to recover full-length sequences. In this manner, QEA techniques can guide the discovery of new differentially expressed cDNA or of changes of the state of gDNA. The sequences of the newly identified genes, once determined, can then be used to guide QEA target subsequence choice for further analysis of the differential expression of the new genes.

Three specific embodiments of the QEA method are described herein. These embodiments differ in how probing is performed by recognition means to recognize the selected target subsequences. There are also certain secondary consequential differences in how the signals are generated from the recognition means. For the PCR implementation of the QEA method, the target subsequences are recognized by oligomers which hybridize to a DNA sequence to be analyzed and act as PCR primers for the amplification of the segments between adjacent primer pairs. Amplified fragments from a sample are preferably separated by electrophoresis. Selection of target subsequences, or primer binding sites, meeting the probability of occurrence and independence criteria is preferably made from a database containing sequences expected to be present in the samples to be analyzed, for example human GenBank sequences, and optimized by the experimental design methods. Subsequence selection begins by compiling oligomer frequency tables containing the frequencies of, preferably, all 4 to 8-mers by using a sequence database. From these tables, target subsequences with the necessary probabilities of occurrence are selected and checked for independence, by, for example, checking that the conditional probability for a hit by any selected pair of subsequences is the product of the probabilities of the individual subsequence hit probabilities. The initial choice can be optimized to determine target subsequence sets producing unique fragments from the greatest number of genes, that is so that each sequence uniquely produces at least one signal. PCR primers are synthesized with a 3' end complementary to the chosen subsequences and used in the PCR embodiment. Example 6.1 illustrates the signals output by this method in a specific example.

The other two specific embodiments described herein use REs to recognize and cleave target subsequences in the sample DNA. In one implementation, the desired doubly cut fragments are amplified by an amplification means in order to dilute remaining, unwanted singly cut fragments. Alternatively, the singly cut fragments are removed by physical means (e.g. hydroxyapatite column separation) or enzymatic means (e.g. single strand specific nucleases). In another implementation, the unwanted singly cut ends are removed by a removal means from the desired doubly cut fragments without an amplification step, as described in § 5.2.2. For these implementations, RE recognition sites define the possible target subsequences and are selected in a manner similar to the above in order to meet the previous probability or occurrence and independence criteria. The probabilities of occurrence of various RE recognition sites are determined from a database of potential sample sequences, and those REs are chosen with recognition sequences whose probabilities of occurrence meet the criterion of Eqns 1 and 2 as closely as possible. If multiple REs satisfy the selection criteria, a subset is selected by including only those REs with independently occurring recognition sequences, determined, for example in the previous manner using conditional probabilities. An initial choice can be optionally optimized by the computer implemented experimental design methods.

A number, $R_e$, of REs are preferably selected so that the number of RE pairs is approximately M, where the relation between M and $R_e$ is given by Eqn 3.

$$M = \frac{R_e(R_e + 1)}{2} \quad (3)$$

For example, a set a set of 20 acceptable REs results in 210 subsequence pairs.

There are numerous REs currently available whose recognition sequences have a wide range of occurrence probabilities, from which REs can be selected for the present invention. A sample of these are presented in Example 6.2.

The PCR and the RE embodiments have different accuracy and flexibility characteristics. The RE embodiments are generally more accurate, with fewer false positive and negative identifications, since the RE/ligase recognition reaction is generally more specific than the hybridization of PCR primers to their short subsequence targets, even under stringent hybridization conditions.

Restriction endonucleases ("RE") generally bind with specificity only to their short four to eight bp recognition sites, cleaving the DNA preferably with 4 bp complementary sequences. It is preferable that REs used in this embodiment produce overhangs characteristic of the particular RE. Thus REs, such as those known as class IIS restriction enzymes, which produce overhangs of unknown sequence are less preferable. Further, ligases, which are used in an embodiment of the invention to ligate an adapter strand to a digested terminus, are highly specific in their hybridization requirements; even one bp mismatch near the ligation site will prevent ligation (U.S. Pat. No. 5,366,877, Nov. 22, 1994, to Keith et al.; U.S. Pat. No. 5,093,245, Mar. 3, 1992, to Keith et al.). PCR and the preferred Taq polymerase used therein tolerates hybridization mismatches of elongation primers. Thus the PCR embodiments may generate false positive signals which arise for mismatches in the hybridization of the oligomer probes with target subsequences.

However, the PCR embodiments are more flexible since any desired subsequences can be targets, while the RE embodiments are limited to the recognition sequences of acceptable REs. However, more than 150 to 200 REs are now commercially available recognizing a wide variety of nucleotide sequences.

QEA experiments are also adaptable to distinguish sequences into small sets, typically comprising 2 to 10 sequences, which require fewer target subsequence pairs. Such coarser grain analysis of gene expression or genomic composition requires fewer recognition reactions and analysis time. Alternatively, smaller numbers of target subsequence pairs can be optimally chosen to distinguish individually a specific set of genes of interest from all the other genes in the sample. These target subsequences can be chosen either from REs that produce fragments from the desired genes or, in the case of the PCR embodiment, from a more complete set of subsequences optimized for this smaller set of DNA sequences.

Detailed descriptions of exemplary implementations for practicing the QEA recognition reactions and the computer implemented experimental analysis and design methods are presented in the following subsections followed by detailed experimental protocols in Examples subsections. The implementations are illustrative and not limiting, as this embodiment of the invention may be practiced by any method generating the previously described QEA signals.

5.2. RE EMBODIMENTS OF QEA

The restriction endonuclease ("RE") embodiments of the QEA method use novel implementations of simultaneous RE and ligase enzymatic reactions for generating labeled fragments of the genes or sequences to be analyzed. These fragments are then separated by length by a separation means and detected by a detection means to yield QEA signals comprising the identity of the REs cutting each fragment together with each fragment's length. The recognition reactions can specifically and reproducibly generate QEA signals with good signal to noise ratios and without any intermediate extractions or buffer exchanges, which would hinder automatic execution.

REs bind with specificity to short DNA target subsequences, usually 4 to 8 bp long, that are termed recognition sites and are characteristic of each RE. REs that are used cut the sequence at (or near) these recognition sites preferably producing characteristic ("sticky") ends with single-stranded overhangs, which usually incorporate part of the recognition site.

Preferred REs have a 6 bp recognition site and generate a 4 bp 5' overhang. The RE embodiments are also adaptable to a 2 bp 5' overhang, which is less preferred since 2 bp overhangs have a lower ligase substrate activity than 4 bp overhangs. All RE embodiments can be adapted to 3' overhangs of two and four bp. Further preferred REs have the following additional properties. Their recognition sites and overhang sequences are preferably such that an adapter can be designed whose ligation does not recreate the recognition site. They preferably have sufficient activity below 37° C. and are heat inactivated at 65° C. Heat inactivation is preferable so that RE inactivation can be performed prior to adding PCR reagents and conducting the PCR reaction in the same vial. They preferably have low non-specific cutting and nuclease activities and cut to completion. Of course, REs selected for a particular experiment preferably have recognition sites meeting the previously described occurrence and independence criteria.

Preferred pair of REs for analyzing human and mouse cDNA are listed on § 6.9.

Only doubly cut sequence fragments are of interest, and thus in all RE QEA embodiments the desired doubly cut fragments are distinguished from the unwanted singly cut fragments. Singly cut fragments have a non-specific and non-reproducible length distribution derived from the distribution of overall cDNA lengths, which depends strongly on cDNA synthesis conditions. Only the doubly cut fragments have a specific and reproducible length distribution dependent only on the DNA sequence analyzed and independent of cDNA synthesis conditions. To make this distinction, the preferred RE embodiment of QEA exponentially amplifies doubly cut fragments, so that their signals quickly overwhelm signals from singly cut fragments, which are at most linearly amplified. PCR is the preferred amplification means.

Alternative amplification means known in the art are adaptable to this invention. If a removal means for singly cut ends is not utilized in an embodiment, alternative amplification means must preferentially amplify doubly cut ends over singly cut ends in order that signals from singly cut ends be relatively suppressed. On the other hand, if a removal means for singly cut ends is utilized in an embodiment, then alternative amplification means need have no amplification preference, as no singly cut ends are present at the amplification step. Known alternative amplification means are listed in Kricka et al., 1995, Molecular Probing, Blotting, and Sequencing, chap. 1 and table IX, Academic Press, New York. Of these alternative means, those employing the T7 RNA polymerase are preferred.

The other two specific embodiments use a physical removal means to directly remove singly cut fragments, preferably before amplification. This can be accomplished, e.g., by labeling DNA termini with a capture moiety prior to digestion. After digestion, the singly cut fragments are removed by contacting the sample with a binding partner of the capture moiety, affixed to a solid phase. The preferred removal means is biotin-streptavidin. Other removal means adaptable to this invention include various haptens, which are removed by their corresponding antibodies. Exemplary haptens include digoxigenin, DNP, and fluorescein (Holtke et al., 1992, Sensitive chemiluminescent detection of digoxigenin labeled nucleic acids: a fast and simple protocol for applications, Biotechniques, 12(1):104–113 and Olesen et al., 1993, Chemiluminescent DNA sequencing with multiple labeling, Biotechniques, 15(3):480–485). Alternately, single stranded fragments can be removed by single stand specific column separation or single strand specific nucleases.

RE embodiments of QEA use recognition moieties which are specifically ligated to RE cut sticky ends so that in any one recognition reaction ends cut by a particular RE receive a unique moiety. Recognition moieties comprise oligomers capable of specifically hybridizing to the RE generated sticky ends. In the preferred RE embodiment, which uses PCR amplification, the recognition moieties also provide primer means for the PCR.

The recognition moieties also provide for labeling and recognition of RE cut ends. For example, using a pair of REs in one recognition reaction generates doubly cut fragments some with the recognition sequence of the first RE on both ends, some with the recognition sequence of the second RE on both ends, and the remainder with one recognition sequence of each RE on either end. Using more REs generates doubly cut fragments with all pairwise combinations of RE cut ends from adjacent RE recognition sites along the sample sequences. All these cutting combinations need preferably to be distinguished, since each provides unique information on the presence of different subsequences pairs present in the original DNA sequence. Thus the recognition moieties preferably have unique labels which label specifically each RE cut made in a reaction. As many REs can be used in a single reaction as labeled recognition moieties are available to uniquely label each RE cut. If the detectable labeling in a particular system is, for example, by fluorochromes, then fragments cut with one RE have a single fluorescent signal from the one fluorochrome associated with that RE, while fragments cut with two REs have mixed signals, one from the fluorochrome associated with each RE. Thus all possible pairs of fluorochrome labels are preferably distinguishable. Alternatively, if certain target subsequence information is not needed, the recognition moieties need not be distinctively labeled. In embodiments using PCR amplification, corresponding primers would not be labeled.

If silver staining is used to recognize fragments separated on an electrophoresis gel, no recognition moiety need be labeled, as fragments cut by the various RE combinations are not distinguishable. In this case, when PCR amplification is used, only primers are required.

The recognition reaction conditions are preferably selected, as described in § 6.4, so that RE cutting and recognition moiety ligation go to full completion: all recognition sites of all REs in the reaction are cut and ligated to a recognition moiety. In this manner, the fragments generated from a sequence analyzed lie only between adjacent recognition sites of any RE in that reaction. No fragments remain which include any RE recognition site, since such a site is cut. Multiple REs can be used in one recognition reaction. Too many REs in one reaction may cut the sequences too frequently, generating a compressed length distribution with many short fragments of lengths between 10 and a few hundred base pairs long. Such a distribution may not be resolvable by the separation means, for example gel electrophoresis, if the fragments are too close in length, for example less than 3 bp apart on the average. Too many REs also may generate fragments of the same length and end subsequences from different sample sequences, thereby leading to non-unique signals. Finally, where fragment labels are to be distinguished, no more REs can be used than can have distinguishably labeled sticky ends. These considerations limit the number of REs optimally useable in one recognition reaction. Preferably two REs are used, with one, three and four REs less preferable. Preferable pairs of REs for the analysis of human cDNA samples are listed in § 6.9.

An additional level of signal specificity is possible by selecting or suppressing fragments having a third internal target subsequence. Additional information on the presence or absence of specific internal subsequences can be used along with the two end subsequences and the length information to further distinguish between otherwise identically classified fragments.

To select fragments with a third internal subsequence, probes with distinguishable labels which bind to this target subsequence are added to the fragments prior to detection, and alternatively prior to separation and detection. On detection, fragments with this third subsequence present will generate a signal, preferably fluorescent, from the probe. Such a probe could be a labeled PNA or DNA oligomer. Short DNA oligomers may need to be extended with a universal nucleotide or degenerate sets of natural nucleotides in order to provide for specific hybridization.

Fragments with a third subsequence can be suppressed in various manners in embodiments using PCR amplification. First, a probe hybridizing with this third subsequence which prevents polymerase elongation in PCR can be added prior to amplification. Then sequences with this subsequence will be at most linearly amplified and their signal thereby suppressed. Such a probe could be a PNA or modified DNA oligomer (with the last nucleotide being a ddNTP). Second, if the third subsequence is recognized by an RE, this RE can be added to the RE-ligase reaction without any corresponding specific primer. Fragments with the third subsequence will be at most linearly amplified.

Both these alternatives can be extended to multiple internal sequences by using multiple probes to recognize the sequences or to disrupt exponential PCR amplification.

Construction of the recognition moieties, also herein called adapters or linker-primers, is important and is described here in advance of further details of the individual recognition reaction steps. In the preferred embodiment, the adapters are partially double stranded DNA ("dsDNA"). Alternatively, the adapters can be constructed as oligomers of any nucleic acid, with corresponding properties to the preferred DNA polymers. In an embodiment employing an alternative amplification means, any polymer that can serve with a template as a primer for that amplification means can be used in that embodiment.

FIG. 2A illustrates the DNA molecules involved in the ligation reaction as conventionally indicated with the 5' ends of the top strands and the 3' ends of the bottom strands at left. dsDNA 201 is a fragment of a sample cDNA sequence with an RE cut at the left end generating, preferably, a four bp 5' overhang 202. Adapter dsDNA 209 is a synthetic substrate provided by this invention.

The precise characteristics of adapter 209 are selected in order to ensure that RE digestion and adapter ligation preferably go to completion, that generation of unwanted products and amplification biases are minimized, and that unique labels are attached to cut ends (if needed). Adapter 209 comprises strand 203, called a primer, and a partially complementary strand 205, called a linker. The primer is also known as the longer strand of the adapter, and the linker is also known as the shorter strand of the adapter.

The linker, or shorter strand, links the end of a cDNA cut by an RE to the primer, or longer strand, by hybridization to the sticky overhang of the cut end and to the primer in order that the primer can be ligated to dsDNA 201. Therefore, linker 205 comprises sequence 206 complementary to the sticky RE overhang 202 and sequence 207 complementary to the 3' end of primer 203. Sequence 206 is preferably of the same length as the RE overhang. Sequence 207 is most preferably eight nucleotides long, less preferably from 4 to 12 nucleotides long, but can be of any length as long as the linker reliably hybridizes with only one top primer in any one recognition reaction and has an appropriate $T_m$ (preferably less than approximately 68° C.). Linker 205 also preferably has no 5' terminal phosphate so that it will not ligate to the bottom strand of dsDNA 201. Lack of terminal phosphate also prevents the annealed adapters from ligating to each other, forming dimers, and thereby competing with adapter ligation to RE cut sample fragments. Adapter diners would also be amplified in a subsequent amplification step generating unwanted fragments. Terminal phosphates can be removed using phosphatases known in the art, followed by separation of the enzyme. An exemplary protocol for an alkaline phosphatase reaction is found in § 6.4.1.

Further, the linker, or shorter strand, $T_m$ should preferably be less than primer 203 self-annealing $T_m$. This ensures that subsequent PCR amplification conditions can be controlled so that linkers present in the reaction mixture will not hybridize and act as PCR primers, and, thereby, generate spurious fragment lengths. The preferable $T_m$ is less than approximately 68° C.

Primer, or longer strand, 203 further has a 3' end sequence 204 complementary to 3' end sequence 207 of bottom linker 205. In a preferred aspect, in order that all RE cuts are properly ligated to a unique top primer, in any single reaction, each primer should be complementary to and hybridize with only one linker 205. Consequently, all the linkers in any one reaction mixture preferably have unique sequences 207 for hybridizing with unique primers. In order that the ligation reaction go to completion, primer 203 preferably should not recreate the recognition sequence of any RE in the reaction mixture when it is ligated with cDNA end 202. Primer 203 has no 5' terminal phosphate in order to prevent any self-ligations. To minimize amplification of undesired sequences, termed amplification noise, in any subsequent PCR step it is preferred that primer 203 not hybridize with any sequence present in the original sample mixture. The $T_m$ of primer 203 is preferably high, in the range from 50° to 80° C., and more preferably above 68° C. This ensures that the subsequent PCR amplification can be controlled so that only primers and not linkers initiate new chains. For example, this $T_m$ can be achieved by use of a primer having a combination of a G+C content preferably from 40–60%, most preferably from 55–60%, and a primer length most preferably 24 nucleotides, and preferably from 18 to 30 nucleotides. Primer 203 is optionally labeled with fluorochrome 208, although any DNA labeling system that preferably allows multiple labels to be simultaneously distinguished is usable in this invention.

Generally, the primer, or longer strand, are constructed so that, preferably, they are highly specific, free of dimers and hairpins, and form stable duplexes under the conditions specified, in particular the desired $T_m$. Software packages are available for primer construction according to these principles, an example being OLIGO™ Version 4.0 For Macintosh from National Biosciences, Inc. (Plymouth, Minn.). In particular, a formula for $T_m$ can be found in the OLIGO™ Reference Manual at Eqn. I, page 2.

FIG. 2B illustrates two exemplary adapters and their component primers and linkers constructed according to the above description. Adapter 250 is specific for the RE BamHI, as it has a 3' end complementary to the 5' overhang generated by BamHI. Adapter 251 is similarly specific for the RE HindIII.

Example 6.9 contains a more comprehensive, non-limiting list of adapters that can be used according to the invention. All synthetic oligonucleotides of this invention are preferably as short as possible for their functional roles in order to minimize synthesis costs.

Alternatively, adapters can be constructed from hybrid primers which are designed to facilitate the direct sequencing of a fragment or the direct generation of RNA probes for in situ hybridization with the tissue of origin of the DNA sample analyzed. Hybrid primers for direct sequencing are constructed by ligating onto the 5' end of existing primers the M13–21 primer, the M13 reverse primer, or equivalent sequences. Fragments generated with such hybrid adapters can be removed from the separation means and amplified and sequenced with conventional systems. Such sequence information can be used both for a previously known sequence to confirm the sequence determination and for a previously unknown sequence to isolate the putative new gene. Hybrid primers for direct generation of RNA hybridization probes are constructed by ligating onto the 5' end of existing primers the phage T7 promoter. Fragments generated with such hybrid adapters can be removed using the separation means and transcribed into anti-sense RNA with conventional systems. Such probes can be used for in situ hybridization with the tissue of origin of the DNA sample to determine in precisely what cell types a signal of interest is expressed. Such hybrid adapters are illustrated in § 6.7.1.

A further alternative illustrated in FIG. 2C is to construct an adapter by self hybridization of single stranded DNA in hairpin loop configuration 212. The subsequences of loop 212 would have similar properties to the corresponding subsequences of linker 205 and primer 203. Exemplary hairpin loop 211 sequences are $C_4$ to $C_{10}$.

Figures 3A, 3B:
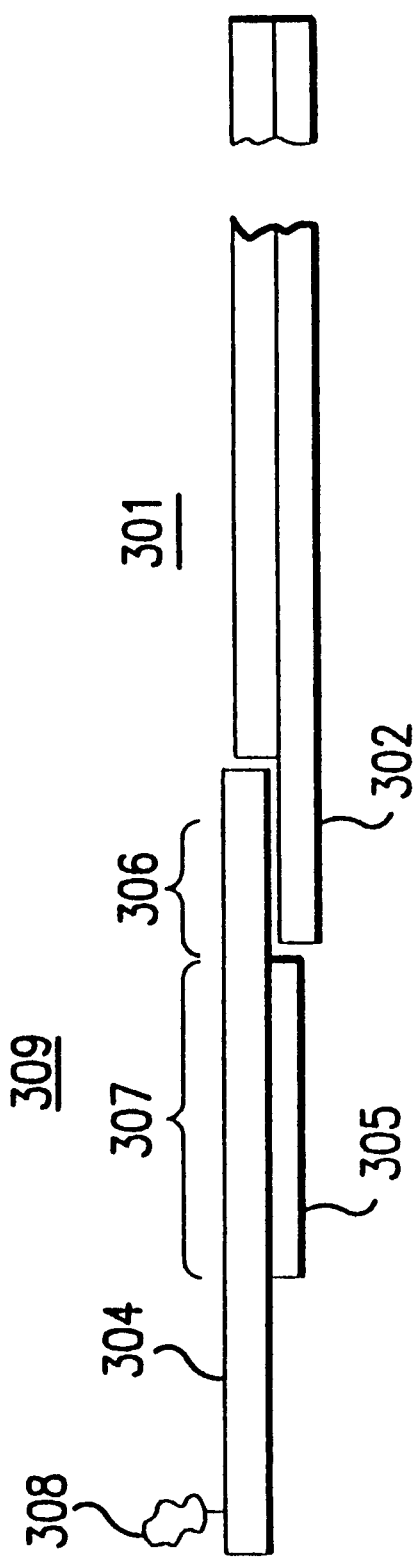

REs generating 3' overhangs are less preferred and require the different adapter structure illustrated in FIG. 3A. dsDNA 301 is a fragment of a sample cDNA cut with a RE generating 3' sticky overhang 302. Adapter 309 comprises primer, or longer strand, 304 and linker, or shorter strand, 305. Primer, or longer strand, 304 includes segment 306 complementary to and of the same length as 3' overhang 302 and section 307 complementary to linker 305. It also optionally has label 308 which distinctively labels primer 304. As in the case of adapters for 5' overhangs, primer 304 has no 5' terminal phosphate, in order to prevent self-ligations, and is such that no recognition site for any RE in one recognition reaction is created upon ligation of the primer with dsDNA 301. These condition ensure that the RE digestion and ligation reactions go to completion. Primer 304 should preferably not hybridize with any sequence in the initial sample mixture. The $T_m$ of primer 304 is preferably high, in the range from 50° to 80° C., and more preferably above 68° C. This ensures the subsequent PCR amplification can be controlled so that only primers and not linkers initiate new chains. For example, this $T_m$ can be achieved by using a primer having a G+C content preferably from 40–60%, most preferably from 55–60%, and a primer length most preferably of 24 nucleotide and less preferably of 18–30 nucleotides. Each primer 304 in a reaction can optionally have a distinguishable label 308, which is preferably a fluorochrome.

Linker, or shorter strand, 305 is complementary to and hybridizes with section 307 of primer 304 such that it is adjacent to 3' overhang 302. Linker 305 is most preferably 8 nucleotides long, less preferably from 4–16 nucleotides, and has no terminal phosphates to prevent any self-ligation. This linker serves only to promote ligation specificity and reaction speed. It does not perform the function of linking primer 304 to the cut dsDNA, as it did in the 5' case. Further, linker 305 $T_m$ should preferably be less than primer 304 self-annealing $T_m$. This insures that subsequent PCR amplification conditions can be controlled so that linkers present in the reaction mixture will not hybridize and act as PCR primers, and, thereby, generate spurious fragment lengths.

FIG. 3B illustrates an exemplary adapter with its primer and linker for the case of the RE NlaIII. As in the 5' overhang case, a 3' adapter can also be constructed from a hairpin loop configuration.

REs generating 5' and 3' overhangs are preferably not used in the same recognition reaction. This is in order that a complementary primer hybridization site can be presented on each of the two strands of the product of the RE/ligase recognition reaction.

Turning now to a detailed description of a preferred RE embodiment of the QEA recognition reactions, the steps of this preferred embodiment comprise, first, simultaneously cleaving a mixed DNA sample with one or more REs and ligating recognition moieties on the cut ends, second, amplifying the twice cut fragments, if necessary, and third, separating the fragments by length and detecting the lengths and labels, and the identities of the REs cutting each fragment. If necessary, prior to the first step, the cDNA sample is prepared by methods commonly known in the art or as described in §§ 6.3 and 6.4.1. Following the amplification step, optional steps to remove unwanted singly stranded DNA fragments prior to detection can increase the signal to noise ratio of the following detection. Two alternative RE embodiments are described in following subsections. The number of REs and associated adapters preferably are limited so that both a compressed length distribution consisting of shorter fragments is avoided and enough distinguishable labels are available for all the REs used. Alternatively, REs can be used without associated adapters in order that the amplified fragments not have the associated recognition sequences. Absence of these sequences can be used to additionally differentiate genes that happen to produce fragments of identical length with particular REs.

In more detail, a cDNA preparation step may start with a preexisting cDNA sample or with a tissue sample. When cDNA is prepared from tissue samples, the exemplary methods and procedures of Example 6.3 can be used. These consist of largely conventional steps of RNA preparation from the tissue sample, preferably poly(A) purified RNA is used but less preferably total cellular RNA can be used, RNase extraction, DNase treatment; mRNA purification, and first and second strand cDNA synthesis. Cloning into a vector is not necessary.

The final preparation step of a DNA sample is removal of terminal phosphates from all the cDNA. This is important to improve the signal to noise ratio in the subsequent fragment length separation and detection by eliminating amplification of unwanted, singly cut fragments. Significant background signals arise from exponential amplification of singly cut fragments whose blunt ends have ligated to form a single dsDNA with two cut ends, an apparently doubly cut fragment, which is exponentially amplified like a normal doubly cut fragment. Since cDNA lengths vary depending on synthesis condition, these unwanted, apparently doubly cut fragments have a wide range of lengths and produce a diffuse background on gel electrophoresis which obscures sharp bands from the normally doubly cut fragments. This background can be eliminated by preventing blunt end ligation of singly cut fragments by initially removing all terminal phosphates from the cDNA sample, without otherwise disrupting the integrity of the cDNA.

Terminal phosphate removal is preferably done with a phosphatase. To prevent interference with the intended ligation of adapters to doubly cut fragments, the phosphatase activity preferably is removed prior to the RE digestion and adapter ligation step. To avoid any phosphatase separation or extraction step, the preferred phosphatase is a heat labile alkaline phosphatase which is heat inactivated prior to the RE/ligase step. A preferred phosphatase comes from cold living Barents Sea (arctic) shrimp (U.S. Biochemical Corp.) ("shrimp alkaline phosphatase" or "SAP"). Terminal phosphate removal need be done only once for each population of cDNA being analyzed.

In other embodiments additional phosphatases my be used for terminal phosphate removal, such as calf intestinal phosphatase-alkaline from Boehringer Mannheim (Indianapolis, Ind.). Those that are not heat inactivated require the addition of a step to separate the phosphatase from the cDNA before the recognition reactions, such as by phenol-chloroform extraction.

Preferably, the prepared cDNA is then separated into batches of from 1 picogram ("pg") to 200 nanograms ("ng") of cDNA each, and each batch is separately processed by the further steps of the method. For a tissue mode experiment, to analyze gene expression, preferably from a majority of expressed genes, from a single human tissue requires determination of the presence of about 15,000 distinct cDNA sequences. By way of example, one sample is divided into approximately 50 batches, each batch is then subject to the RE/ligase recognition reaction and generates approximately 200–500 fragments, and more preferably 250 to 350 fragments of 10 to 1000 bp in length, the majority of fragments preferably having a distinct length and being uniquely derived from one cDNA sequence. A preferable example analysis would entail 50 batches generating approximately 300 bands each.

For the query mode, fewer recognition reactions are employed since only a subset of the expressed genes are of interest, perhaps approximately from 1 to 100. The number of recognition reactions in an experiment may then number approximately from 1 to 10 and an appropriate number of cDNA batches is prepared.

Following cDNA preparation, the next step is simultaneous RE cutting of and adapter ligation to the sample cDNA sequences. The prepared sample is cut with one or more REs. The amount of RE enzyme in the reaction is preferably approximately a 10 fold unit excess. Substantially greater quantities are less preferred because they can lead to star activity (non-specific cutting) while substantially lower quantities are less preferred because they will result in less rapid and only partial digestion, and hence incomplete and inaccurate characterization of the subsequence distribution.

In the same reaction, adapters and ligase enzyme are present for simultaneous adapter ligation to the RE cut ends. The method is adaptable to any ligase that is active in the temperature range 10 to 37° C. T4 DNA ligase is the preferred ligase. In other embodiments, cloned T4 DNA ligase or T4 RNA ligase can also be used. In a further embodiment, thermostable ligases can be used, such as Ampligase™ Thermostable DNA Ligase from Epicenpre (Madison, Wis.), which has a low blunt end ligation activity. These ligases in conjunction with the repetitive cycling of the basic thermal profile for the RE-ligase reaction, described in the following, permit more complete RE cutting and adapter ligation.

Ligase activity can both generate unwanted products and also, if an RE recognition site is regenerated, can cause an endless cycle of further cutting and ligation. Terminal phosphate removal during cDNA preparation prevents spurious ligation of the blunt other ends of singly cut cDNA (and subsequent exponential amplification of the results). Other unwanted products are fragment concatamers formed when the sticky ends of cut cDNA fragments hybridize and ligate. Such fragment concatamers are removed by keeping the restriction enzymes active during ligation, thus cutting unwanted concatamers once they form. Further, adapters, once ligated, terminate further RE cutting, since adapters are selected such that RE recognition sites are not recreated. A high molar excess of adapters also is preferable since it limits concatamer formation by driving the RE and ligase reactions toward complete digestion and adapter ligation. Finally, unwanted adapter self-ligation is prevented since primers and linker also lack terminal phosphates (preferably due to synthesis without phosphates or less preferably due to pretreatment thereof with phosphatases).

The temperature profile of the RE/ligase reaction is important for achieving complete cutting and ligation. The preferred protocol has several stages. The first stage is at the optimum RE temperature to achieve substantially complete cutting, for example 37° C. for 15 minutes. The second stage is a ramp at −1° C./min down to a temperature for substantially compete annealing of adapters to the 4 bp sticky cut ends, for example at 10° C. During this ramp cutting and ligation continue. The third stage is at the optimum temperature for adapter annealing and ligation to the sticky ends. The fourth stage achieves substantially complete ligation of cut products, and is, for example, at 16° C. for 30 minutes. The fifth stage is again at the optimum RE to achieve complete cutting of all recognition sites, for example at 37° C. for 10 minutes. The sixth stage is to heat inactivate the ligase and, preferably, also the RE enzymes, and is, for example, 10 minutes at 65° C. The results are held at 4° C.

A less preferred profile involves repetitive cycling of the first five stages of the temperature protocol described above, that is from an optimum RE temperature to optimum annealing and ligation temperatures, and back to an optimum RE temperature. The additional cycles further drive the RE/ligase reactions to completion. In this embodiment, it is preferred to use thermostable ligase enzymes. The majority of restriction enzymes are active at the conventional 16° C. ligation temperature and hence prevent unwanted ligation events without thermal cycling. However, temperature profiles consisting of optimum ligation conditions interspersed with optimum RE cutting conditions cause both enzymatic reactions to proceed more rapidly than one constant temperature. An exemplary profile comprises periodically cycling between a 37° C. optimum RE temperature to a 10° C. optimum annealing and ligation temperature at a ramp of −1° C./min, then to a 16° C. optimum ligation temperature, and then back to the 37° C. optimum RE temperature. Following completion of approximately 2 to 4 of these temperature cycles, the RE and ligase enzymes are heat inactivated by a final stage at 65° C. for 10 minutes. This avoids the need for separation or extractions between steps. The results are held at 4° C.

These thermal profiles are easily controlled and automated by the use of commercially available computer controlled thermocyclers, for example from MJ Research (Watertown, Mass.) or Perkin Elmer (Norwalk, Ct.).

These reaction conditions are designed to achieve substantially complete cutting of all RE recognition sites present in the analyzed sequence mixture and complete ligation of reaction terminating adapters on the cut ends, each adapter being unique in one reaction for a particular RE cut end. The fragments generated are limited by adjacent RE recognition sites and no fragment includes internal undigested sites. Further, a minimum of unwanted self-ligation products and concatamers is formed.

Following the RE/ligase step is amplification of the doubly cut cDNA fragments. Although PCR protocols are described in the exemplary embodiment, any amplification method that selects fragments to be amplified based on end sequences is adaptable to this invention (see above). With high enough sensitivity of detection means, or even single molecule detection means, the amplification step can be dispensed with entirely. This is preferable as amplification inevitably distorts the quantitative response of the method.

The PCR amplification protocol is designed to have maximum specificity and reproducibility. First, the PCR amplification produces fewer unwanted products if the amplification steps occur at a temperature above the $T_m$ of the shorter linker so that it cannot initiate unwanted DNA strands. The linker is preferably melted by an initial incubation at 72° C. without the Taq polymerase enzyme or dNTP substrates present. A further incubation at 72° C. for 10 minutes with Taq polymerase and dNTPs is performed in order to complete partial double strands to complete double strands. Alternatively, linker melting and double strand completion can be performed by a single incubation at 72° C. for 10 minutes with Taq polymerase. Subsequent PCR amplification steps are carried out at temperatures sufficiently high to prevent re-hybridization of the bottom linker.

Second, primer strand 203 of FIG. 2A (and 304 of FIG. 3A) are typically used as PCR primers. They are preferably designed for high amplification specificity and not to hybridize with any native cDNA species to be analyzed. They have high melting temperatures, preferably above 50° C. and most preferably above 68° C., to ensure specific hybridization with a minimum of mismatches.

Third, the protocol's temperature profile is preferably designed for specificity and reproducibility. The preferred profile is 95° C. for 30 seconds followed by 65° C. for 1 minute. High annealing temperatures minimize primer mis-hybridizations. Longer extension times reduce PCR bias in favor of smaller fragments. Longer melting times reduces PCR amplification bias in favor of high G+C content. Further, large amplification volumes are preferred to reduce bias. Sufficient amplification cycles are performed, typically between 15 and 30 cycles.

Any other techniques designed to raise specificity, yield, or reproducibility of amplification are applicable to this method. For example, one such technique is the use of 7-deaza-2'-dGTP in the PCR reaction in place of dGTP. This has been shown to increase PCR efficiency for G+C rich targets (Mutter et al., 1995, Nuc. Acid Res., 23:1411–1418). For a further example, another such technique is the addition of tetramethylammonium chloride to the reaction mixture, which has the effect of raising the $T_m$ (Chevet et al., 1995, Nucleic Acids Research, 23(16):3343–3344). In one method of performing the PCR amplification, each RE/ligase reaction sample is sub-divided into multiple aliquots, and each aliquot is amplified with a different number of cycles. Multiple amplifications with an increasing number of amplification cycles, for example 10, 15, and 20 cycles, are preferable. Amplifications with a lower number of cycles detect more prevalent messages in a more quantitative manner. Amplification with a higher number of cycles detect the presence of less prevalent genes but less quantitatively. Multiple amplifications also serve as controls for checking the reliability and quantitative response of the process by comparing the size of the same signal in each amplification.

Other methods of performing the PCR amplification are more suited to automation. For example, the content of a reaction vial can be configured as follows. First, 40 μl of the PCR mix without Mg ions is added followed by a wax bead that melts approximately at 72° C., such as Ampliwax beads (Perkin-Elmer, Norwalk, Ct.). This bead is melted at 75° C. for 5 minutes and solidified at 25° C. for 10 minutes. Last 10 μl of the RE/ligase mix with Mg ions is added. The RE/ligase and PCR reactions are carried out by following the temperature profile in FIG. 16D, which is a concatenation of the RE/ligase and PCR profiles with an extra 10 minutes at 72° C. In this arrangement in the same vial, the RE/ligase reactions can first be performed. The incubation at 72° C. for 20 minutes permits the wax layer separating the mixtures to melt, allows the RE/ligase mixture to mix with the PCR mix, and allows completion of the partial double strands to complete double strands. Then sufficient PCR cycles are performed, typically between 15 and 30 cycles. This single tube implementation is well adapted to automation. Other so called PCR "hot-start" procedures can be used, such as those employing heat sensitive antibodies (Invitrogen, Calif.) to initially block the activity of the polymerase.

Following the amplification step, optional steps prior to length separation and detection improve the method's signal to noise ratio. First, single strands produced as a result of linear amplification from singly cut fragments can be removed by the use of single strand specific exonucleases. Mung Bean exonuclease (Exo) or Exo I can be used, with Exo I preferred because of its higher specificity for single strands. Mung bean is less preferred and even less preferred is S1 nuclease. Second, the amplified products may be optionally concentrated by ethanol precipitation or column separation.

Figure 2D:
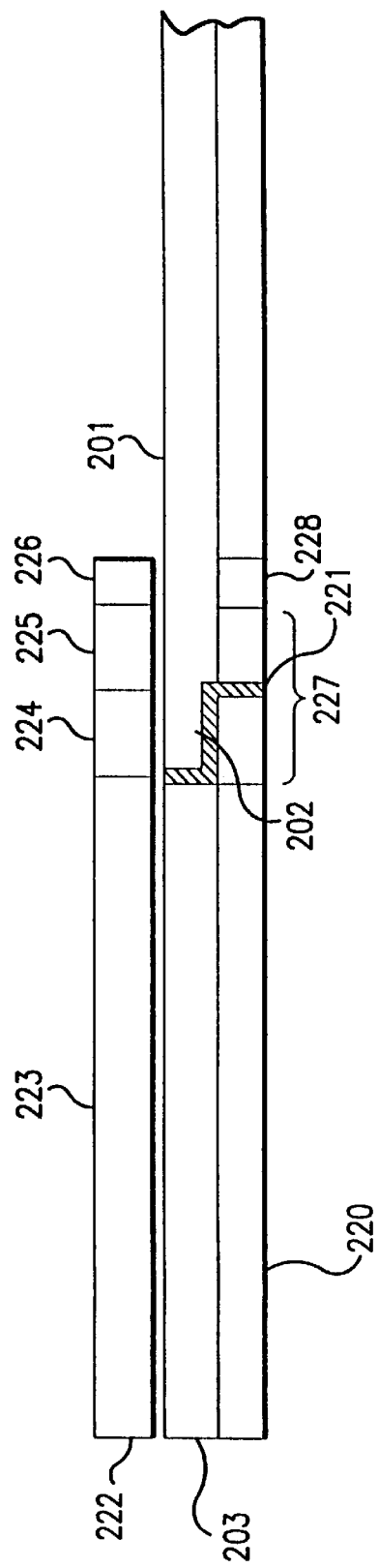

Alternate PCR primers illustrated in FIG. 2D can be advantageously used. In that figure, sample dsDNA 201 is illustrated after the RE/ligase reaction and after incubation at 72° C. for 10 minutes but just prior to the PCR amplification steps. dsDNA 201 has been cleaved by an RE recognizing subsequence 227 at position 221 producing overhang 202 and has been ligated to adapter primer strand 203. For definiteness and without limitation, a particular relative position between RE recognition subsequence 227 and overhang 202 is illustrated. Other relative positions are known. The resulting DNA has been completed to a blunt ended double strand by completing strand 220 by incubation at 72° C. for 10 minutes. Typically adapter primer strand 203 is used as the PCR primer.

Alternatively strand 222, illustrated with its 5' end at the left, can be advantageously used. Strand 222 comprises subsequence 223, with the same sequence as strand 203; subsequence 224, with the same sequence as the RE overhang 202; subsequence 225, with a sequence consisting of a remaining portion of RE recognition subsequence 227, if any; and subsequence 226 of P nucleotides. Length P is preferably from 1 to 6 and more preferably either 1 or 2. Subsequences 223 and 224 hybridize for PCR priming with corresponding subsequences of dsDNA 201. Subsequence 225 hybridizes with any remainder of recognition subsequence 227. Subsequence 226 hybridizes only with fragments 201 having complementary nucleotides in corresponding positions 228. When P is 1, primer 223 selects for PCR amplification 1 of the 4 possible dsDNAs 201 which may be present; and when P is 2, 1 of the 16 is selected. If 4 (or 16) primers 223 are synthesized, each with one of the possible (pairs of) nucleotides, and if the RE/ligase reactions mix is separated in 4 (16) aliquots for use with one of these 4 (16) primers, the 4 (16) PCR reactions will select for amplification only one of the possible dsDNAs 201. Thus these primers are similar to phasing primers (European Patent Application No. O 534 858 A1, published Mar. 31, 1993).

The joint result of using primers 223 with subsequence 226 in multiple PCR reactions after one RE/ligase reaction is to extend the effective target subsequence from the RE recognition subsequence by concatenating onto the recognition subsequence a subsequence which is complementary to subsequence 226. Thereby, many additional target subsequences can be recognized while retaining the specificity and exactness characteristic of the RE embodiment. For example, REs recognizing 4 bp subsequences can be used in such a combined reaction with an effective 5 or 6 bp target subsequence, which need not be palindromic. REs recognizing 6 bp sequences can be used in a combined reaction to recognize 7 or 8 bp sequences. Such effective recognition sequences need to be accounted for in the computer implemented design and analysis methods subsequently described.

The next QEA step is the separation by length of the amplified, labeled, cut cDNA fragments and observation of the length distribution. Lengths of the sample of cut fragments will typically span a range from a few tens of bp to perhaps 1000 bp. For this range standard gel electrophoresis is capable of resolving separate fragments which differ by three or more base pairs. Knowledge of average fragment composition allows for correction of composition induced small mobility differences and permits resolution down to 1 bp. Any separation method with adequate length resolution, preferably at least to three base pairs in a 1000 base pair sequence, can also be used. The length distribution is detected with means sensitive to the primer labels. In the case of fluorochrome labels, since multiple fluorochrome labels can be typically be resolved from a single band in a gel, the products of one recognition reaction with several REs or other recognition means or of several separate recognition reaction can be analyzed in a single lane. The detection apparatus resolution for different labels limits the number of RE products that can be simultaneously detected.

Preferred protocols for the specific RE embodiments are described in detail in § 6.4.

5.2.1. FIRST ALTERNATIVE RE EMBODIMENT

An alternative QEA protocol performs amplification prior to the RE/ligase step. After the RE/ligase step, further amplification is performed. Alternately, no further amplification is performed, and in this case unwanted singly cut ends are removed as they are not diluted by subsequent amplification.

Such removal is accomplished by first using primers that are labeled with a capture moiety. A capture moiety is a substance having a specific binding partner that can be affixed to a solid substrate. For example, suitable capture moiety-binding partner pairs include but are not limited to biotin-streptavidin, biotin-avidin, a hapten (such as digoxigenin) and a corresponding antibody, or other removal means known in the art. For example, double stranded cDNA, perhaps prepared from a tissue sample according to Example 6.3, is PCR amplified using a set of biotin-labeled, arbitrary primers with no net sequence preference. The result is partial cDNA sequences with biotin labels linked to both ends. The amplified cDNA is cut with REs and ligated to recognition moieties uniquely for each particular RE cut end. The RE/ligase step is performed by procedures identical to those of the prior section in order to drive the RE digestion and recognition moiety ligation to completion and to prevent formation of concatamers and other unwanted ligation products. The recognition moieties can be the adapters previously described.

Next the unwanted singly cut fragments labeled with the capture moiety are removed by contacting them with the binding partner for the capture moiety affixed to a solid phase, followed by removal of the solid phase. For example, where biotin is the capture moiety, singly cut fragments can be removed using streptavidin or avidin magnetic beads, leaving only doubly cut fragments that have RE-specific recognition moieties ligated to each end. These products are then analyzed, also as in the previous section, to determine the distribution of fragment lengths and RE cutting combinations.

Other direct removal means may alternatively be used in this invention. Such removal means include but are not limited to digestion by single strand specific nucleases or passage though a single strand specific chromatographic column, for example, containing hydroxyapatite.

5.2.2. SECOND ALTERNATIVE RE EMBODIMENT

A second alternative embodiment in conjunction with sufficiently sensitive detection means can eliminate altogether the amplification step. In the preferred RE protocol, doubly cut fragments ligated to adapters are exponentially amplified, while unwanted, singly cut fragments are at best linearly amplified. Thus amplification dilutes the unwanted fragments relative to the fragments of interest. After ten cycles of amplification, for example, signals from unwanted fragments are reduced to less than approximately 0.1% of the signals from the doubly cut fragments. Gene expression can then be quantitatively determined down to at least this level. A greater number of amplification cycles results in a greater relative dilution of signals from unwanted singly cut fragments and, thereby, a greater sensitivity. But amplification bias and non-linearities interfere with the quantitative response of the method. For example, certain fragments will be preferentially PCR amplified depending on such factors as length and average base composition.

For improved quantitative response, it is preferred to eliminate the bias accompanying the amplification steps. Then output signal intensity is linearly responsive to the number of input genes or sequences generating that signal. In the case of common fluorescent detection means, a minimum of $6 \times 10^{-18}$ moles of fluorochrome (approximately $10^5$ molecules) is required for detection. Since one gram of cDNA contains about $10^{-6}$ moles of transcripts, it is possible to detect transcripts to at least a 1% relative level from microgram quantities of RNA. With greater mRNA quantities, proportionately rarer transcripts are detectable. Labeling and detection schemes of increased sensitivity permit use of less mRNA. Such a scheme of increased sensitivity is described in Ju et al., 1995, Fluorescent energy transfer dye-labeled primers for DNA sequencing and analysis, Proc. Natl. Acad. Sci. USA 92:4347–4351. Single molecule detection means are about $10^5$ times more sensitive than existing fluorescent means (Eigen et al., 1994, Proc. Natl. Acad. Sci. USA, 91:5740–5747).

To eliminate amplification steps, a preferred protocol uses a capture moiety separation means to directly remove singly cut fragments from the desired doubly cut fragments. Only the doubly cut fragments have a discrete length distribution dependent only on the input gene sequences. The singly cut fragments have a broad non-diagnostic distribution depending on cDNA synthesis conditions. In this protocol, cDNA is synthesized using a primer labeled with a capture moiety, is circularized, cut with REs, and ligated to adapters. Singly cut ends are then removed by contact with a solid phase to which a specific binding partner of the capture moiety is affixed.

Figure 4A:
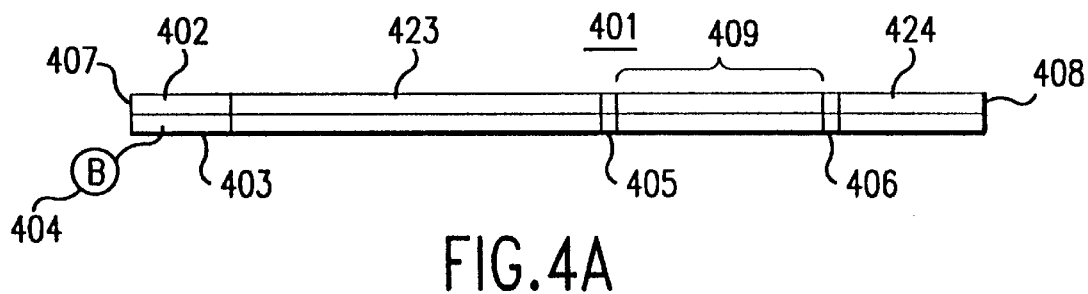
Figure 4B:
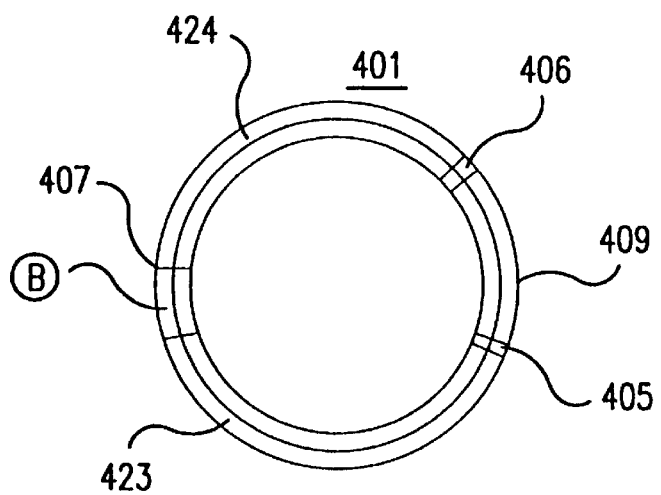
Figure 4C:
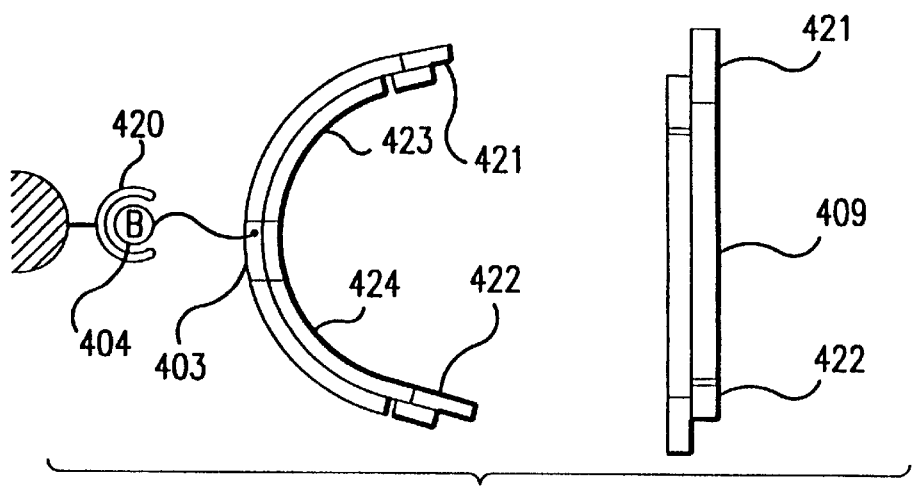

FIGS. 4A, 4B, and 4C illustrate a second alternative RE protocol, which uses biotin as such a capture moiety for direct removal of the singly cut 3' and 5' cDNA ends from the RE/ligase mixture. cDNA first strands are synthesized according to the method of Example 6.3 using, for example, an oligo(dT) primer with a biotin molecule linked to one of the internal thymidine nucleotides. For example, such a primer is $T_n T(biotin) T_m$, with n approximately equal to m, and with n+m sufficiently large, approximately 12 to 20, so that the primer will reliably hybridize to the poly(A) tail of mRNA. Other biotin labeled primers may also be used, such as random hexamers. Double stranded cDNA is then synthesized, also according to Example 6.3, and any ends filled in to form full dsDNA. Terminal phosphates are retained.

FIG. 4A illustrates such a cDNA 401 with ends 407 and 408, poly(dA) sequence 402, poly(dT) primer 403 with biotin 404 attached. 405 is a recognition sequences for $RE_1$; 406 is a sequence for $RE_2$. Fragment 409 is the cDNA sequence defined by these adjacent RE recognition sequences. Fragments 423 and 424 are singly cut fragments resulting from RE cleavages at sites 405 and 406.

Next, the cDNA is ligated into a circle. A ligation reaction using, for example, T4 DNA ligase is performed under sufficiently dilute conditions so that predominantly intramolecular ligations occur circularizing the cDNA, with a only a minimum of intermolecular, concatamer forming ligations. Reaction conditions favoring circularization versus concatamer formation are described in Maniatis, 1982, Molecular Cloning A Laboratory Manual, pp. 124–125, 286–288, Cold Spring Harbor, N.Y. Preferably, a DNA concentration of less than approximately 1 $\mu$g/ml has been found adequate to favor circularization. Concatamers can be separated from circularized single molecules by size separation using gel electrophoresis, if necessary. FIG. 4B illustrates the circularized cDNA. Blunt end ligation occurred between ends 407 and 408.

Then the circularized, biotin end labeled, cDNA is cut with REs and ligated to adapters uniquely recognizing and perhaps uniquely labeled for each particular RE cut. The RE/ligase step is preferred by procedures as described in the section hereinabove in order to drive RE digestion and primer ligation to completion over formation of concatamers and other unwanted ligation products. Next, the unwanted singly cut ends are removed using streptavidin or avidin magnetic beads, leaving only doubly cut fragments that have RE-specific recognition sequences ligated to each end.

FIG. 4C illustrates these latter steps. Sequences 405 and 406 are cut by $RE_1$ and $RE_2$, respectively, and adapters 421 and 422 specific for cuts by $RE_1$ and $RE_2$, respectively are ligated onto the sticky ends. Thereby, fragment 409 is freed from the circularized cDNA and adapters 421 and 422 are ligated to it. The remaining segment of the circularized cDNA comprises singly cut ends 423 and 424 with ligated adapters 421 and 422. Both singly cut ends are joined to the primer sequence 403 with attached biotin 404. Removal is accomplished by contact with streptavidin or avidin 420 which is fixed to substrate 425, perhaps comprising magnetic beads. The doubly cut labeled fragment 409 can now be simply separated from the singly cut ends affixed to the substrate. Thereby, separation of the singly and doubly cut fragments is achieved.

Signals from the uniquely labeled doubly cut ends can be directly detected without any unwanted contamination from signals from labeled singly cut ends. Importantly, since signals originate only from cDNA sequences originally present in the sample, the detected signals will quantitatively reflect cDNA sequence content and thus gene expression levels. If the expression level is too low for direct detection, the sample can be subjected to just the minimum number of cycles of amplification, according to the methods of Example 6.4, to detect the gene or sequence of interest. For example, the number of cycles can be as small as four to eight without any concern of background contamination or noise. Thus, in this embodiment, amplification is not needed to suppress signals from singly cut ends, and preferred more quantitative response signal intensities result.

5.3. PCR EMBODIMENT OF QEA

An alternative implementation of the QEA method not using REs is based on PCR, or alternative amplification means, to select and amplify cDNA fragments between chosen target subsequences recognized by amplification primers. See, generally, Innis et al., 1989, PCR Protocols A Guide to Methods and Applications, Academic Press, New York, and Innis et al., 1995, PCR Strategies, Academic Press, New York.

Typically target subsequences between four and eight base pairs long chosen by the methods previously described are preferred because of their greater probability of occurrence, and hence information content, as compared to longer subsequences. However, DNA oligomers this short may not hybridize reliably and reproducibly to their complementary subsequences to be effectively used as PCR primers. Hybridization reliability depends strongly on several variables, including primer composition and length, stringency condition such as annealing temperature and salt concentration, and cDNA mixture complexity. For the hash code to be effective for gene calling, it is highly preferred that subsequence recognition be as specific and reproducible as possible so that well resolved bands representative only of the underlying sample sequence are produced. Thus, instead of directly using single short oligonucleotides complementary to the selected, target subsequences as primers, it is preferable to use carefully designed primers.

The RE embodiments of QEA have been verified to produce reproducible signal patterns over a 103 range on input DNA concentrations. The PCR embodiment is less preferred because the input DNA concentration, as well as the initial hybridization temperature, must be closely to yield reproducible results.

Figure 5:
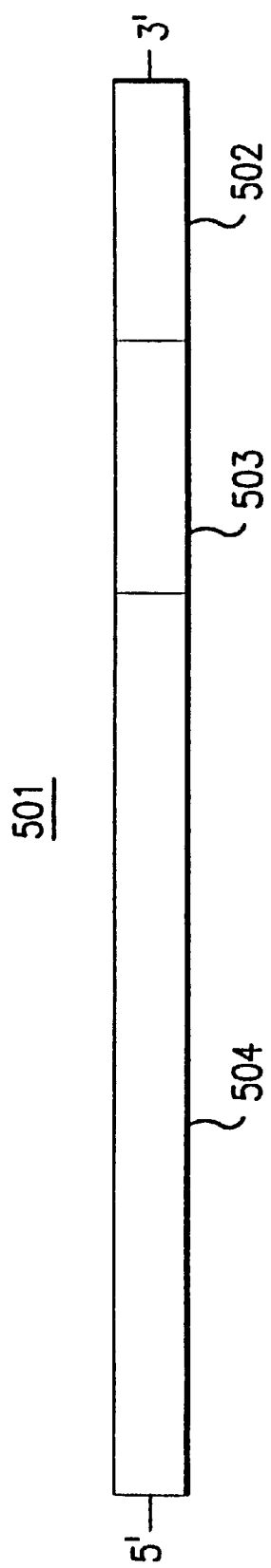
FIG. 5 shows the DNA primers for a PCR embodiment of the QEA method.

The preferred primers are constructed according to the model in FIG. 5. Primer 501 is constructed of three components, which, listed 5' to 3', are 504, 503, and 502. Component 503, described infra, is optional. Component 502 is a sequence which is complementary to the subsequence which primer 501 is designed to recognize. Component 502 is typically 4–8 bp long. Component 504 is a 10–20 bp sequence chosen so the final primer does not hybridize with any native sequence in the cDNA sample to be analyzed; that is, primer 501 does not anneal with any sequence known to be present in the sample to be analyzed. The sequence of component 504 is also chosen so that the final primer has a melting point above 50° C., and preferably above 68° C. The method for controlling melting temperature selecting average primer composition and primer length is described above.

Use of primer 501 in the PCR embodiment involves a first annealing step, which allows the 3' end component 502 to anneal to its target subsequence in the presence of end component 504, which may not hybridize. Preferably, this annealing step is at a temperature between 36 and 44° C. that is empirically determined to maximize reproducibility of the resulting signal pattern. The DNA concentration is approximately 10 ng/50 ml and is similarly determined to maximize reproducibility. Other PCR conditions are standard and are described in § 6.5. Once annealed, the 3' end serves as the primer elongation point for the subsequent first elongation step. The first elongation step is preferably at 72° C. for 1 minute.

If stringency conditions are such that exact complementarity is not required for hybridization, false positive signals can be generated, that is signals resulting from inexact recognition of the target subsequence. The generation of these false positive bands can be accounted for in the experimental analysis methods in order that DNA sample sequences can still be recognized, but, perhaps, with some increased recognition ambiguity that may need resolution. These bands are accourted for by allowing inexact hybridization matches of the target subsequence, the degree of inexactness depending on the stringency of the hybridization conditions. In this case the signals generated contain only a fuzzy representation of the actual subsequence in the sample, the degree of fuzziness being a function of subsequence length and the stringency condition, that is binding free energy, and the temperature of the hybridization. Given the free energy and temperature, the various possible actual subsequences can be approximately determined by well known thermodynamic equilibrium calculations.

Subsequent PCR cycles then use high temperature, high stringency annealing steps. The high stringency annealing steps ensure exact hybridization of the entire primer. No further false positive bands are generated. Preferably, these PCR cycles alternate between a 65° C. annealing step and 95° C. melting step, each for 1 minute.

Optional component 503 can be used to improve the specificity of the first low stringency annealing step and thereby minimize false positive bands generated then. Component 503 can be $-(N)_j-$, where N is any nucleotide and j is typically between 2 and 4, preferably 2. Use of all possible components 503 results in a degenerate set of primers, 16 primers if j=2, which have a 3' end subsequence effectively j bases longer than the target subsequence. These longer complementary end sequences have improved hybridization specificity. Alternately, component 503 can be $-(U)_j-$, where N is a "universal" nucleotide and j is typically between 2 and 4, preferably 3 or 4. A universal nucleotide, such as inosine, is capable of forming base pairs with any other naturally occurring nucleotide. In this alternative, single primer 501 has a 3' end subsequence effectively j bases longer than the target, and thus also has improved hybridization specificity.

A less preferred primer design comprises sets of degenerate oligonucleotides of sufficient length to achieve specific and reproducible hybridization, where each member of a set includes a shared subsequence complementary to one selected, target sequence. For example, if a subsequence to be recognized is GATT, the set of primers used may be all sequences of the form NNAATCNN, where N is any nucleotide. Also sets of degenerate primers permit the recognition of discontinuous subsequences. For example, GA--TT may be recognized by all sequences of the form NAANNTCNN. Alternately, a universal nucleotide can be used in place of the degenerate nucleotides represented by 'N'.

Each primer or primer set used in a single reaction is preferably distinctively labeled for detection. In the preferred embodiment using electrophoretic fragment separation, labeling is by fluorochromes that can be simultaneously distinguished with optical detection means.

An exemplary experimental protocol is summarized here, with details presented in § 6.5. Total cellular mRNA or purified sub-pools of cellular mRNA are used for cDNA synthesis. First strand cDNA synthesis is performed according to § 6.3 using, for example, an oligo(dT) primer or alternatively phasing primers. Alternatively, cDNA samples can be prepared from any source or be directly obtained.

Next, using a first strand cDNA sample, the primers of the selected primer sets are used in a conventional PCR amplification protocol. A high molar excess of primers is preferably used to ensure only fragments between primer sites that are adjacent on a target cDNA sequence or gene are amplified. With a high molar excess of primers binding to all available primer binding sites, no amplified fragment should include internally any primer recognition site. As many primers can be used in one reaction as can be labeled for concurrent separation and detection and which generate an adequately resolved length distribution, as in the RE embodiments. For example, if fluorochrome labeling is used, each pair of fluorochromes preferably is distinguishable in one band and separate pairs preferably are distinguishable in separate bands. After amplification, the fragments are separated, re-suspended for gel electrophoresis, electrophoretically separated, and optically detected. Thereby the length distribution of fragments having particular pairs of target subsequences at their ends is ascertained.

Preferred protocols for the specific PCR embodiments are described in detail in § 6.5.

5.4. QEA ANALYSIS AND DESIGN METHODS

This inventions provides two groups of methods for the Quantitative Expression Analysis embodiment of this invention: first, methods for QEA experimental design; and second, methods for QEA experimental analysis. Although, logically, design precedes analysis, the methods of experimental design depend on basic methods described herein as part of experimental analysis. Consequently, experimental analysis methods are described first.

In the following, descriptions are often cast in terms of the preferred QEA embodiment, in which REs are used to recognize target subsequences. However, such description is not limiting, as all the methods to be described are equally adaptable to all QEA embodiments, including those in which target subsequences are recognized by nucleic acid, or nucleic acid mimic, and probes which recognize target subsequences by hybridization.

Further, the following descriptions are directed to the currently preferred embodiments of these methods. However, it will be readily apparent to those skilled in the computer and simulation arts that many other embodiments of these methods are substantially equivalent to those described and can be used to achieve substantially the same results. This invention comprises such alternative implementations as well as its currently preferred implementation.

5.4.1. QEA EXPERIMENTAL ANALYSIS METHODS

The analysis methods comprise, first, selecting a database of DNA sequences representative of the DNA sample to be analyzed, second, using this database and a description of the experiment to derive the pattern of simulated signals, contained in a database of simulated signals, which will be produced by DNA fragments generated in the experiment, and third, for any particular detected signal, using the pattern or database of simulated signals to predict the sequences in the original sample likely to cause this signal. Further analysis methods present an easy to use user interface and permit determination of the sequences actually causing a signal in cases where the signal may arise from multiple sequences, and perform statistical correlations to quickly determine signals of interest in multiple samples.

The first analysis method is selecting a database of DNA sequences representative of the sample to be analyzed. In the preferred use of this invention, the DNA sequences to be analyzed will be derived from a tissue sample, typically a human sample examined for diagnostic or research purposes. In this use, database selection begins with one or more publicly available databases which comprehensively record all observed DNA sequences. Such databases are GenBank from the National Center for Biotechnology Information (Bethesda, Md.), the EMBL Data Library at the European Bioinformatics institute (Hinxton Hall, UK) and databases from the National Center for Genome Research (Santa Fe, N. Mex.). However, as any sample of a plurality of DNA sequences of any provenance can be analyzed by the methods of this invention, any database containing entries for the sequences likely to be present in such a sample to be analyzed is usable in the further steps of the computer methods.

Figures 6A, 6B:
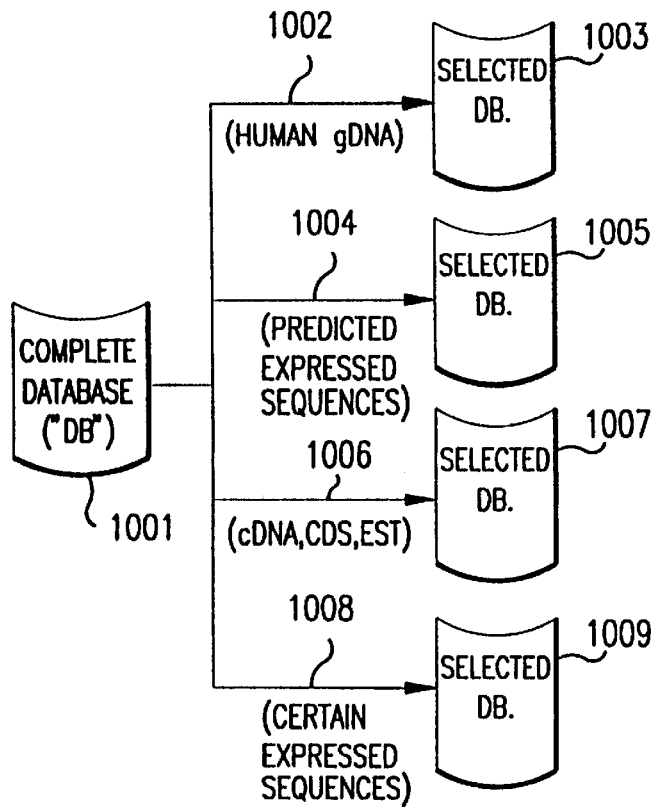
FIGS. 6A and 6B show a method for DNA sequence database selection according to this invention.

FIG. 6A illustrates the preferred database selection method starting from a comprehensive tissue derived database. Database 1001 is the comprehensive input database, having the exemplary flat-file or relational structure 1010 shown in FIG. 6B, with one row, or record, 1014 for each entered DNA sequence. Column, or field, 1011 is the accession number field, which uniquely identifies each sequence in database 1001. Most such databases contain redundant entries, that is multiple sequence records are present that are derived from one biological sequence. Column 1013 is the actual nucleotide sequence of the entry. The plurality of columns, or fields, represented by 1012 contain other data identifying this entry including, for example whether this is a cDNA or gDNA sequence, if cDNA, whether this is a full length coding sequence or a fragment, the species origin of the sequence or its product, the name of the gene containing the sequence, if known, etc. Although shown as one file, DNA sequence databases often exits in divisions and selection from all relevant divisions is contemplated by this invention. For example, GenBank has 15 different divisions, of which the EST division and the separate database, dbEST, that contain expressed sequence tags ("EST") are of particular interest, since they contain expressed sequences.

From the comprehensive database, all records are selected which meet criteria for representing particular experiments on particular tissue types. This is accomplished by conventional techniques of sequentially scanning all records in the comprehensive database, selecting those that match the criteria, and storing the selected records in a selected database.

The following are exemplary selection methods. To analyze a genomic DNA sample, database 1001 is scanned against criteria 1002 for human gDNA to create selected database 1003. To analyze expressed genes (cDNA sequences), several selection alternatives are available. First, a genomic sequence can be scanned in order to predict which subsequences (exons) will be expressed. Thus selected database 1005 is created by making selections according to expression predictions 1004. Second, observed expressed sequences, such as cDNA sequences, coding domain sequences ("CDS"), and ESTs, can be selected 1006 to create selected database 1007 of expressed sequences. Additionally, predicted and observed expressed sequences can be combined into another, perhaps more comprehensive, selected database of expressed sequences. Third, expressed sequences determined by either of the prior methods may be further selected by any available indication of interest 1008 in the database records to create more targeted selected database 1009. Without limitation, selected databases can be composed of sequences that can be selected according to any available relevant field, indication, or combination present in sequence databases.

The second analysis method uses the previously selected database of sequences likely to be present in a sample and a description of an intended experiment to derive a pattern of the signals which will be produced by DNA fragments generated in the experiment. This pattern can be stored in a computer implementation in any convenient manner. In the following, without limitation, it is described as being stored as a table of information. This table may be stored as individual records or by using a database system, such as any conventionally available relational database. Alternatively, the pattern may simply be stored as the image of the in-memory structures which represent the pattern.

A QEA experiment comprises several independent recognition reactions applied to the DNA sample sequences, where in each of the reactions labeled DNA fragments are produced from sample sequences, the fragments lying between certain target subsequences in a sample sequence. The target subsequences can be recognized and the fragments generated by the preferred RE embodiments of the QEA method or by the PCR embodiment of QEA. The following description is focused on the RE embodiments.

Figure 7:
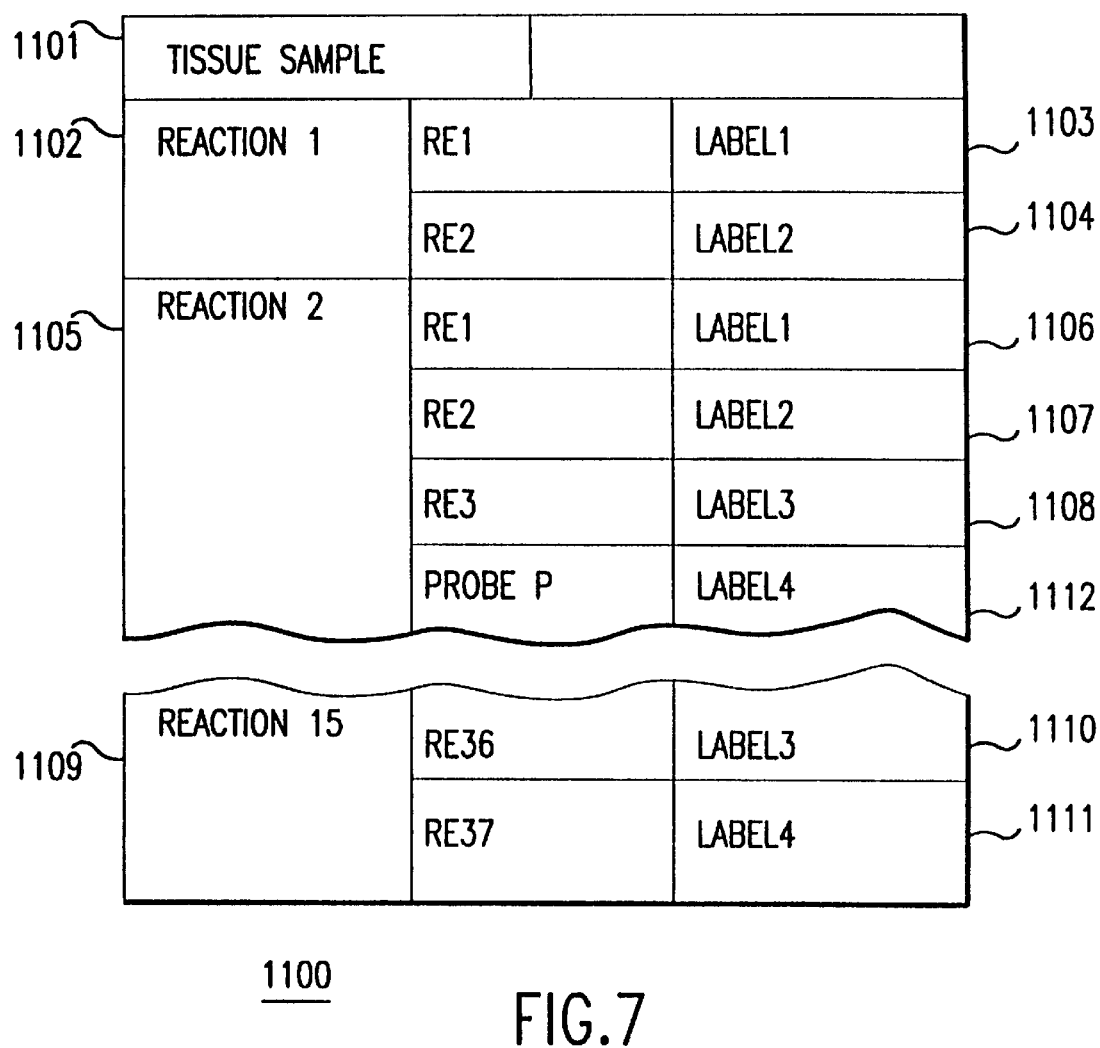
FIG. 7 shows an exemplary experimental description for the QEA embodiment of this invention.

FIG. 7 illustrates an exemplary description 1100 of a preferred QEA embodiment. Field 1101 contains a description of the tissue sample which is the source of the DNA sample. For example, one experiment could analyze a normal prostrate sample; a second otherwise identical experiment could analyze a prostrate sample with premalignant changes; and a third experiment could analyze a cancerous prostate sample. Differences in gene expression between these samples then relate to the progress of the cancer disease state. Such samples could be drawn from any other human cancer or malignancy.

Major rows 1102, 1105, and 1109 describe the separate individual recognition reactions to which the DNA from tissue sample 1101 is subjected. Any number of reactions may be assembled into an experiment, from as few as one to as many as there are pairs of available recognition means to recognize subsequences. FIG. 7 illustrates 15 reactions. For example, reaction 1 specified by major row 1102 generates fragments between target subsequences which are the recognition sites of restriction endonucleases 1 and 2 described in minor rows 1103 and 1104. Further, the RE1 cut end is recognized by a labeling moiety labeled with LABEL1, and the RE2 end is recognized by LABEL2. Similarly, reaction 15, 1109, utilizes restriction endonucleases 36 and 37 labeled with labels 3 and 4, minor rows 1110 and 1111, respectively.

Major row 1105 describes a variant QEA reaction using three REs and a separate probe. As described, many REs can be used in a single recognition reaction as long as a useful fragment distribution results. Too many REs results in a compressed length distribution. Further, probes for target subsequences that are not intended to be labeled fragment ends, but rather occur within a fragment, can be used. For example, a labeled probe added after the QEA PCR amplification step (if present in a given embodiment), a post PCR probe, can recognize subsequences internal to a fragment and thereby provide an additional signal which can be used to discriminate between two sample sequences which produce fragments of the same length and end sequence which otherwise have differing internal sequences. For another example, a probe added before the QEA PCR step and which cannot be extended by DNA polymerase will prevent PCR amplification of those fragment containing the probe's target subsequences. If PCR amplification is necessary to generate detectable signals (in a given embodiment), such a probe will prevent the detection of such a fragment. The absence of a fragment may make a previously ambiguous detected band now unambiguous. Such PCR disruption probes can be PNA oligomers or degenerate sets of DNA oligomers, modified to prevent polymerase extension (e.g. by incorporation of a dideoxynucleotide at the 3' end).

Where alternative phasing PCR primers are used, their extra recognition subsequences and labeling are described in rows dependent to the RE/ligase reaction whose products they are used to amplify.

Figure 8A:
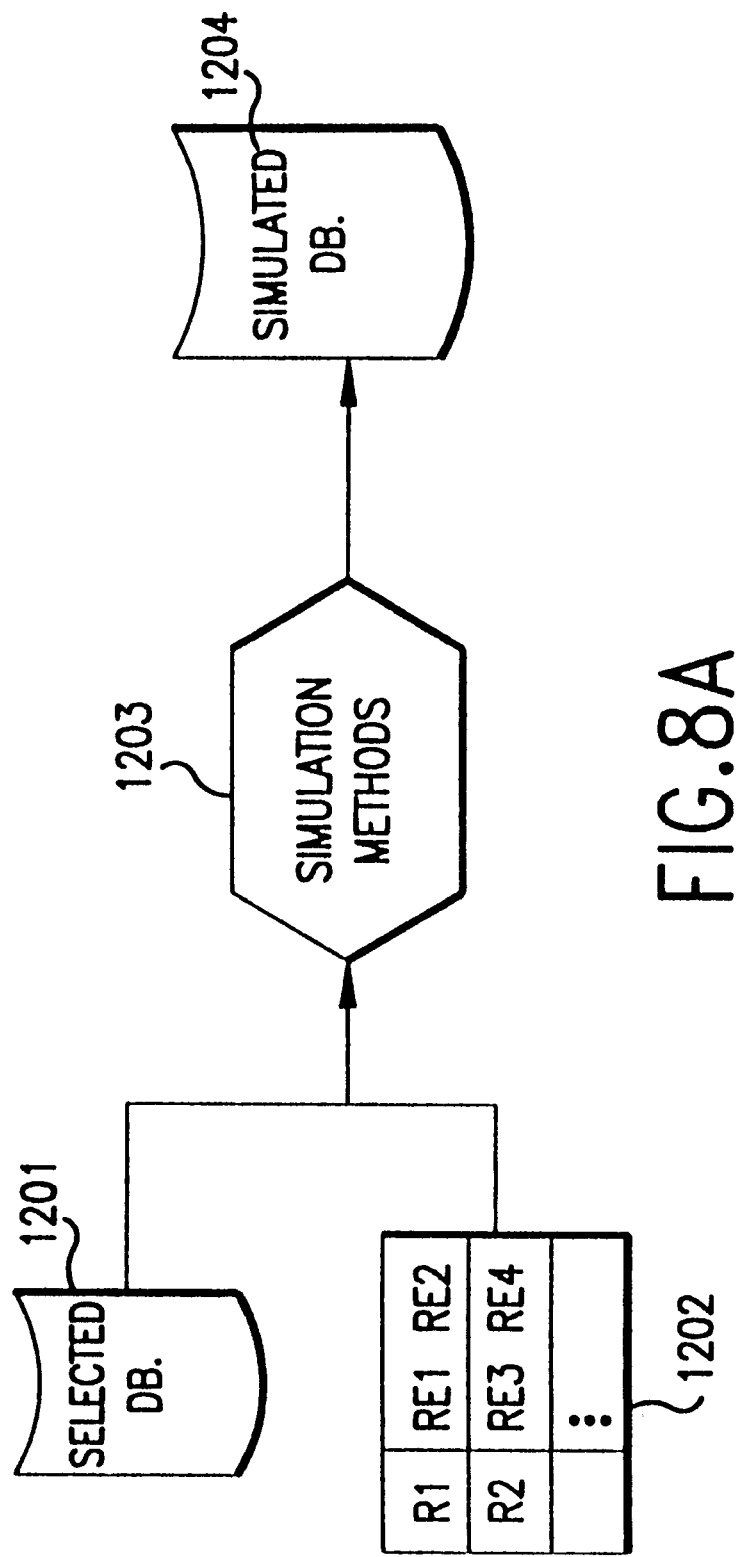

Next FIG. 8A illustrates, in general, that from the database selected to best represent the likely DNA sequences in the sample analyzed, 1201, and the description of the QEA experiment, 1202, the simulation methods, 1203, determine a pattern of simulated signals stored in a simulated database, 1204, that represents the results of the QEA experiment. The experimental simulation generates the same fragment lengths and end subsequences from the input database that will be generated in an actual experiment performed on the same sample of DNA sequences.

Alternately, the simulated pattern or database may not be needed, in which case the DNA database is searched sequence by sequence, mock digestions are performed and compared against the input signals. A simulated database is preferable if several signals need to be searched or if the same QEA experiment is run several times. Conversely, the simulated database can be dispensed with when few signals from a few experiments need to searched. A quantitative statement of when the simulated database is more efficient depends upon an analysis of the costs of the various operations and the size of DNA database, and can be performed as is well known in the computer arts. Without limitation, in the following the simulated database is described FIG. 8B illustrates an exemplary structure for the simulated database. Here, the simulated results of all the individual recognition reactions defined for the experiment are gathered into rectangular table 1210. The invention is equally adaptable to other database structures containing equivalent information; such an equivalent structure would be one, for example, where each reaction was placed in a separate table. The rows of table 1210 are indexed by the lengths of possible fragments. For example, row 1211 contains fragments of length 52. The columns of table 1210 are indexed by the possible end subsequences and probe hits, if any, in a particular experimental reaction. For example, columns 1212, 1213, and 1214 contain all fragments generated in reaction 1, R1, which have both end subsequences recognized by RE1, one end subsequence recognized by RE1 and the other by RE2, and both end subsequences recognized by RE2, respectively. Other columns relate to other reactions of the experiment. Finally, the entries in table 1210 contain lists of the accession numbers of sequences in the database that give rise to a fragment with particular length and end subsequences. For example, entry 1215 indicates that only accession number A01 generates a fragment of length 52 with both end subsequences recognized by RE1 in R1. Similarly, entry 1216 indicates that accession numbers A01 and S003 generate a fragment of length 151 with both end subsequences recognized by RE3 in reaction 2.

In alternative embodiments, the contents of the table can be supplemented with various information. In one aspect, this information can aid in the interpretation of results produced by the separation and detection means used. For example, if separation is by electrophoresis, then the detected electrophoretic DNA length can be corrected to obtain the true physical DNA length. Such corrections are well known in the electrophoretic arts and depend on such factors as average base composition and fluorochrome labels. One commercially available package for making these corrections is Gene Scan Software from Applied Biosystems, Inc. (Foster City, Calif.). In this case, each table entry for a fragment can contain additionally average base composition, perhaps expressed as percent G+C content, and the experimental definition can include primer average base composition and fluorochrome label used. For a further example, if separation is by mass spectroscopy or similar method, the additional information can be the molecular weight of each fragment and perhaps a typically fragmentation pattern. Use of other separation and detection means can suggest the use of other appropriate supplemental data.

Where alternative phasing primers are used, supplemental columns are used with RE pair in order to further identify the effective target subsequence.

Before describing how this simulated database is generated, it is useful first to describe how this database is used to predict experimental results. Returning to FIG. 7, labels are used to detect binding reaction events by subsequence recognition means to the target DNA, to allow detection after separation of the fragments by length. In an embodiment using fluorescent detection means, these labels are fluorochromes covalently attached to the primer strands of the adapters, as previously described, or to hybridization probes, if any. Typically, all the fluorochrome labels used in one reaction are simultaneously distinguishable so that fragments with all possible combinations of target subsequences can be fluorescently distinguished. For example, fragments at entry 1217 in table 1210 (FIG. 8B) occur at length 175 and present simultaneous fluorescent signals LABEL1 and LABEL2 upon stimulation, since these are the labels used with adapters which recognize ends cuts by RE1 and RE2 respectively. For a further example, in reaction 2, major row 1105 of experimental definition 1100 (FIG. 7), a fragment with ends cut by RE2 and RE3 and hybridizing with probe P will present simultaneous signals LABEL2, LABEL3, and LABEL4. Where effective target subsequences are constructed with alternative phasing primers, this lookup is appropriately modified.

Other labelings are within the scope of this invention. For example, a certain group of target subsequences can be identically labeled or not labeled at all, in which case the corresponding group of fragments are not distinguishable. In this case, if RE1 and RE3 end subsequences were identically labeled in table 1210 (FIG. 8B), a fragment of length 151 may be generated by sequence T163, A01, or S003, or any combination of these sequences. In the extreme, if silver (Ag) staining of an electrophoresis gel is used in an embodiment to detect separated fragments, then all bands will be identically labeled and only band lengths can be distinguished within one electrophoresis lane.

Thus the simulated database together with the experimental definition can be used to predict experimental results. If a signal is detected in a recognition reaction, say Rn, whose end labelings are LABEL1 and LABEL2 and whose representation of length is corrected to physical length in base pairs of L, the length L row of the simulated database is retrieved and it is scanned for Rn entries with the detected subsequence labeling, by using the column headings indicating observed subsequences and the experimental definition indicating how each subsequence is labeled. If no match is found, this fragment represents a new gene or sequence not present in the selected database. If a match is found, then this fragment, in addition to possibly being a new gene or sequence, can also have been generated by those candidate sequences present in the table entry(ies) found.

The simulated database lookup is described herein as using the physical length of a detected fragment. In cases where the separation and detection means returns an approximation to the true physical fragment length, lookup is augmented to account for such as approximation. For example, electrophoresis, when used as the separation means, returns the electrophoretic length, which depending on average base composition and labeling moiety is typically within 10% of the physical length. In this case database lookup can search all relevant entries whose physical length is within 10% of the reported electrophoretic length, perform corrections to obtain electrophoretic length, and then check for a match with the detected signal. Alternative lookup implementations are apparent, one being to precompute the electrophoretic length for all predicted fragments, construct an alternate table index over the electrophoretic length, and then directly lookup the electrophoretic length. Other separation and detection means can require corresponding augmentations to lookup to correct for their particular experimental biases and inaccuracies. It is understood that where database lookup is referred to subsequently, either simple physical lookup or augmented lookup is meant as appropriate.

If matched candidate database sequences are found, then the selected database can be consulted to determine other information concerning these sequences, for example, gene name, tissue origin, chromosomal location, etc. If an unpredicted fragment is found, this fragment can be optionally retrieved from the length separation means, cloned or sequenced, and used to search for homologues in a DNA sequence database or to isolate or characterize the previously unknown gene or sequence. In this manner this invention can be used to rapidly discover and identify new genes.

The computer methods of this invention are also adaptable to other formats of an experimental definition. For example, the labeling of the target subsequence recognition moieties can be stored in a table separate from the table defining the experimental reactions.

Now turning to the methods by which the simulated database is generated, FIG. 9 illustrates a basic method, termed herein mock fragmentation, which takes one sequence and the definition of one reaction of an experiment and produces the predicted results of the reaction on that sequence. Generation of the entire simulated database requires repetitive execution of this basic method.

Turning first to a description of mock fragmentation, the method commences at 1301 and at 1302 it inputs the sequence to be fragmented and the definition of the fragmentation reaction, in the following terms: the target end subsequences RE1 . . . REn, where n is typically 2 or 3, and the subsequences to be recognized by post PCR probes, P1 . . . Pn, where n is typically 0 or 1. Note that PCR disruption probes act as unlabeled end subsequences and are so treated for input to this method. The operation of the method is illustrated by example in FIG. 10A–F for the case RE1, RE2 and P1.

At step 1303, for each target end subsequence, the method makes a "vector of ends", which has elements which are pairs of nucleotide positions along the sequence, each pair being labeled by the corresponding end subsequence. For embodiments where end subsequences are recognized by hybridizing oligonucleotides, the first member of each pair is the beginning of a target end subsequence and the second member is the end of a target end subsequence. For embodiments where target end subsequences are recognized by restriction endonucleases, the first member of each pair is the beginning of the overhang region that corresponds to the RE recognition subsequence and the second member is the end of that overhang region. It is preferred to use REs that generate 4 bp overhangs. The actual target end subsequences are the RE recognition sequences, which are preferably 4–8 bp long.

This vector is generated by a string operation which compares the target end subsequence in a 5' to 3' direction against the input sequence and seeks string matches, that is the nucleotides match exactly. Where effective target subsequences are formed by using alternative phasing primers, it is the effective subsequences that are compared. This can be done by simply comparing the end subsequence against the input sequence starting at one end and proceeding along the sequence one base at time. However, it is preferable to use a more efficient string matching algorithm, such as the Knuth-Morris-Pratt or the Boyer-Moore algorithms. These are described with sample code in Sedgewick, 1990, *Algorithms in C*, chap. 19, Addison-Wesley, Reading, Mass.

In QEA embodiments where target subsequence are recognized with accuracy, such as the RE embodiments, the comparison of target subsequence against input sequence should be exact, that is the bases should match in a one-to-one manner. In embodiments where target subsequences are less accurately recognized, the string match should be done in a less exact, or fuzzy, manner. For example, in the PCR embodiments, a target subsequence of length T can inaccurately recognize an input sequence, also of length T,. by matching only T-n bases exactly, where n is typically 1 or 2 and is adjustable depending on experimental conditions. In this case the string operation, which generates the vector of ends, should accept partial T-n matches as well as exact matches. In this, the string operations generate the false positive matches expected from the experiments and permit these fragments to be identified. Ambiguity in the simulated database, however, increases, since more fragments leads to a greater chance of fragments of identical length and end labels.

FIG. 10A illustrates end vectors 1401 and 1402, comprising three and two ends, respectively, generated by RE1 and RE2, which are for this example assumed to be REs with a 4 bp overhang. The first overhang in vector 1401 occurs between nucleotide 10 and 14 in the input sequence.

Step 1304 of FIG. 9 merges all the end vectors for all the end subsequences and sorts the elements on the position of the end. Vector 1404 of FIG. 10B illustrates the result of this step for example end vectors 1401 and 1402.

Step 1305 of FIG. 9 then creates the fragments generated by the reaction by selecting the parts of the full input sequence that are delimited by adjacent ends in the merged and sorted end vector. Since the experimental conditions in conducting QEA should be selected such that target end subsequence recognition is allowed to go to completion, all possible ends are recognized. For the restriction endonuclease embodiments, the cutting and ligase reactions should be conducted such that all possible RE cuts are made and to each cut end a labeled primer is ligated. These conditions insure that no fragments contain internal unrecognized target end subsequences and that only adjacent ends in the merged and sorted vector define generated fragments.

Where additional information is needed for simulated database entries to adapt to inaccuracies in particular separation and detection means, such information can be collected at this step. For example, in the case of. electrophoretic separation, fragment sequence can be determined and percent G+C content computed and entered in the database along with the fragment accession number.

For the PCR embodiments, the fragment length is the difference between the end position of the second end subsequence and the start position of the first end subsequence. For RE embodiments, the fragment length is the difference between the start position of the second end subsequence and the start position of the first end subsequence plus twice the primer length (48 in the preferred primer embodiment).

FIG. 10C illustrates the exemplary fragments generated, each fragment being represented by a 4 member tuple comprising: the two end subsequences, the length, and an indicator whether the probe binds to this fragment. In FIG. 10C the position of this indicator is indicated by a '*'. Fragment 1408 is defined by ends 1405 and 1406, and fragment 1409 by ends 1406 and 1407. There is no fragment defined by ends 1405 and 1407 because the intermediate end subsequence is recognized and either fully cut in an RE embodiment or used as a fragment end priming position in a PCR embodiment. For simplicity, the fragment lengths are illustrated for the RE embodiment without the primer length addition.

Step 1306 of FIG. 9 checks if a hybridization probe is involved in the experiment. If not, the method skips to step 1309. If so, step 1307 determines the sequence of the fragment defined in step 1305. FIG. 10D illustrates that the fragment sequences fog this example are the nucleotide sequences within the input sequence that are between the indicated nucleotide positions. For example, the first fragment sequence is the part of the input sequence between positions 10 and 62. Step 1308 then checks each probe subsequence against each fragment sequence to determine whether there is any match (i.e., whether the probe has a sequence complementary enough to the fragment sequence sufficient for it to hybridize thereon). If a match is found, an indication is made in the fragment 4 member tuple. This match is done by string searching in a similar manner to that described for generation of the end vectors.

Next at step 1309 of FIG. 9, all the fragment are sorted on length and assembled into a vector of sorted fragments, which is output from the mock fragmentation method at step 1310. This vector contains the complete list of all fragments, with probe information, defined by their end subsequences and lengths that the input reaction will generate from the input sequence.

FIG. 10E illustrates the fragment vector of the example sorted according to length. For illustrative purposes, probe P1 was found to hybridize only to the third fragment 1412, where a 'Y' is marked. 'N' is marked in all the other fragments, indicating no probe binding.

The simulated database is generated by iteratively applying the basic mock fragmentation method for each sequence in the selected database and each reaction in the experimental definition. FIG. 11 illustrates a simulated database generation method. The method starts at 1501 and at 1502 inputs the selected representative database and the experimental definition with, in particular, the list of reactions and their related subsequences. Step 1503 initializes the digest database table so that lists of accession numbers may be inserted for all possible combinations of fragment length and target end subsequences. Step 1504, a DO loop, causes the iterative execution of steps 1505, 1506, and 1507 for all sequences in the input selected database.

Step 1505 takes the next sequence in the database, as selected by the enclosing DO loop, and the next reaction of the experiment and performs the mock fragmentation method of FIG. 9, on these inputs. Step 1506 adds the sorted fragment vector to the simulated database by taking each fragment from the vector and adding the sequence accession number to the list in the database entry indexed by the fragment length and end subsequences and probe (if any). FIG. 10F represents the simulated database entry list additions that would result for the example mock fragmentation reaction of FIGS. 10A–E. For example, accession number A01 is added to the accession number list in the entry 1412 at length 151 and with both end subsequences RE2.

Finally, step 1507 tests whether there is another reaction in the input experiment that should be simulated against this sequence. If so, step 1505 is repeated with this reaction. If not, the DO loop is repeated to select another database sequence. If all the database sequences have been selected, the step 1508 outputs the simulated database and the method ends at 1509.

5.4.2. QEA Experimental Design Methods

The goal of the experimental design methods is to optimize each experiment in order to obtain the maximum amount of quantitative information. An experiment is defined by its component recognition reactions, which are in turn defined by the target end subsequences recognized, probes used, if any, and labels assigned. If alternative phasing primers are used, effective target subsequences are used. Any of several criteria can be used to ascertain the amount of information obtained, and any of several algorithms can be used to perform the reaction optimization.

A preferred criteria for ascertaining the amount of information uses the concept of "good sequence." A good sequence for an experiment is a sequence for which there is at least one reaction in the experiment that produces a unique signal from that sequence, that is, a fragment is produced from that good sequence, by at least one recognition reaction, that has a unique combination of length and labeling. For example, returning to FIG. 8B, the sequence with accession number A01 is a good sequence because reaction 1 produces signal 1215, with length 52 and with both target end subsequences recognized by RE1, uniquely from sequence A01. However, sequence S003 is not a good sequence because there are no unique signals produced only from S003: reaction R2 produces signal 1216 from both A01 and S003 and signal 1219 from both Q012 and S003. Using the amount of good sequences as an information measure, the greater the number of good sequences in an experiment the better is the experimental design. Ideally, all possible sequences in a sample would be good sequences.

Further, a quantitative measure of the expression of a good sequence can simply be determined from the detected signal intensity of the fragment uniquely produced from the good sequence. Relative quantitative measures of the expression of different good sequences can be obtained by comparing the relative intensities of the signal uniquely produced from the good sequences. An absolute quantitative measure of the expression of a good sequence can be obtained by including a concentration standard in the original sample. Such a standard for a particular experiment can consist of several different good sequences known not to occur in the original sample and which are introduced at known concentrations. For example, exogenous good sequence 1 is added at a $1:10^3$ concentration in molar terms; exogenous good sequence 2 at a $1:10^4$ in molar terms; etc. Then comparison of the relative intensity of the unique signal of a good sequence in the sample with the intensities of the unique signal of the standards allows determination of the molar concentrations of the sample sequence. For example, if the good sequence has a unique signal intensity half way between the unique signal intensities of good sequences 1 and 2, then it is present at a concentration half way between the concentrations of good sequences 1 and 2.

Another preferred measure for ascertaining the amount of information produced by an experiment is derived by limiting attention to a particular set of sequences of interest, for example a set of known oncogenes or a set of receptors known or expected to be present in a particular tissue sample. An experiment is designed according to this measure to maximize the number of sequences of interest that are good sequences. Whether other sequences possibly present in the sample are good sequences is not considered. These other sequences are of interest only to the extent that the sequences of interest produce uniquely labeled fragments without any contribution from these other sequences.

This invention is adaptable to other measures for ascertaining information from an experiment. For example, another measure is to minimize on average the number of sequences contributing to each detected signal. A further measure is, for example, to minimize for each possible sequence the number of other sequences that occur in common in the same signals. In that case each sequence is linked by common occurrences in fragment labelings to a minimum number of other sequences. This can simplify making unambiguous signal peaks of interest (see infra).

Having chosen an information measure, for example the number of good sequences, for an experiment, the optimization methods choose target subsequences, and possibly probes, which optimize the chosen measure. One possible optimization method is exhaustive search, in which all subsequences in lengths less than approximately 10 are tested in all combinations for that combination which is optimum. This method requires considerable computing power, and the upper bound is determined by the computational facilities available and the average probability of occurrence of subsequences of a given length. With adequate resources, it is preferable to search all sequences down to a probability of occurrence of about 0.005 to 0.01. Upper bounds may range from 8 to 11 or 12.

A preferred optimization method is known as simulated annealing. See Press et al., 1986, *Numerical Recipes—The Art of Scientific Computing*, § 10.9, Cambridge University Press, Cambridge, U.K. Simulated annealing attempts to find the minimum of an "energy" function of the "state" of a system by generating small changes in the state and accepting such changes according to a probabilistic factor to create a "better" new state. While the method progresses, a simulated "temperature", on which the probabilistic factor depends and which limits acceptance of new states of higher energy, is slowly lowered.

In the application to the methods of this invention, a "state", denoted by S, is the experimental definition, that is the target end subsequences and hybridization probes, if any, in each recognition reaction of the experiment. The "energy", denoted E, is taken to be 1.0 divided by the information measure, so that when the energy is minimized, the information is maximized. Alternatively, the energy can be any monotomically decreasing function of the information measure. The computation of the energy is denoted by applying the function E( ) to a state.

The preferred method of generating a new experiment, or state, from an existing experiment, or state, is to make the following changes, also called moves to the experimental definition: (1) randomly change a target end subsequence in a randomly chosen recognition reaction; (2) add a randomly chosen target end subsequence to a randomly chosen reaction; (3) remove a randomly chosen target end subsequence from a randomly chosen reaction with three or more target subsequences; (4) add a new reaction with two randomly chosen target end subsequences; and (5) remove a randomly chosen reaction. If an RE embodiment of QEA is being designed, all target end subsequences are limited to available RE recognition sequences. If alternative phasing primers are used to generate effective target subsequences, all subsequences must be chosen from among such effective target subsequences that can be generated from available REs. To generate a new experimental definition, one of these moves is randomly selected and carried out on the existing experimental definition. Alternatively, the various moves can be unequally weighted. In particular, if the number of reactions is to be fixed, moves (4) and (5) are skipped. The invention is further adaptable to other moves for generating new experiments. Preferable generation methods will generate all possible experiments.

Several additional subsidiary choices are needed in order to apply simulated annealing. The "Boltzman constant" is taken to be 1.0, so that the energy equals the temperature. The minimum of the energy and temperature, denoted $E_0$ and $T_0$, respectively, are defined by the maximum of the information measure. For example, if the number of good sequences of interest is G and is used as the information measure, then $E_1$, which equals $T_0$, equals $1/G$. An initial temperature, denoted $T_1$, is preferably chosen to be 1. An initial experimental definition, or state, is chosen, either randomly or guided by prior knowledge of previous experimental optimizations. Finally, two execution parameters are chosen. These parameters define the "annealing schedule", that is the manner in which the temperature is decreased during the execution of the simulated annealing method. They are the number of iterations in an epoch, denoted by N, which is preferably taken to be 100 and the temperature decay factor, denoted by f, which is preferably taken to be 0.95. Both N and f may be systematically varied case-by-case to achieve a better optimization of the experiment definition with a lower energy and a higher information measure.

With choices for the information measure or energy function, the moves for generating new experiments, an initial state or experiment, and the execution parameters made as above, the general application of simulated annealing to optimize an experimental definition is illustrated in FIG. 13A. The information measure used in this description is the number of good sequences of interest. Any information measure, such as those previously described, may be used alternately.

The method begins at step 1701. At step 1702 the temperature is set to the initial temperature; the state to the initial state or experimental definition; and the energy is set to the energy of the initial state. At step 1703 the temperature and energy are checked to determine whether either is less than or equal to the minima for the information measure chosen, as the result of either a fortuitous initial choice or subsequent computation steps. If the energy is less than or equal to the minimum energy, no further optimization is possible, and the final experimental definition and its energy is output. If the temperature is less than or equal to the minimum temperature, the optimization is stopped. Then the inverse of the energy is the number of good sequences of interest for this experimental definition.

Step 1706 is a DO loop which executes an epoch, or N iterations, of the simulated annealing algorithm, Each alteration consists of steps 1707 through 1711. Step 1707 generates a new experimental definition, or state, $S_{new}$, according to the described generation moves. Step 1708 ascertains or determines the information content, or energy, of $S_{new}$. Step 1709 tests the energy of the new state, and, if it is lower than the energy of the current state, at step 1711, the new state and new energy are accepted and replace the current state and current energy. If the energy of the new state is higher than the energy of the current state, step 1710 computes the following function.

$$EXP[-(E-E_{new})/T]$$

This function defines the probabilistic factor controlling acceptance. If this function is less than a random chosen number uniformly distributed between 0 and 1, then the new state is accepted at step 1711. If not, then the newly generated state is discarded. These steps are equivalent to accepting a new state if the energy is not increased by an amount greater than that determined by function (4) in conjunction with the selection of a random number. Or in other words, a new state is accepted if the new information measure is not decreased by an amount greater than indirectly determined by function (4).

Finally, after an epoch of the algorithm, at step 1712 the temperature is reduced by the multiplicative factor f and the method loops back to the test at step 1703.

Using this algorithm, starting from an initial experimental definition which has certain information content, the algorithm produces a final experimental definition with a higher information content, or lower energy, by repetitively and randomly altering the experimental definition in order to search for a definition with a higher information content.

The computation of the energy of an experimental definition, or state, in step 1708 is illustrated more detail in FIG. 13B. This method starts at step 1720. Step 1721 inputs the current experimental definition. Step 1722 determines a complete digest database from this definition and a particular selected database by the method of FIG. 11. Step 1723 scans the entire digest database and counts the number of good sequences of interest. If the total number of good sequences is the measure used, the total number of good sequences can be counted. Alternatively, other information measures may be applied to the digest database. Step 1724 computes the energy as the inverse of the information measure. Alternatively, another decreasing function of the information content may be used as the energy. Step 1725 outputs the energy, and the method ends at step 1726.

5.4.3. QEA Ambiguity Resolution

In one utilization of this invention two related tissue samples can be subject to the same experiment, perhaps consisting of only one recognition reaction, and the outcomes compared. The two tissue samples may be otherwise identical except for one being normal and the other diseased, perhaps by infection or a proliferative process, such as hyperplasia or cancer. One or more signals may be detected in one sample and not in the other sample. Such signals might represent genetic aspects of the pathological process in one tissue. These signals are of particular interest.

The candidate sequences that can produce a signal of interest are determined, as previously described, by look-up in the digest database. The signal may be produced by only one sequence, in which case it is unambiguously identified. However, even if the experiment has been optimized, the signal may be ambiguous in that it may be produced by several candidate sequences from the selected database. A signal of interest may be made unambiguous in several manners which are described herein.

In a first manner of making unambiguous assume the signal of interest is produced by several candidate sequences all of which are good sequences for the particular experiment. Then which sequences are present in the signal of interest can be ascertained by determining the quantitative presence of the good sequences from their unique signals. For example, referring to FIG. 8B, if the signal 1217 of length 175 with the labeling 1213 is of interest, the sequences actually present in the signal can be determined from the quantitative determination of the presence of signals 1215 and 1218. Here, both the possible sequences contributing to this signal are good sequences for this experiment.

The first manner of making unambiguous can be extended to the case where one of the sequences possibly contributing to a signal is not a good sequence. The quantitative presence of all the possible good sequences can be determined from the quantitative strength of their unique signals. The presence of the remaining sequence which is not a good sequences can be determined by subtracting from the quantitative presence of the signal of interest the quantitative presences of all the good sequences.

Further extensions of the first manner can be made to cases where more than one of the possible sequences is not a good sequences if the sequences which are not good appear as contributors to further signals involving good sequences in a manner which allows their quantitative presences to be determined. For example, suppose signal 1219 is of interest, where both possible sequences are not good sequences. The quantitative presence of sequence Q012 can be determined from signals 1220 and 1218 in the manner previously outlined. The quantitative presence of sequence S003 can be determined from signals 1216 and 1215. Thereby, the sequences contributing to signal 1219 can be determined. More complex combinations can be similarly made unambiguous.

An alternative extension of the first manner of making unambiguous is by designing a further experiment in which the possible sequences contributing to a signal of interest are good sequences even if they were not originally so. Since there are approximately 50 suitable REs that can be used in the RE embodiment of QEA (Section 6.2), there are approximately 600 RE reaction pairs that can be performed, assuming that half of the theoretical maximum of 1,250 (50×50/2=1,250) are not useable. Since most RE pairs produce on the average of 200 fragments and standard electrophoretic techniques can resolve at least approximately 500 fragment lengths per lane, the RE QEA embodiment has the potential of generating over 100,000 signals (500×200=100,000). The number of possible signals is further increased by the use of reactions with three or more REs and by the use of labeled probes. Further, since the average complex human tissue, for example brain, is estimated to express no more than approximately 25,000 genes, there is a 4 fold excess of possible signals over the number of possible sequences in a sample. Thus it is highly likely that for any signal of interest, a further experiment can be designed and optimized for which all possible candidates of the signal of interest are good sequences. This design can be made by using the prior optimization methods with an information measure the sequences of interest in the signal of interest and starting with an extensive initial experimental definition including many additional reactions. In that manner, any signal of interest can be made unambiguous.

A second manner of making unambiguous is by automatically ranking the likelihood that the sequences possibly present in a signal of interest are actually present using information from the remainder of the experimental reactions. FIG. 14 illustrates a preferred ranking method. The method begins at step 1801 and at step 1802 inputs the list of possible accession numbers in a signal of interest, the experimental definition, and the actual experimental results. DO-loop 1803 iterates once for each possible accession number. Step 1804 performs a simulated experiment by the method illustrated in FIG. 11 in which, however, only the current accession number is acted on. The output is a single sequence digest table, such as illustrated in FIG. 10F.

Step 1805 determines a numerical score of ranking the similarity of this digest table to the experimental results. One possible scoring metric comprises scanning the digest table for all fragment signals and adding 1 to the score if such a signal appears also in the experimental results and subtracting 1 from the score if such signal does not appear in the experimental results. Alternate scoring metrics are possible. For example, the subtraction of 1 may be omitted.

Step 1806 sorts the numerical scores of the likelihood that each possible accession number is actually present in the sample. Step 1807 outputs the sorted list and the method ends at step 1808.

By this method likelihood estimates of the presence of the various possible sequences in a signal of interest can be determined.

5.5. Colony Calling

The colony calling embodiment recognizes and classifies single, individual genes or DNA sequences by determining the presence or absence of target subsequences. No length information is determined. This embodiment is directed to gene determination and classification of arrayed samples or colonies, where each sample or colony contains or expresses only one sequence or gene of interest and is perhaps prepared from a tissue cDNA library. The presence or absence of target subsequences in a colony is determined by use of labeled hybridization recognition means, each of which uniquely binds to one target subsequence. It is preferable that this binding be highly specific and reproducible. Each sample or colony, or an array of samples or colonies, is assayed for the contained sequence by determining which of the set of probes recognizes and thus hybridizes to target subsequences in the sample(s) or colony(ies). Each sample is then characterized by a hash code, each bit of which indicates which probes recognized subsequences, or hits, in a particular sample. The sequence or gene in a sample is determined from the hash code by computer implemented methods.

The choice of the target subsequences is important. For economical and rapid assay, the size of the set of recognition means should be as small as possible, preferably less than 50 elements and more preferably from 15 to 25 elements. Further, it is most preferable that all possible sequences or genes are recognized and uniquely determined. It is preferable that 90 to 95% of all possible sequences be recognized, with each sequence being indistinguishable from, or ambiguous with, at most one or two other sequences. Therefore, each target subsequence preferably occurs frequently enough to minimize the number of different recognition means needed. For example, it is not practical for this invention, directed to rapid gene classification, if each probe recognized only a few genes and therefore thousands of probes were needed. However, each target subsequence preferably does not occur so frequently that its presence conveys little information. For example, a probe recognizing every gene conveys no information.

The optimal choice is for each target subsequence to have a probability of occurrence in all the genes or sequences that can appear in a sample or colony of approximately 50%; a preferable choice is a probability of occurrence between 10 and 50%. Typically for human cDNA libraries, target subsequences of length 4 to 6 meet this condition, as longer sequences occur too infrequently to make useful hash codes. Additionally, the presence of one target subsequence is preferably independent of the presence of any other target subsequence in the same sequence or gene. These two criteria ensure that a hash code for a sample, consisting of indications of which target subsequences are present, is maximally likely to represent a unique gene or DNA sequence with minimum of wasted code words not specifying any gene. Such a hash code is an efficient representation of sequences or genes.

The maximal number of genes or sequences that can be represented by a hash code is $2^n$, where n is the number of target subsequences. A simple test to determine whether the target subsequences occur frequently enough in the expected gene library is made by comparing the actual probabilities of the two hash codes that have all target subsequences either present or absent to the ideal probabilities of these codes. If p is the probability that any target subsequence occurs in a given sequence in the library, then probability that none of the target subsequences occur in a random gene is $(1-p)^n$. The closer the ratio $(1-p)^n/2^{-n}$ is to 1 the more efficient is the code. Similarly, the closer $p^n/2^{-n}$, the ratio of the probabilities that all the target subsequences are present to the ideal probability conveying maximum information, is to 1 the more efficient is the code. We see the optimal p is close to $2^{-1}$.

The preferred method of selecting target subsequences meeting the probability of occurrence and independence criteria is to use a database containing sequences generally expected to be present in the samples to be analyzed, for example human GenBank sequences for human tissue derived samples. From a sequence database, oligomer frequency tables are compiled containing the frequencies of, preferably, all 4 to 8-mers. From these tables, candidate subsequences with the desired probability of occurrence are selected. Each candidate target subsequence is then checked for independent occurrence, by, for example, checking that the conditional probability for a hit by any selected pair of candidates is approximately the product of the probabilities of the individual candidate hit probabilities. Candidate target subsequences meeting both occurrence and independence criteria are possible target subsequences. A sufficient number, typically 20, of any of these subsequences can be selected as target subsequences for a hash code.

Preferably, but optionally, the initially set of target subsequences can be optimized, using information on the actual occurrences of the initially selected target subsequences in the sequence database, resulting in a set of target subsequences selected which recognizes a maximum number of genes with a minimum number of sequences and with a minimum amount of recognition ambiguity. Alternatively, this optimization can also be performed on a sub-set of the database comprised of sequences or genes of particular biological or medical interest, for example, the set of all oncogenes or growth factors. In this manner, fewer target subsequences can be chosen which distinguish more efficiently among a set of sequences or genes of particular interest and distinguish that set of genes from the sequences of the remainder of the sample.

This combinatorial optimization problem is computationally intensive to solve exactly. A number of approximate techniques can be used to obtain efficient nearly optimal solutions. The preferred but not limiting technique is to use simulated annealing (Press et al., 1986, *Numerical Recipes—The Art of Scientific Computing*, § 10.9, Cambridge University Press, Cambridge, U.K.). The experimental design and optimization are described in detail in the following section.

Example 6.6 illustrates the results of the simulated annealing optimization method. Simulated annealing generally produces a choice of subsequences that achieve the same resolution while using approximately 20% fewer total sequences than a selection guided only by the probability principles previously described. This level of optimization is likely to improve with larger and less redundant databases that represent longer genes.

An alternative to using single target subsequences is to use sets of target subsequences, recognized by sets of identically labeled hybridization probes, to generate one presence or absence indication for the hash code. In this alternative, sets of longer target subsequences would be chosen such that the presence of any target subsequence in the set is a presence indication. Absence means no element of the set is present. If the sets are chosen so that their probability of presence in a single sequence is near 50%, preferably from 10 to 50%, and the presence or absence of one set is independent of the presence or absence of any other set, such sets can be used to construct codes equally well as single subsequences. A resulting code will be efficient and can be further optimized by simulated annealing, as for single target subsequence codes. Target sets of longer subsequences are preferable where experimental recognition of shorter subsequences is less specific and reproducible, as for example is true where short DNA oligomers are used as hybridization probes for recognition. As a further alternative, a code can consist of presence or absence indications of mixed target sets of subsequences and single target subsequences.

Probes for a target subsequence are preferably PNA oligomers, or less preferably DNA oligomers, which hybridize to the subsequence of interest. Use of sets of degenerate DNA oligomers to more specifically and reliably hybridize to short DNA subsequences has been described in relation to the PCR implementation of the QEA method. The use of PNAs is preferred in the colony calling embodiment since PNA oligomers, due to their more favorable hybridization energetics, more specifically and reliably hybridize to shorter complementary DNA subsequences than do DNA oligomers. Reliable hybridization occurs for PNA 6 to 8-mers and longer. Probing shorter subsequences preferably uses fully degenerate sets of PNA oligomers, as is the case for DNA oligomers.

PNAs are even more preferable when, in the alternative, the hash code comprises presence or absence indication of target sets of longer subsequences. In this case, many more DNA probes are generally required than PNA probes. As PNA 6 to 8-mers reliably hybridize, target sets can consist of subsequences of length 6 to 8. Since DNA oligomers of this length may not reliably hybridize, each subsequence in the set must in turn be represented by a further degenerate set of DNA oligomers, requiring thereby a set of sets.

The experimental method of colony calling comprises three principal steps: first, arraying cDNA libraries on filters or other suitable substrates; second, PNA hybridization and detection, alternatively DNA hybridization can be used; and third, interpreting the resulting hash code to determine the sequence in the sample.

The first step, which can be omitted if arrayed cDNA libraries are already available, is constructing and arraying cDNA libraries. Any methods known in the art may be used. For example, cDNA libraries from normal or diseased tissues can be constructed according to Example 6.3. Alternatively, the human cDNA libraries constructed by M. B. Soares and colleagues are available as high density arrays on filters and can be used for the practice of this method. See Soares et al., 1994, Proc. Natl. Acad. Sci. USA, 91:9228–32. The ability to spot up to thousands of cDNA clones or colonies on filters suitable for hybridization is an established technology. This service is now provided by several companies, including the preferred supplier Research Genetics (Huntsville, Ala.). The protocol of Example 6.7 can be used to generate these arrays from cDNA libraries.

The second step is probe (e.g. PNA) hybridization and detection. Fluorescently labeled PNA oligomers are available from Perseptive Biosystems (Bedford, Mass.) or can be synthesized. PNAs are designed to be complementary to the chosen target subsequences and to have a maximum number of distinguishable labels for simultaneous hybridization with multiple oligomers. PNA hybridization is performed according to standard protocols developed by the manufacturer and detailed in Example 6.7. Detection of the PNA signals uses optical spectrographic means to distinguish fluorochrome emissions similar to those used in DNA analysis instruments, but appropriately modified to recognize spots on filters as opposed to linearly arrayed bands.

The third step, interpretation of the hash code, is done by the computer implemented method described in the following section.

In an alternative embodiment, the intensity of the detected hybridization signal indicates the number of times the probe binds to the sample sequence. In this manner the number of recognized target subsequences present in the sample can be determined. This information can be used to more precisely classify of identify a sample.

5.6. CC Analysis and Design Methods

The colony calling ("CC") computer implemented methods are similar to the QEA computer methods. As for the QEA case, the experimental analysis methods are described before the experimental design methods.

5.6.1. CC Experimental Analysis Methods

The analysis methods make use of a mock experiment concept. First, a database is selected to represent possible sequences in the sample by the same methods as described for QEA analysis. These are illustrated and described with reference to FIG. 6A. For cc, an experimental definition is simply a list of $N_p$ target subsequences, where $N_p$ is preferably between 16 and 20. Next, a mock experiment generates one hash code for each sequence in the selected database, each hash code being a string of $N_p$ binary digits wherein the n'th digit is a 1 (0) if the n'th target subsequence does (does not) hybridize with the sequence. The results of all the mock experiments determine the pattern of hash codes expected. This pattern is output in a code table of all possible hash codes in which, for each hash code, there is a list of all accession numbers of sequences with this code.

This method is illustrated in more detail in FIG. 15. The method starts at step 1901 and at step 1902 it inputs a selected database and on experimental definition consisting of $N_p$ target subsequences. Step 1903 initializes a table which for each of the $2^{N_p}$ hash codes can contain a list of possible accession numbers which have this hash code. Step 1904 is a DO loop which iterates through all sequences in the database. For a particular sequence, step 1905 checks for each target subsequence whether that subsequence hybridizes to the sequence. This is implemented by string matching in a manner similar to step 1303 of FIG. 9. A binary hash code is constructed from this hybridization information, and step 1906 adds the accession number of the sequence to the list of accession numbers associated with this hash code in the code table. Step 1907 outputs the code table and the method ends at step 1908.

Having built a pattern of simulated hash code in a code table, analysis of an experiment requires only simple table look-up. A colony is hybridized with each of the $N_p$ recognition means for the target subsequences. The results of the hybridization are used to construct a resulting hash code. This code table for this hash code entry then contains a list of sequence accession numbers that are possible candidates for the sample sequence. If the list contains only one element, then the sample has been uniquely identified. If the list contains more than one element, the identification is ambiguous. If the list is empty, the sample is not in the selected database and may possibly be a previously unknown sequence.

Alternately, as for QEA experimental analysis, a code table can be dispensed with if only a few hash codes need to be looked up from only a few experiments. Then the DNA database is scanned sequence by sequence for those sequences generating the hash code of interest. If many hash codes from many experiments need to be analyzed, a code table is more efficient. The quantitative decision of when to build a code table depends on the costs of the various operations and the size of DNA database, and can be performed as is well known in the computer arts. Without limitation, this description is built on the use of a code table.

For those embodiments where the recognition means can each recognize a subset of target subsequences, code table construction must be modified accordingly. Such embodiments, for example, can involve DNA oligomer probes which due to their length can hybridize with an intended target subsequences and those subsequences which differ by 1 base pair from the intended target. In such embodiments, step 1905 checks whether each member of such a set of target subsequences is found in the sample sequence. If any member is found in the sequence, then this information is used to construct the hash code.

5.6.2. CC Experimental Design Methods

As for QEA, the goal of CC experimental design is to maximize the amount of information from a CC hybridization experiment. This is also performed by defining an information measure and choosing an optimization method which maximizes this measure.

The preferred information measure is the number of occupied hash codes. This is equivalent to minimizing the number of accession numbers which can result in a given hash code. In fact for $N_p$ greater than about 17 to 18, that is for $2^{N_p}$ greater than the number of expressed human genes (about 100,000), maximizing the number of occupied hash codes can result in each hash code representing a single sequence. Such a unique code contains the maximum amount of information. The invention is adaptable to other CC information measures. For example, if only a subset of the possible sequences are of interest, an appropriate measure would be the number of such sequences which are uniquely represented by a hash code. As for QEA, these are sequences of interest.

One optimization algorithm is exhaustive search. In exhaustive search, all subsequences of length less than approximately 10 are tried in all combinations in order to find the optimum combination producing the best hash code according to the chosen information measure. This method is inefficient. The preferred algorithm for optimizing the information from an experiment is simulated annealing. This is performed by the method illustrated and described with respect to FIG. 13A. For CC, the following preferred choices are made.

The energy is taken to be 1.0 divided by the information content; alternatively, any monotonically decreasing function of the information content can be used. The energy is determined by performing the mock experiment of FIG. 15 using a particular experimental definition and then applying the measure to the resulting code table. For example, if the number of occupied hash codes is the information measure, this number can be computed by simply scanning the code table and counting the number of table entries with non-empty accession number lists. The Boltzman constant is again taken to be 1 so that the temperature equals the energy. The initial temperature is preferably 1.0. The minimum energy and temperature, $E_0$ and $T_0$, respectively, are determined by the information measure. For example, with the prior choices for energy function and information measure, $E_0$, which equals $T_0$, is 1.0 divided by the number of sequences in the selected database.

The method of generating a new experimental definition from an existing definition is to pick randomly one target subsequence and to perform one of the following moves: (1) randomly modifying one or more nucleotides; (2) adding a random nucleotide; and (3) removing a random nucleotide. A modification is discarded if it results in two identical target subsequences. Further, it is desirable to discard a modification if the resulting subsequence has an extreme probability of binding to sequences in the database. For example, if the modified subsequence binds with a probability less than approximately 0.1 or more than approximately 0.5 to sequences in the selected database, it should be discarded. To generate a new experiment, one of these moves is randomly selected and carried out on the existing experimental definition. Alternatively, the various moves can be unequally weighted. The invention is further adaptable to other methods of generating new experiments. Preferably, generation methods used will randomly generate all possible experiments. An initial experimental definition can be picked by taking $N_p$ randomly chosen subsequences or by using subsequences from prior optimization.

Finally, the two execution parameters defining the "annealing schedule", that is the manner in which the temperature is decreased during the execution of the simulated annealing method, are defined and chosen as in the QEA case. The number of iterations in an epoch, denoted by N, is preferably taken to be 100 and the temperature decay factor, denoted by f, is preferably taken to be 0.95. Both N and f may be systematically varied case-by-case to achieve a better experimental definition with lower energy and a higher information measure.

With these choices the simulated annealing optimization method of FIG. 13A can be performed to obtain an optimized set of target subsequences. To determine an optimum $N_p$, different initial $N_p$ can be selected, the prior design optimization performed, and the results compared. The Np with the maximum information measure is optimum for the selected database.

5.6.3. CC Quantitative Alternative

To make use of quantitative detection information the pattern of simulated hash codes stored in the code table is augmented with additional information. For each hash code in the table and each sequence giving rise to that hash code, this additional information comprises recording the number of times each target subsequence is found in such a sequence. These numbers are simply determined by scanning the entire sequence and counting the number of occurrences of each target subsequence.

An exemplary method to perform hash code look up in this augmented table is to first find the sequences giving rise to a particular hash code as a binary number, and second to pick from these the most likely sequence as that sequence having the most similar pattern of subsequence counts to the detected quantitative hybridization signal. An exemplary method to determine such similarity is to linearly normalize the detected signal so that the smallest hybridization signal is 1.0 and then to find the closest sequence by using a Euclidean metric in an n-dimensional code space.

For CC experimental design, each pattern of subsequence counts may alternatively be considered as a distinct code entry for evaluation of an information measure. This is instead of considering each hash code alone a distinct entry.

5.7. Apparatus for Performing the Methods of the Invention

The apparatus of this invention includes means for performing the recognition reactions of this invention in a preferably automated fashion, for example by the protocols of § 6.4.3, and means for performing the computer implemented experimental analysis and design methods of this invention. Although the subsequent discussion is directed to embodiments of apparatus for the QEA embodiments of this invention, similar apparatus is adaptable to the CC embodiments. Such adaption includes using, in place of the corresponding components for the QEA embodiments, automatic laboratory instruments appropriate for making and hybridizing arrays of clones and for reading the results of the hybridizations, and using programs implementing the computer analysis and design methods for the CC embodiments described in § 5.6.

FIG. 12A illustrates an exemplary apparatus for the QEA embodiments of this invention, and with the described adaption, also for the CC embodiments of this invention. Computer 1601 can be, alternatively, a UNIX based work station type computer, an MS-DOS or Windows based personal computer, a Macintosh personal computer, or another equivalent computer. In a preferred embodiment, computer 1601 is a PowerPC™ based Macintosh computer with software systems capable of running both Macintosh and MS-DOS/Windows programs.

FIG. 12B illustrates the general software structure in RAM memory 1650 of computer 1601 in a preferred embodiment. At the lowest software level is Macintosh operating system 1655. This system contains features 1656 and 1657 for permitting execution of UNIX programs and MS-DOS or Windows programs alongside Macintosh programs in computer 1601. At the next higher software level are the preferred languages in which the computer methods of this invention are implemented. LabView 1658, from National Instruments (Dallas, Tex.), is preferred for implementing control routines 1661 for the laboratory instruments, exemplified by 1651 and 1652, which perform the recognition reactions and fragment separation and detection. C or C++ languages 1659 are preferred for implementing experimental routines 1662, which are described in §§ 5.4 and 5.6. Less preferred but useful for rapid prototyping are various scripting languages known in the art. Power-Builder 1660, from Sybase (Denver, Colo.), is preferred for implementing the user interfaces to the computer implemented routines and methods. Finally, at the highest software level are the programs implementing the described computer methods. These programs are divided into instrument control routines 1661 and experimental analysis and design routines 1662. Control routines 1661 interact with laboratory instruments, exemplified by 1651 and 1652, which physically perform the QEA and CC protocols. Experimental routines 1662 interact with storage devices, exemplified by devices 1654 and 1653, which store DNA sequence databases and experimental results.

Returning to FIG. 12A, although only one processor is illustrated, alternatively, the computer methods and instrument control interface can be performed on a multiprocessor or on several separate but linked processors, such that instrument control methods 1661, computational experimental methods 1661, and the graphical interface methods can be on different processors in any combination or subcombination.

Input/output devices include color display device 1620 controlled by a keyboard and standard mouse 1603 for output display of instrument control information and experimental results and input of user requests and commands. Input and output data are preferably stored on disk devices such as 1604, 1605, 1624, and 1625 connected to computer 1601 through links 1606. The data can be stored on any combination of disk devices as is convenient. Thereby, links 1606 can be either local attachments, whereby all the disks can be in the computer cabinet(s), LAN attachments, whereby the data can be on other local server computers, or remote links, whereby the data can be on distant servers.

Instruments 1630 and 1631 exemplify laboratory devices for performing, in a partly or wholly automatic manner, the QEA recognition reactions. These instruments can be, for example, automatic thermal cyclers, laboratory robots, and controllable separation and detection apparatus, such as is found in the applicants' copending U.S. patent application Ser. No. 08/438,231 filed May 9, 1995. Links 1632 exemplify control and data links between computer 1601 and controlled devices 1631 and 1632. They can be special buses, standard LANs, or any suitable link known in the art. These links can alternatively be computer readable medium or even manual input exchanged between the instruments and computer 1601. Outline arrows 1634 and 1635 exemplify the physical flow of samples through the apparatus for performing experiments 1607 and 1613. Sample flow can be either automatic, manual, or any combination as appropriate. In alternative embodiments there may be fewer or more laboratory devices, as dictated by the current state of the laboratory automation art.

On this complete apparatus, a QEA experiment is designed, performed, and analyzed, preferably in a manner as automatic as possible. First, a QEA experiment is designed, according to the methods specified in § 5.4.2 as implemented by experimental routines 1662 on computer 1601. Input to the design routines are databases of DNA sequences, which are typically representative selected database 1605 obtained by selection from input comprehensive sequence database 1604, as described in § 5.4.1. Alternatively, comprehensive DNA databases 1604 can be used as input. Database 1604 can be local to or remote from computer 1601. Database selection performed by processor 1601 executing the described methods generates one or more representative selected databases 1605. Output from the experimental design methods are tables, exemplified by 1609 and 1615, which, for a QEA RE embodiment, specify the recognition reaction and the REs used for each recognition reaction.

Second, the apparatus performs the designed experiment. Exemplary experiment 1607 is defined by tissue sample 1608, which may be normal or diseased, experimental definition 1609, and physical recognition reactions 1610 as defined by 1609. Where instrument 1630 is a laboratory robot for automating reaction, computer 1601 commands and controls robot 1630 to perform reactions 1610 on cDNA samples prepared from tissue 1608. Where instrument 1631 is a separation and detection instrument, the results of these reactions are then transferred, automatically or manually, to 1631 for separation and detection. Computer 1601 commands and controls performance of the separation and receives detection information. The detection information is input to computer 1601 over links 1632 and is stored on storage device 1624, along with the experimental design tables and information on the tissue sample source for processing. Since this experiment uses, for example, fluorescent labels, detection results are stored as fluorescent traces 1611.

Experiment 1613 is processed similarly along sample pathway 1633, with robot 1630 performing recognition reactions 1616 on cDNA from tissue 1608 as defined by definition 1615, and device 1631 performing fragment separation and detection. Fragment detection data is input by computer 1601 and stored on storage device 1625. In this case, for example, silver staining is used, and detection data is image 1617 of the stained bands.

During experimental performance, instrument control routines 1661 provide the detailed control signals needed by instruments 1630 and 1631. These routines also allow operator monitoring and control by displaying the progress of the experiment in process, instrument status, instrument exceptions or malfunctions, and such other data that can be of use to a laboratory operator.

Third, interactive experimental analysis is performed using the database of simulated signals generated by analysis and design routines 1662 as described in §§ 5.4.2 and 5.4.3. Simulated database 1612 for experiment 1607 is generated by the analysis methods executing on processor 1601 using as input the appropriate selected database 1605 and experimental definition 1609, and is output in table 1612. Similarly table 1618 is the corresponding simulated database of signals for experiment 1613, and is generated from appropriate selected database 1605 and experimental definition 1615. A signal is made unambiguous by experimental routines 1662 that implement the methods described in § 5.4.3.

Display device 1602 presents an exemplary user interface for the data generated by the methods of this invention. This user interface is programmed preferably by using the Powerbuilder display front end. At 1620 are selection buttons which can be used to select the particular experiment and the particular reaction of the experiment whose results are to be displayed. Once the experiment is selected, histological images of the tissue source of the sample are presented for selection and display in window 1621. These images are typically observed, digitized, and stored on computer 1601 as part of sample preparation. The results of the selected reaction of the selected experiment are displayed in window 1622. Here, a fluorescent trace output of a particular labeling is made available. Window 1622 is indexed by marks 1626 representing the possible locations of DNA fragments of successive integer lengths.

Window 1623 displays contents from simulated database 1612. Using, for example, mouse 1603, a particular fragment length index 1626 is selected. The processor then retrieves from the simulated database the list of accession numbers that could generate a peak of that length with the displayed end labeling. This window can also contain further information about these sequences, such as gene name, bibliographic data, etc. This further information may be available in selected databases 1605 or may require queries to the complete sequence database 1604 based on the accession numbers. In this manner, a user can interactively inquire into the possible sequences causing particular results and can then scan to other reactions of the experiment by using buttons 1620 to seek other evidence of the presence of these sequences.

It is apparent that this interactive interface has further alternative embodiments specialized for classes of users of differing interests and goals. For a user interested in determining tissue gene expression, in one alternative, a particular accession number is selected from window 1623 with mouse 1603, and processor 1601 scans the simulated database for all other fragment lengths and their recognition reactions that could be produced by this accession number. In a further window, these lengths and reactions are displayed, and the user allowed to select further reactions for display in order to confirm or refute the presence of this accession number in the tissue sample. If one of these other fragments are generated uniquely by this sequence (a "good sequence", see supra), that fragment can be highlighted as of particular interest. By displaying the results of the generating reaction of that unique fragment, a user can quickly and unambiguously determine whether or not that particular accession number is actually present in the sample.

In another interface alternative, the system displays two experiments side by side, displaying two histological images 1621 and two experimental results 1622. This allows the user to determine by inspection signals present in one sample and not present in the other. If the two samples were diseased and normal specimens of the same tissue, such signals would be of considerable interest as perhaps reflecting differences due to the pathological is process. Having a signal of interest, preferably repeatable and reproducible, a user can then determine the likely accession numbers causing it by invoking the previously described interface facilities. In a further elaboration of this embodiment, system 1601 can aid the determination of signals of interest by automating the visual comparison by performing statistical analysis of signals from samples of the same tissue in different states. First, signals reproducibly present in tissue samples in the same state are determined, and second, differences in these reproducible signals across samples from the several states are compared. Display 1602 then shows which reproducible signals vary across the states, thereby guiding the user in the selection of signals of interest.

The apparatus of this invention has been described above in an embodiment adapted to a single site implementation, where the various devices are substantially local to computer 1601 of FIG. 12A, although the various links shown could also represent remote attachments. An alternative, explicitly distributed embodiment of this apparatus is illustrated in FIG. 12C. Shown here are laboratory instruments 1670, DNA sequence database systems 1684, and computer systems 1671 and 1673, all of which cooperate to perform the methods of this invention as described above.

These systems are interconnected by communication medium 1674 and its local attachments 1675, 1676, and 1677 to the various systems. This medium may be any dedicated or shared or local or remote communication medium known in the art. For example, it can be a "campus" LAN network extending perhaps a few kilometers, a dedicated wide area communication system, or a shared network, such as the Internet. The system local attachments are adapted to the nature of medium 1674.

Laboratory instruments 1670 are commanded by computer system 1671 to perform the automatable steps of the recognition reactions, separation of the reaction results, and detection and trans-mission of resulting signals through link 1672. Link 1672 can be any local or remote link known in the art that is adapted to instrument control, and may even be routed through communication medium 1674.

DNA sequence database systems 1684 with various sequence databases 1685 may be remote from the other systems, for example, by being directly accessed at their sites of origin, such as Genbank at Bethesda, Md. Alternatively, parts or all of these databases may be periodically downloaded for local access by computer systems 1671 and 1672 onto such storage devices as discs or CD-ROMs.

Computer system 1671, including computer 1681, storage 1682, and display 1683, can perform various methods of this invention. For example, it can perform solely the control routine for control and monitoring of instrument system 1670, whereby experimental design and analysis are performed elsewhere, as at computer system 1673. In this case, system 1671 it would typically be operated by laboratory technicians. Alternatively, system 1671 can also perform experimental designs, which meet the requirements of remote users of sample analysis information. In another alternative, system 1671 can carry out all the computer implemented methods of this invention, including final data display, in which case it would be operated by the final users of the analysis information.

Computer system 1673, including computer 1678, storage 1679, and display 1680, can perform a corresponding range of functions. However, typically system 1673 is remotely located and would be used by final users of the DNA sample information. Such users can include clinicians seeking information to make a diagnosis, grade or stage a disease, or guide therapy. Other users can include pharmacologists seeking information useful for the design or improvement of drugs. Finally, other users can include researchers seeking information useful to basic studies in cell biology, developmental biology, etc. It is also possible that a plurality of computer systems 1673 can be linked to laboratory system 1670 and control system 1671 in order to provide for the analysis needs of a plurality of classes of users by designing and causing the performance of appropriate experiments.

It will be readily apparent to those of skill in the computer arts that alternative distributed implementations of the apparatus of this invention, along with alternative functional allocations of the computer implemented methods to the various distributed systems, are equally possible.

All the computer implemented methods of this invention can be recorded for storage and transport on any computer readable memory devices known in the art. For example, these include, but are not limited to, semiconductor memories—such as ROMs, PROMs, EPROMS, EEPROMS, etc. of whatever technology or configuration—magnetic memories—such as tapes, cards, disks, etc of whatever density or size—optical memories—such as optical read-only memories, CD-ROM, or optical wirteable memories—and any other computer readable memory technologies.

Also, although this apparatus has been described primarily with reference to QEA analysis of human tissue samples, the laboratory instruments and associated control, design, and analysis computer systems are not so limited.

They are also adaptable to performing the CC embodiment of this invention and to the analysis of other samples, such as from animal models or in vitro cultures.

The invention is further described in the following examples which are in no way intended to limit the scope of the invention.

EXAMPLES 6.1. Subsequence Hit and Length Information

This example illustrates QEA signals generated by a PCR embodiment. From the October 1994 GenBank database, 12,000 human first continuous coding domain sequences ("CDS") were selected. This selection resulted in pool of sequences with a bias toward shorter genes, the average length of the selected CDSs being 1000 bp instead of the typical coding sequence length of 1800–2000 bp, and with no guarantee that sequences were not be repeated in the selection. From this set, tables containing the probability of occurrence of all 4 to 6-mer sequences were constructed.

Then Eqns. 1 and 2 were solved for N=12,000 and L=1,000 resulting in p=0.17 and M=108. Five 6-mer target subsequences with this probability of occurrence were chosen from the 6-mer tables and grouped into four pairs: CAGATA-TCTCAC, CAGATA-GGTCTG, CAGATA-GCTCAA CAGATA-CACACC. The pool of selected CDSs were then scanned against these four pairs of target subsequences to determine whether any pair hit and if so the length between the hits.

Figure 1:
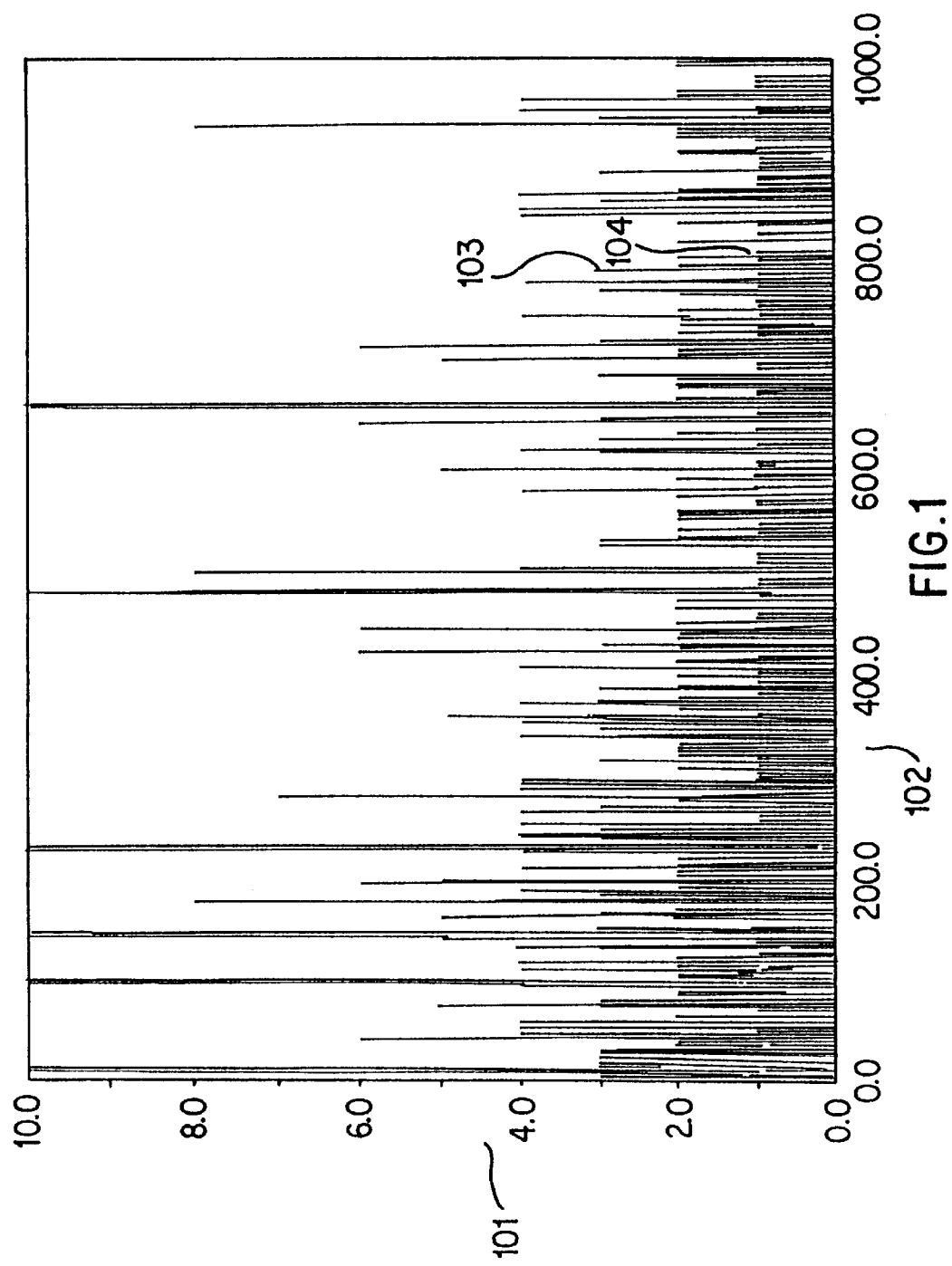

The histogram of FIG. 1 presents the results of this scan. Along axis 102 is the relative length between subsequence pair hits. This would be the length observed in a gel separation of the amplified fragments of a QEA PCR reaction using these target subsequences. Along axis 101 is the number hits at any given length. For example, spike 103 at a length of approximately 800 base pairs represents a fragment length having three hits. Multiple hits at one length may occur either because several CDSs have one target subsequence pair spaced this length, because one CDS has several target subsequence pairs spaced this length, because of redundancy in the selected CDSs, or because signals of this length were generated by more than one pair of target subsequences. Spike 104 at a slightly longer length represents a relative length with only one hit. This fragment is generated from a unique sequence and provides a unique indication of its presence in a cDNA mixture, that is, this is a good sequence.

6.2. Restriction Endonucleases

Tables 1–4 list all palindromic 4-mer and 6-mer potential RE recognition sequences. RE enzymes recognizing each site, where known, are also listed, along with an exemplary commercial supplier. Over 85% of possible sequences spanning a wide range of occurrence probabilities have a known RE recognizing and cleaving the sequence.

The frequency of these sequences was determined, as in example 6.1, in 12,000 human first continuous coding domain sequences selected from the October 1994 GenBank database. The tables are sorted in order of increasing recognition occurrence probability. The bar in the recognition sequence indicates the site in the recognition sequence where the RE cuts.

The following vendor abbreviations are used: New England Biolabs (Beverly, Mass.) ("NEB"), Stratagene (La Jolla, Calif.), Boehringer Mannheim (Indianapolis, Ind.) ("BM"), and Gibco BRL division of Life Technologies (Gaithersburg, Md.) ("BRL").

TABLE 1

THE 4-MER RESTRICTION SITES

| Recognition Sequence | CDS Frequency | RE | Overhang | Vendor |
|---|---|---|---|---|
| C\|GCG | 0.36 | SelI | 2 | |
| C\|TAG | 0.44 | MaeI | 2 | NEB |
| T\|TAA | 0.45 | MseI | 2 | NEB |
| TATA | 0.45 | none | | |
| GCG\|C | 0.50 | HhaI | 2 | NEB |
| ATAT | 0.50 | none | | |
| A\|CGT | 0.52 | MaeII | 2 | BM |
| T\|CGA | 0.53 | TaqI | 2 | NEB |
| \|AATT | 0.53 | Tsp509I | 4 | NEB |
| C\|CGG | 0.61 | MspI | 2 | NEB |
| G\|TAC | 0.64 | Csp6I | 2 | NEB |
| \|GATC | 0.67 | Sau3AI | 4 | NEB |
| CATG\| | 0.68 | NlaIII | 4 | NEB |
| TG\|CA | 0.78 | CviRI | 0 | |
| AG\|CT | 0.78 | AluI | 0 | NEB |
| GG\|CC | 0.79 | HaeIII | 0 | NEB |

TABLE 2

THE FIRST 20 6-MER RESTRICTION SITES

| Sequence | CDS Frequency | RE | Overhang | Vendor |
|---|---|---|---|---|
| TCG\|CGA | 0.01 | NruI | 0 | NEB |
| TAC\|GTA | 0.02 | SnaBI | 0 | NEB |
| C\|GTACG | 0.02 | BsiWI | 4 | NEB |
| CGAT\|CG | 0.02 | PvuI | 2 | NEB |
| A\|CGCGT | 0.03 | MluI | 4 | NEB |
| A\|CTAGT | 0.03 | SpeI | 4 | NEB |
| G\|TCGAC | 0.04 | SalI | 4 | NEB |
| AA\|CGTT | 0.04 | Psp1406I | 2 | NEB |
| A\|CCGGT | 0.04 | AgeI | 4 | NEB |
| G\|CTAGC | 0.04 | NheI | 4 | NEB |
| TATATA | 0.04 | none | | |

TABLE 2-continued

THE FIRST 20 6-MER RESTRICTION SITES

| Sequence | CDS Frequency | RE | Overhang | Vendor |
|---|---|---|---|---|
| GTT\|AAC | 0.05 | HpaI | 0 | NEB |
| TAGCTA | 0.05 | none | | |
| TAATTA | 0.05 | none | | |
| GTA\|TAC | 0.05 | Bstl107I | 0 | NEB |
| CTATAG | 0.05 | none | | |
| CGCGCG | 0.05 | none | | |
| C\|CTAGG | 0.06 | AvrII | 4 | NEB |
| TT\|CGAA | 0.06 | SfaI | 2 | BM |
| AT\|CGAT | 0.06 | ClaI | 2 | NEB |

TABLE 3

THE MIDDLE 20 6-MER RESTRICTION SITES

| Sequence | CDS Frequency | RE | Overhang | Vendor |
|---|---|---|---|---|
| C\|TTAAG | 0.06 | AflII | 4 | NEB |
| T\|CTAGA | 0.06 | Xbal | 4 | NEB |
| ATATAT | 0.07 | none | | |
| AT\|TAAT | 0.07 | vspI | 2 | BRL |
| G\|CGCGC | 0.08 | BssHII | 4 | NEB |
| C\|AATTG | 0.08 | MunI | 4 | NEB |
| GACGT\|C | 0.08 | AatII | 4 | NEB |
| TTATAA | 0.09 | none | | |
| TGC\|GCA | 0.10 | FspI | 0 | NEB |
| C\|TCGAG | 0.01 | XhoI | 4 | NEB |
| GAT\|ATC | 0.01 | EcoRV | 0 | NEB |
| CA\|TATG | 0.10 | NdeI | 2 | NEB |
| ATGCA\|T | 0.01 | NsiI | 4 | NEB |
| AGC\|GCT | 0.11 | Eco47III | 0 | NEB |
| AAT\|ATT | 0.11 | SspI | 0 | NEB |
| T\|CCGGA | 0.11 | AccIII | 4 | Stratagene |
| TTT\|AAA | 0.12 | DraI | 0 | NEB |
| A\|CATGT | 0.12 | BspLVII | 4 | |
| CAC\|GTG | 0.12 | Eco72I | 0 | Stratagene |
| CCGC\|GG | 0.12 | SacII | 2 | NEB |

TABLE 4

THE LAST 24 6-MER RESTRICTION SITES

| Sequence | CDS Frequency | RE | Overhang | Vendor |
|---|---|---|---|---|
| GCATG\|C | 0.13 | SphI | 4 | NEB |
| TTGCAA | 0.13 | none | | |
| A\|AGCTT | 0.13 | HindIII | 4 | NEB |
| G\|TGCAC | 0.13 | ApaLI | 4 | NEB |
| AAATTT | 0.14 | none | | |
| AGT\|ACT | 0.15 | ScaI | 0 | NEB |
| G\|AATTC | 0.15 | EcoRI | 4 | NEB |
| GGTAC\|C | 0.15 | KpnI | 4 | NEB |
| T\|GTACA | 0.15 | Bspl407I | 4 | NEB |
| C\|GGCCG | 0.15 | EagI | 4 | NEB |
| G\|CCGGC | 0.16 | NgoMI | 4 | NEB |
| GGC\|GCC | 0.16 | NarI | 0 | NEB |
| T\|GATCA | 0.16 | BclI | 4 | NEB |
| T\|CATGA | 0.17 | BspHI | 4 | NEB |
| C\|CCGGG | 0.19 | SmaI | 4 | NEB |
| G\|GATCC | 0.19 | BamHI | 4 | NEB |
| A\|GATCT | 0.20 | BglII | 4 | NEB |
| AGG\|CCT | 0.22 | StuI | 0 | NEB |
| GGGCC\|C | 0.24 | ApaI | 4 | NEB |
| C\|CATGG | 0.24 | NcoI | 4 | NEB |
| GAGCT\|C | 0.25 | SacI | 4 | NEB |
| TGG\|CCA | 0.33 | MscI | 0 | NEB |
| CAG\|CTG | 0.42 | PvuII | 0 | NEB |
| CTGCA\|G | 0.43 | PstI | 4 | NEB |

6.3. RNA Extraction and cDNA Synthesis

RNA Preparation

RNA extraction is done using Triazol reagent from Life Technologies (Gaithersburg, Md.) following the protocol of Chomszynski et. al., 1987, Annal. Biochem. 162:156–59 and Chomszynski et. al., 1993, Biotechniques, 15:532–34, 536–37. Total RNA is first extracted from tissues, treated with Rnase-free Dnase I from Pharmacia Biotech (Uppsala, Sweden) to remove contaminating genomic DNA, followed by messenger RNA purification using oligo (dT) magnetic beads from Dynal Corporation (Oslo, Norway), and then used for cDNA synthesis.

If desired, total cellular RNA can be separated into sub-pools prior to cDNA synthesis. For example, a sup-pool of endoplasmic reticulum associated RNA is enriched for RNA producing proteins having an extra-cellular or receptor function.

Tissue Homogenization and Total RNA Extraction

A voxel is used to describe the specific-piece of tissue to be analyzed. Most frequently it will refer to grid punches corresponding to pathologically characterized tissue sections.

1. It is important that tissue voxels be quick frozen in liquid nitrogen immediately after dissection, and stored at −70° C. until processed.
2. The weight of the frozen tissue voxel is measured and recorded.
3. Tissue voxels are pulverized and ground in liquid nitrogen, either with a porcelain mortar and pestle, or by stainless steel pulverizers, or alternative means. This tissue is ground to a fine powder and is kept on liquid nitrogen.
4. The tissue powder is transferred to a tube containing Triazol reagent (Life Technologies, Gaithersburg, Md.) with 1 ml of reagent per 100 mg of tissue and is dispersed in the Triazol using a Polytron homogenizer from Brinkman Instruments (Westbury, N.Y.). For small tissue voxels less than 100 mg, a minimum of 1 ml of Triazol reagent should be used for efficient homogenization.
5. Add 0.1 volumes BCP (1-bromo-3-chloropropane) (Molecular Research, Cincinnati, Ohio) and mix by vortexing for 30 seconds. Let the mixture stand at room temperature for 15 minutes.
6. Centrifuge for 15 minutes at 4° C. at 12,000× G.
7. Remove the aqueous phase to a fresh tube and add 0.5 volumes isopropanol per original amount of Triazol reagent used and mix by vortexing for 30 seconds. Let the mixture stand at room temperature for 10 minutes.
8. Centrifuge at room temperature for 10 minutes at 12,000× G.
9. Wash with 70% ethanol and centrifuge at room temperature for 5 minutes at 12,000× G.
10. Remove the supernatant and let the centrifuge tube stand to dry in an inverted position.
11. Resuspend the RNA pellet in water (1 µl per mg of original tissue weight) and heat to 55° C. until completely dissolved.

DNase Treatment

1. Add 0.2 volume of 5× reverse transcriptase buffer (Life Technologies, Gaithersburg, Md.), 0.1 volumes of 0.1 M DTT, and 5 units RNAguard per 100 mg starting tissue from Pharmacia Biotech (Uppsala, Sweden).
2. Add 1 unit RNase-free DNase I, Pharmacia Biotech, per 100 mg starting tissue. Incubate at 37° C. for 20 minutes.

The following additional steps are optional,

Opt 1. Repeat RNA extraction by adding 10 volumes of Triazol reagent.

Opt 2. Repeat steps 5 through 11.

3. Quantify the total RNA (from the RNA concentration obtained by measuring $OD_{260}$ of a 100 fold dilution). Store at −20° C.

Isolation of Poly $A^+$ Messenger RNA

Poly-adenylated mRNA is isolated from total RNA preparations using magnetic bead mediated oligo-dT detection. Kits that can be used include Dynabeads mRNA Direct Kit from Dynal (Oslo, Norway) or MPG Direct mRNA Purification Kit from CPG (Lincoln Park, N.J.). Protocols are used as directed by the manufacturer.

Less preferably, the following procedure can be used. The Dynal oligo(dT) magnetic beads have a capacity of 1 ug poly($A^+$) per 100 ug of beads (1 mg/ml concentration), assuming 2% of the total RNA has poly($A^+$) tails.

1. Add 5 volumes of Lysis/Binding buffer (Dynal) and sufficient beads to bind the estimated poly($A^+$) RNA.
2. Incubate at 65° C. for 2 minutes, then at room temperature for 5 minutes.
3. Wash beads with 1 ml Washing buffer/LiDS (Dynal)
4. Wash beads with 1 ml Washing buffer (Dynal) 2 times.
5. Elute poly($A^+$). RNA with 1 µl water/ug beads 2 times.

For both methods, the poly-adenylated RNA is harvested in a small volume of water, quantified as above, and stored at −20° C. Typical yields of poly-adenylated RNA range from 1% to 4% of the input total RNA.

cDNA Synthesis cDNA is synthesized using the Superscript™ Choice system from Life Technologies, Inc. (Gaithersburg, Md.). If greater than 1 µg of polyadenylated RNA is used, the manufacturer's protocols are followed, using 50 ng of random hexamer primers per microgram of polyadenylated RNA.

If tissue voxels are the source for the RNA, the polyadenylated RNA is not quantified, and the entire yield of polyadenylated RNA is concentrated by precipitation with ethanol. The polyadenylated RNA is resuspended in 10 µl of water, and 5 to 10 µl are used for cDNA synthesis. The manufacturer's protocols are followed for RNA amounts of less than 1 µg, and 100 ng of random hexamers are used as primers. The resulting volume of the cDNA solution is 150 µl, but the amount is not quantified. QEA test reactions are run using 1 µl or 0.1 µl of cDNA solution in order to determine the appropriate amount of cDNA to use for subsequence QEA reactions.

Alternative primers for first strand synthesis known in the art can also be used for first strand synthesis. Such primers include oligo(dT) primers, phasing primers, etc.

6.4. QEA Preferred RE Method

This protocol is designed to keep the number of individual manipulations down, and thereby raise the reproducibility of the QEA procedure. In a preferred method no buffer changes, precipitations or organic (phenol/chloroform) extractions are used, all of which lower the overall efficiency of the process and reduce its utility for general use and more specifically for its use in automated or robotic procedures.

6.4.1. cDNA Preparation

Terminal phosphate removal from cDNA is illustrated with the use of Barents sea shrimp alkaline phosphatase ("SAP") (U.S. Biochemical Corp.) and 2.5 µg of cDNA. Substantially less (<10 ng) or more (>20 µg) of cDNA can be prepared at a time with proportionally adjusted amounts of enzymes. Volumes are maintained to preserve ease of handling. The quantities necessary are consistent with using the method to analyze small tissue samples from normal or diseased specimens.

1. Mix the following reagents
   2.5 µl 200 mM Tris-HCL
   23 µl cDNA
   2 µl 2 units/pl Shrimp alkaline phosphatase
   The final resulting cDNA concentration is 100 ng/µl.
2. Incubate at 37° C. for 1 hour
3. Incubate at 80° C. 15 minutes to inactivate the SAP.

6.4.2. Preferred RE/Ligase and Amplification Reactions

Once the cDNA has been prepared, including terminal phosphate removal, it is separated into a number of batches of from 10 ng to 200 ng each, equal to the desired number of individual samples that need to be analyzed and the extent of the analysis. For example, if six RE/ligase reactions and six analyses are needed to generate all necessary signals, six batches are made. Shown by example are 50 ng fractions.

RE/ligase reactions are performed as digestions by, preferably, a pair of REs; alternatively, one or three or more REs can be used provided the four base pair overhangs generated by each RE differ and can each be ligated to a uniquely adapter and a sufficiently resolved length distribution results. The amount of RE enzyme specified is sufficient for complete digestion while minimizing any other exo- or endo-nuclease activity that may be present in the enzyme.

Adapters are chosen that are unique to each RE in a reaction. Thus, one uses a linker complementary to each unique RE sticky overhang and a primer which uniquely hybridized with that linker. The primer/linker combination is an adapter, which will preferably be uniquely and distinguishably labeled.

Adapter Annealing

Pairs of 12-mer linkers and 24-mer primers are pre-annealed to form adapters before they are used in the QEA reactions, as follows:

1. Add to water linker and primer in a 2:1 concentration ratio (12-mer:24-mer) with the primer at a total concentration of 5 pM per µl.
2. Incubate at 50° C. for 10 minutes.
3. Cool slowly to room temperature and store at −20° C.

Restriction-Digestion/Ligation Reaction

Reactions are prepared for use in a 96 well thermal cycler. Add per reaction:

1. 1 U of appropriate REs (New England Biolabs, Beverly, Mass.) (preferred RE pair listing in § 6.9)
2. 1 µl of appropriate annealed adapter
3. 1 µl of Ligase/ATP (0.2 µl T4 DNA ligase [1 U/µl]/0.8 µl 10 mM ATP from Life Technologies (Gaithersburg, Md.))
4. 0.5 µl 50 mM $MgCl_2$
5. 10 ng of subject prepared cDNA
6. 1 µl 10× NEB2 buffer from New England Biolabs (Beverly, Mass.)
7. Water to bring total volume to 10 µl Then perform the RE/ligation reaction by following the thermal profile in FIG. 16A using a PTC-100 Thermal Cycler from M J Research (Watertown, Mass.).

Amplification Reaction

Prepare the PCR reaction mix by combining:

1. 10 µl 5× E-Mg (300 mM Tris-Hcl pH 9.0, 75 mM (NH$_4$)$_2$SO$_4$, no Mg ions))
2. 100 pm of appropriate fluorescently labeled 24-mer primers
3. 1 µl 10 mM dNTP mix (Life Technologies, Gaithersburg, Md.)
4. 2.5 U of 50:1 Taq polymerase (Life Technologies, Gaithersburg, Md.) : Pfu polymerase (Stratagene, La Jolla, Calif.)
5. Water to bring volume to 40 µl per PCR reaction Then perform the following steps:

1. Add 40 µl of the PCR reaction mix to each RE/ligation reaction
2. Perform the PCR temperature profile of FIG. 16B using a PTC-100 thermal cycler (M J Research, Watertown, Mass.)

6.4.3. Preferred Automated Re/Ligase Reactions

The reactions of the preceding section can be automated according to the following protocol which requires intermediate reagent additions or by a protocol note requiring such additions.

Single Tube Protocol With Reagent Additions

Reactions are preformed in a standard 96 well thermal cycler format using a Beckman Biomek 2000 robot (Beckman, Sunnyvale, Calif.). Typically 4 cDNA samples are analyzed in duplicate with 12 different RE pairs, for a total of 96 reactions. All steps are performed by the robot, including solution mixing, from user provided stock reagents, and temperature profile control.

Pre-annealed adapters are prepared as in the preceding section.

Restriction-Digestion/Ligation Reaction

Mix per reaction:

1. 1 U of appropriate RE (New England Biolabs, Beverly, Mass.)
2. 1 µl of appropriate annealed adapter (10 pmoles)
3. 0.1 µl T4 DNA ligase [1 U/µl] (Life Technologies (Gaithersburg, Md.)
4. 1 µl ATP (Life Technologies, Gaithersburg, Md.)
5. 5 ng of subject prepared cDNA
6. 1.5 µl 10× NEB2 buffer from New England Biolabs (Beverly, Mass.)
7. 0.5 µl of 50 mg MgCl$_2$
8. Water to bring total volume to 10 µl and transfer to thermal cycler The robot requires 23 minutes total time to set up the reactions. Then it performs the RE/ligation reaction by following the temperature profile of FIG. 16C using a PTC-100 Thermal Cycler equipped with a mechanized lid from MJ Research (Watertown, Mass.).

Amplification Reaction

Prepare the PCR reaction mix by combining:

1. 10 µl 5× E-Mg (300 mM Tris-HCl pH 9.0, 75 mM (NH$_4$)$_2$SO$_4$)
2. 100 pm of appropriate fluorescently labeled 24-mer primer
3. 1 µl 10 mM dNTP mix (Life Technologies, Gaithersburg, Md.)
4. 2.5 U of 50:1 Taq polymerase (Life Technologies, Gaithersburg, Md.):Pfu polymerase (Stratagene, La Jolla, Calif.)
5. Water to being volume to 35 µl per PCR reaction Preheat the PCR mix to 72° C. and transfer 35 µl of the PCR mix to each digestion/ligation reaction and mix. The robot requires 6 minutes for the transfer and mixing.

Figure 16A:
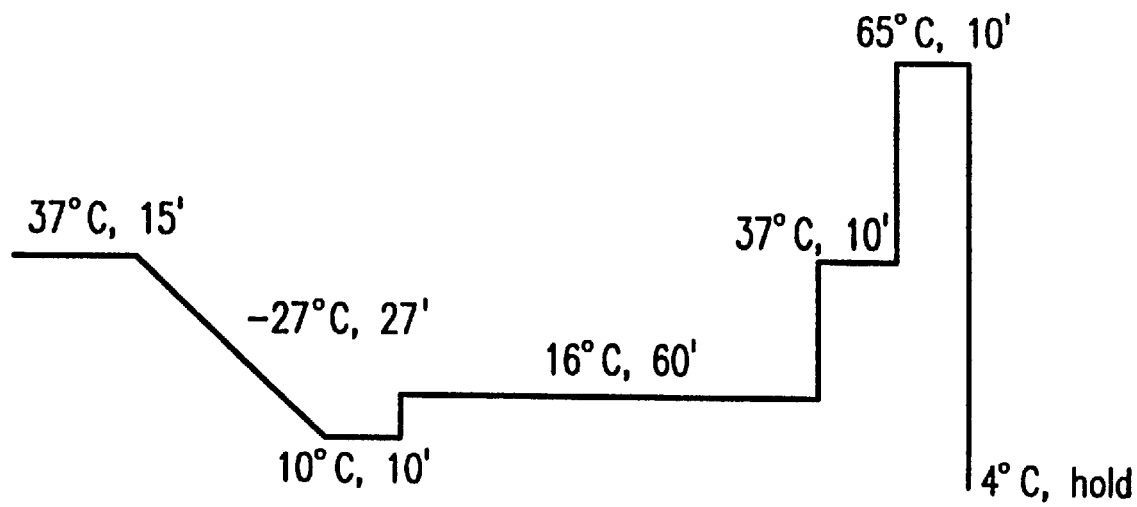
Figure 16B:
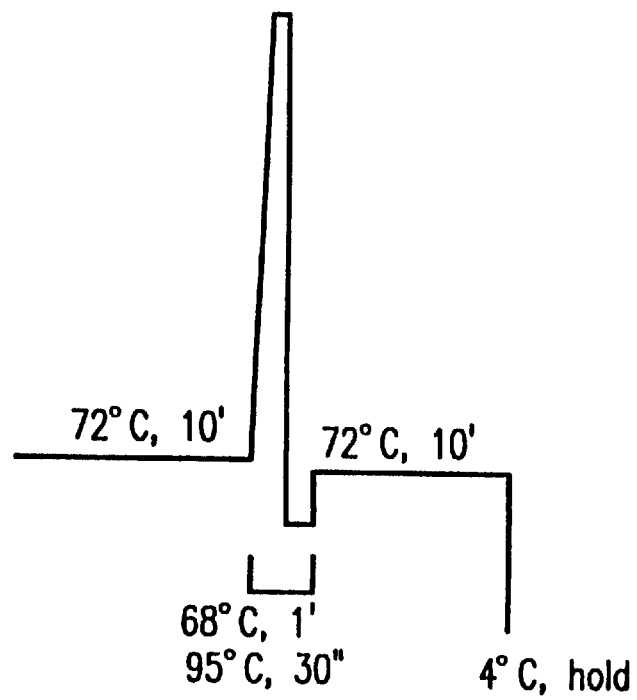
Figure 16C:
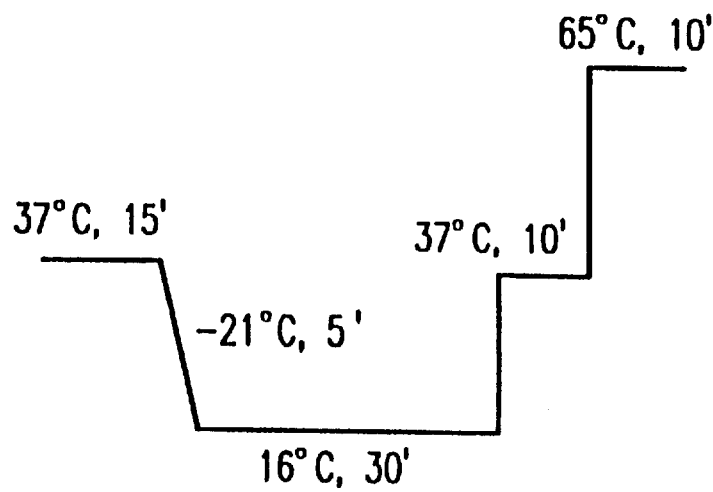
Figure 16D:
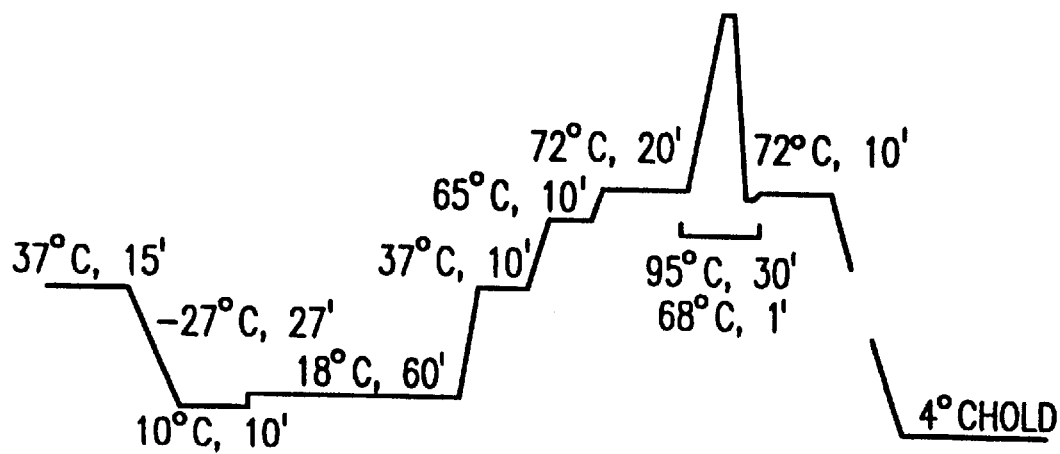

Then the robot performs the PCR amplification reaction by following the temperature profile of FIG. 16B using a PTC-100 thermal cycler equipped with a mechanized lid (M J Research, Watertown, Mass.).

The total elapsed time for the digestion/ligation and PCR amplification reactions is 179 minutes. No user intervention is required after initial experimental design and reagent positioning.

Single Tube Protocol Without Reagent Additions

First, add the PCR reaction mix by combining in the reaction tube:

1. 10 µl 5× E-Mg (300 mM Tris-HCl pH 9.0, 75 mM (NH$_4$)$_2$SO$_4$)
2. 100 pm of appropriate fluorescently labeled 24-mer primer
3. 2 µL 10 mM dNTP mix (Life Technologies, Gaithersburg, Md.)
4. 2.5 U of 50:1 Tag polymerase (Life Technologies, Gaithersburg, Md.):Pfu polymerase (Stratagene, La Jolla, Calif.)
5. Water to bring volume to 40 µl per PCR reaction Second, add a bead of wax melting approximately at 72° C. (Ampliwax, Perkin-Elmer, Norwalk, Conn.). Melt the wax at 75° C. for 5 minutes, and let the wax solidify at 25° C. for 10 minutes with the lid open.

Third, add the RE/ligase reaction mix by combining in the reaction tube:

1. 0.1 µl of the REs (New England Biolabs, Beverly, Mass.)
2. 1 µl of appropriate annealed adapter (2:1 of 12:24 mer at 50 pmoles/ml)
3. 0.2 µl T4 DNA ligase [1 U/µl] (Life Technologies (Gaithersburg, Md.)
4. 1 µl of 0.1 M ATP (Life Technologies, Gaithersburg, Md.)
5. 1 µl of subject prepared cDNA (0.1–10 ng)
6. 0.1 µl 10× NEB 2 buffer from New England Biolabs (Beverly, Mass.)
7. 0.5 µl of 50 mM MgCl$_2$
8. Water to bring total volume to 10 µl and transfer to thermal cycler Then perform the RE/ligation and PCR reactions by following the thermal profile in FIG. 16D using, for example, a PTC-100 Thermal Cycler from M J Research (Watertown, Mass.).

6.4.4. Alternative RE/Ligase and Amplification Reactions

Once the cDNA has been prepared it is separated into a number of batches of from 20 ng to 200 ng each equal to the desired number of individual samples that need to be analyzed and the extent of the analysis. For example, if six RE/ligase reactions and six analyses are needed to generate all necessary signals, six batches are made. Shown by example are 50 ng fractions.

RE/ligase reactions are performed as digestions by, preferably, a pair of REs; alternatively, one or three or more REs can be used provided the four base pair overhangs generated by each RE differ and can each be ligated to a uniquely adapter and a sufficiently resolved length distribution results. The amount of RE enzyme specified is sufficient for complete digestion while minimizing any other exo- or endo-nuclease activity that may be present in the enzyme.

RE Digestion

Digest (with 50 ng of cDNA)

1. Mix the following reagents 0.5 µl prepared cDNA (100 ng/µl) mixture
10 µl New England Biolabs Buffer No. 2
3 Units RE enzyme 2. Incubate for 2 hours at 37° C. Larger size digests with higher concentrations of cDNA can be used and fractions of the digest saved for additional sets of experiments.

Adapter Ligation

Since it is important to remove unwanted ligation products, such as concatamers of fragments from different cDNAs resulting from hybridization of RE sticky ends, the restriction enzyme is left active during ligation. This leads to a continuing cutting of unwanted concatamers and end ligation of the desired end adapters.

The majority of restriction enzymes are active at the 16° C. ligation temperature. Ligation profiles-consisting of optimum ligation conditions interspersed with optimum is digestion conditions can also be used to increase efficiency of this process. An exemplary profile comprises periodically cycling between 37° C. and 10° C. and 16° C. at a ramp of 1° C./min.

One linker complementary to each 5 minutes overhang generated by each RE is required. 100 pico moles ("pm") is a sufficient molar excess for the protocol described. For each linker a complementary uniquely labeled primer is added for ligation to the cut ends of cDNAs. 100 pm is a sufficient molar excess for the protocol described. If the amounts of RE cDNA is changed the linker and primer amounts should be proportionately changed.

Ligation Reaction (per 10 µl and 50 ng cDNA)

1. Mix the following reagents

| Component | Volume |
| --- | --- |
| RE digested cDNA mixture | 10 µl |
| 100 pM/µl each primer | 1 µl |
| 100 pM/µl each linker | 1 µl |

2. Thermally cycle from 50° C. to 10° C. (−1° C./minute) then back to 16° C.
3. Add 2 µl 10 mM ATP with 0.2 µl T4 DNA ligase (Premix 0.1 µl ligase 1 U/µl per 1 µl ATP) (E. Coli ligase is a less preferred alternative ligase.)
4. Incubate 12 hours at 16° C. This step can be shortened to less than 2 hours with proportionately higher ligase concentration. Alternately the thermal cycling protocol described can be used here.
5. Incubate 2 hours 37° C.
6. Incubate 20 minutes at 65° C. to heat inactivate the ligase (last step should be RE cutting).
7. Hold at 4° C.

Amplification of Fragments With Ligated Adapters

This step amplifies the fragments that have been cut twice and ligated with adapters unique for each RE cut end. It is designed for a very high amplification specificity. Multiple amplifications are performed, with an increasing number of amplification cycles. Use the minimum number of cycles to get the desired signal. Amplifications above 20 cycles are not generally reliably quantitative.

Mix the following to form the ligation mix:

| Component | Volume |
| --- | --- |
| RE/Ligase cDNA mixture | 5 µl |
| 10X PCR Buffer | 5 µl |
| 25 mM MgCl$_2$ | 3 µl |
| 10 mM dNTPs | 1 µl |
| 100 pM/µl each primer | 1 µl |

Mix the following to form 150 µl PCR-Premix

| | |
| --- | --- |
| 30 µl | Buffer E (ligation mix will contribute 0.3 mM MgCl) |
| 1 µl | (300 pmoles/µl Rbuni24 Flour) 24 mer primer strand (50 pmoles/µl NBuni24 Tamra) |
| 0.6 µl | Taq polymerase (per 150 µl) |
| 3 µl | dNTP (10 mM) |
| 106 µl | H$_2$O |

Amplification of fragments is more specific if the small linker dissociates from the ligated primer-cDNA complex prior to amplification. The following is an exemplary method for amplification of the results of six RE/ligase reactions.

1. Place three strips of six PCR tubes, marked 10, 15, and 20 cycles, into three rows on ice as shown.

| | | | | | | |
| --- | --- | --- | --- | --- | --- | --- |
| 20 cycles | 1 | 2 | 3 | 4 | 5 | 6 Add 140 µl PCR-premix |
| 15 cycles | 1 | 2 | 3 | 4 | 5 | 6 |
| 10 cycles | 1 | 2 | 3 | 4 | 5 | 6 Add 10 µl ligation mix |

2. Place 10 µl ligation mix in each tube in 10 cycle row
3. Place 140 µl PCR premix in each tube in 20 cycle row
4. Place into cycler and incubate for 5 minutes at 72° C. This melts linker which was not covalently ligated to the second strand of a cDNA fragment and allows the PCR premix to come to temperature.
5. Move the 140 µl PCR premix into the tubes in the 10 cycle row containing the 10 µl ligation mix, then place 50 µl of result into corresponding tubes each in other rows.
6. Incubate for 5 minutes at 72° C. This finishes incompletely double stranded cDNA ends into complete dsDNA, the top primer being used as template for second strand completion.

The amplification cycle is designed to raise specificity and reproducibility of the reaction. High temperature and long melting times are used to reduce bias of amplification due to high G+C content. Long extension times are used to reduce bias in favor of smaller fragments.

7. Thermally cycle 95° C. for 1 minute followed by 68° C. for 3 minutes. Long denaturing times reduce PCR bias due to melting rates of fragments, and long extension time reduces PCR bias on fragment sizes.
8. Incubate at 72° C. for 10 minutes at end of reaction.

6.4.5. Optional Post-Amplification Steps

Several optional steps can improve the signal from the detected bands. First, single strands produced as a result of linear amplification from singly cut fragments can be removed by the use of single strand specific exonuclease. Exo I is the preferred nuclease.

1. Incubate 2 units of nuclease with the product of each PCR reaction for 60 minutes at 37° C.

Second, the amplified products can be concentrated prior to detection either by ethanol precipitation or column separation with a hydroxyapatite column.

Several labeling methods are usable, including fluorescent labeling as has been described, silver staining, radiolabelled end primers, and intercalating dyes. Fluorescent end labeling is preferred for high throughput analysis with silver staining preferred if the individual bands are to be removed from the gel for further processing, such as sequencing.

Finally, fourth, use of two primers allows direct sequencing of separated strands by standard techniques. Also separated strands can be directly cloned into vectors for use in RNA assays such as in situ analysis. In that case, it is more preferred to use primers containing T7 or other polymerase signals.

6.5. QEA by the PCR Embodiment

This is an alternative QEA implementation based on PCR amplification of fragments between target subsequences recognized by PCR primers or sets of PCR primers. It is designed for the preferred primers described with reference to FIG. 5. If other primers are used, such as simple sets of degenerate oligonucleotides, step 5, the first low stringency PCR cycle, is omitted.

First strand cDNA synthesis is carried out according to Example 6.3. PCR amplification with defined sets of primers is performed according to the following protocol.

1. Rnase treat the 1st strand mix with 1 µl of RNase Cocktail from Ambion, Inc. (Austin, Tex.) at 37° C. for 30 minutes.
2. Phenol/CHCl₃ extract the mixture 2 times, and purify it on a Centricon 100, Milipore Corporation (Bedford, Mass.) using water as the filtrate.
3. Bring the end volume of the cDNA to 50 µl (starting with 10 ng RNA/µl).
4. Set up the following PCR Reaction:

| Component | Volume |
| --- | --- |
| cDNA (~10 ng/µl) | 1 µl |
| 10X PCR Buffer | 2.5 µl |
| 25 mM MgCl₂ | 1.5 µl |
| 10 mM dNTPs | 0.5 µl |
| 20 pM/µl primer1 | 2.5 µl |
| 20 pM/µl primer2 | 2.5 µl |
| Taq Pol. (5 U/µl) | 0.2 µl |
| water | 14.3 µl |

5. One low stringency cycle with the profile:
   40° C. for 3 minutes (annealing)
   72° C. for 1 minute (extension)
6. Cycle using the following profile:
   95° C. for 1 minute
   15–30 times:
      95° C. for 30 seconds
      50° C. for 1 minute
      72° C. for 1 minute
   72° C. for 5 minutes
7. 4° C. hold.
8. Samples are precipitated, resuspended in denaturing loading buffer, and analyzed.

6.6. Example of Simulated Annealing

From the October 1994 GenBank database containing human coding sequences, 12,000 of the first continuous coding domain sequences ("CDS") were selected. This selection resulted in a set of sequences biased towards short sequences, having an average length of 1000 compared to the average gene length of 1800–2000. Frequency tables were then created that listed the occurrence frequency of each nucleotide subsequence of lengths 4, 5, 6, 7, and 8. Test target subsequences were initially selected whose probability of occurrence was near to 50%. This was feasible for the 4-mers, as they bind relatively frequently, but as the occurrence probability decreases with length, for longer sequences, the occurrence probability was often substantially less than 50%. These initially selected target subsequences were then optimized, using the simulated annealing CC experimental design methods, to pick the best 16 subsequences.

Tables 5, 6 and 7 present the results for target subsequences of lengths 4, 5 and 6, respectively. Table 8 presents the results for optimizing target subsequences of length 4 through 6 together. Simulated annealing generally produced an approximately 20% improvement over target subsequence selection guided only by the occurrence and independence probability criteria. This level of optimization is likely to improve with larger and less redundant databases that represent longer genes. Longer sequences bind too infrequently in this database to make useful hash codes.

TABLE 5

| AN OPTIMIZED SET OF 4-MER SEQUENCES | | | |
| --- | --- | --- | --- |
| CGTC | GTTA | ACTA | CTAG |
| TTTT | TGTA | AATC | GTTG |
| TACC | TTGT | TTCG | GATA |
| CGGT | CTCG | AACG | GGTA |

The target subsequences in Table 5 were chosen from all possible 256 4-mers. There are 2.41 CDSs per hash code on average. There was 692 CDSs (out of 12000) which are not complementary to any of these PNAs.

TABLE 6

| AN OPTIMIZED SET OF 5-MER SEQUENCES | | | |
| --- | --- | --- | --- |
| AGGCA | ACTGT | GTCTC | TGTGC |
| CAACT | GCCCC | ACTAC | GTGAC |
| GCACC | GTCTG | GCCTC | CAGGT |
| AGGGG | GGAAC | GCTCC | GCTCT |

The target subsequences in Table 6 were chosen from the 300 most frequently occurring 5-mers. There are 2.33 CDSs per hash code on average. There was 829 CDSs (out of 12000) which are not complementary to any of these PNAs.

TABLE 7

| AN OPTIMIZED SET OF 6-MER SEQUENCES | | | |
| --- | --- | --- | --- |
| TCCTCA | CCAGGC | AGCAGC | CTCCTG |
| AGCTGG | CTCTGG | CCAGGG | CAGAGA |
| GCCTGG | ACTGGA | CACCAT | GCTGTG |
| ACTGTG | TCTGTG | CCAAGG | CCTGGA |

The target subsequences in Table 7 were chosen from the 200 most frequently occurring 6-mers. There was 2.63 CDSs per hash code on average. There are 1530 CDSs (out of 12000) which are not complementary to any of these PNAs.

TABLE 8

AN OPTIMIZED SET OF 4-, 5-, AND 6-MER SEQUENCES

| | | | |
|---|---|---|---|
| CTCG | TTCG | GATA | TTTT |
| CTAG | GGTA | ACTGT | ACTAC |
| CAACT | GTCTG | AGGCA | GCACC |
| TGTGC | GGAAC | AGGGG | CTCCTG |

The target subsequences in Table 8 were chosen from sets in Tables 1–3. There was 2.22 CDSs per hash code on average. There are 715 CDSs (out of 12000) which are not complementary to any of these PNAs.

The bias of the selected CDSs toward short sequences, on the average less than the length of a typical gene, partially explains the 5–10% of CDSs that were not complementary to any selected target subsequence. Longer sequences would be expected to have more hits as they have more variability. Also more target subsequences can be chosen to improve coverage. The 2.2 to 2.6 CDSs per individual hash code is partially explained by replication in the selected database. No attempt was make to insure each CDS is unique among the other selected CDSs.

6.7. QEA Results

This subsection present results from QEA experiments directed primarily to the query and tissue modes.

6.7.1. Query Mode QEA Results

The pattern of gene expression differs from tissue to tissue, and is modulated both during normal development and during the progression of many diseases, including cancer. Query mode QEA experiments were used to investigate differences in gene expression between normal, hyperplastic, and adenocarcinomic glandular tissues. We had at our disposal voxels containing all three types of tissue, preserved in such a way that the adjacent tissue sections were available for later in situ hybridization. The following experiments were carried out with normal, hyperplastic, and adenocarcinomic tissue, respectively, as a particular gland.

RNA Extraction and cDNA Synthesis

Isolation of total RNA and poly(A)$^+$ RNA from homogenized glandular tissue voxels was performed substantially as described in § 6.3. cDNA was prepared substantially as described in §§ 6.3 and 6.4.1.

Quantitative Expression Analysis

QEA reactions were performed by the preferred RE embodiment substantially as described in § 6.4.2. This included the following steps.

Adapter Annealing

Pairs of 12-base and 24-base primers were pre-annealed at a ratio of 2:1 (12 mer:24 mer) at a concentration of 5 picomoles 24 mer per microliter in 1×NEB2 buffer. The oligonucleotide mixture was heated to 50° C. for 10 minutes, and allowed to cool slowly to room temperature. For this experiment, 10 picomoles of JC3 and 5 picomoles of JC24, and 10 picomoles of RC6 and 5 picomoles of RC24 were separately pre-annealed. The sequences of JC3, JC24, RC6, and RC24 are listed in Table 10 of § 6.9, infra.

Restriction-Digestion/Ligation Reaction

Reactions were prepared in for use in a 8-well thermal cycler format. Glandular cDNA isolated from 10 separate voxels of tissue was cut with HindIII and NgoMI, and pre-annealed linkers were ligated onto the 4 base 5' overhangs that these enzymes generated. Added per each QEA reaction were:

1 Unit of HindIII (New England Biolabs, Beverly Mass.)
1 Unit of NgoMI (New England Biolabs, Beverly Mass.)
1 µl of pre-annealed JC3/JC24
1 µl of pre-annealed RC6/RC24
1 µl Ligase/ATP (0.2 µl T4 DNA Ligase [1 Unit/µl]/0.8 µl
10 mM ATP—Life Technologies, Gaithersburg Md.)
0.5 µl 50 mM MgCL$_2$
10 nanograms of glandular cDNA
1 µl 10× NEB2 Buffer (New England Biolabs, Beverly Mass.)
Total volume of 10 µl with H$_2$O The temperature profile of FIG. 16A was performed using a PTC-100 Thermal Cycler (M J Research, Watertown Mass.).

Amplification Reaction

The products of the RE/ligation reaction were then amplified using RC24 and JC24 primers. The PCR reaction mix included:

10 µl 5× E-Mg (300 mM Tris-HCL pH 9.0, 75 mM (NH$_4$)$_2$SO$_1$)
100 picomoles RC24
100 picomoles JC24
1 µl 10 mM dNTP mix (Life Technologies, Gaithersburg Md.)
2.5 Units 50:1 Taq polymerase (Life Technologies, Gaithersburg Md.): Pfu polymerase (Stratagene, La Jolla Calif.) mix The total volume was brought to 40 µl per reaction with H$_2$O.

40 µl preheated PCR reaction mix was added to each restriction-digestion/ligation reaction.

The temperature profile of FIG. 16B was performed using a PTC-100 Thermal Cycler (M J Research, Watertown Mass.).

QEA Analysis

The reaction products were separated on a 5% acrylamide sequencing gel, and detected by silver staining. Lane-to-lane comparisons were made both by visual inspection of the gel, and by comparing computer enhanced images obtained from scanning the gel using standard computer scanner equipment. One particular band of length X bp was differentially expressed, being prominent in some samples but absent in others. This band was picked from the gel, PCR reamplified, and sequenced.

QEA analysis was performed substantially as described in § 5.4.1 using the CDS database constructed as described in § 6.1. Four possible sequences in that database were found to be possible contributors to a fragment of Y bp (note that Y bp=X−46 bp, where PCR primers add 46 bp to the fragment length), sequences A, B, C, and D. Analysis of the sequencing of the picked band confirmed that this DNA fragment was produced by sequence C, which is presently entered in GenBank. This result confirms the correct functioning of the integrated experimental and analysis methods.

Further, analysis of sequence C predicted that a second double-digest, using REs BspHI and BstYI, would yield a second, non-overlapping restriction fragment at Z bp in length (plus the 46 bp of ligated primers). A second QEA reaction was performed using these glandular cDNAs. The previously described experimental condition were used, with the exception of substituting BspHI, BstYI, RA5/RA24 and JC9/JC24 for HindIII, NgoMI, JC3/JC24 and RC6/RC24 during the RE/ligation reaction and of substituting RA24 and JC24 during amplification reaction. Analysis of the results of this second QEA experiment on silver-stained acrylamide gels, as above, revealed the presence of a band of the predicted size, Z+46 bp, that was also differentially expressed in the same tissue samples as the X bp fragment. This results confirms the correct functioning of the mock digest prediction methods coupled with subsequence actual experimental digest.

Additional hybrid primers were designed to facilitate direct sequencing of the QEA products and the direct generation of RNA probes for the in situ hybridization to the original tissue sample. The M13-21 primer or the M13 reverse primer (in italics) were fused to the first 23 nucleotides of JC24 and RC24 (in bold), respectively, to allow direct sequencing of the double-digested QEA products.

M13-21J+JA24: 5' GGC GCG CCT GTA AAA CGA CGG CCA GTA CCG ACG TCG ACT ATC CAT GAA G 3' (SEQ ID NO:56)

M13revR+RA24: 5' AAA ACT GCA GGA AAC AGC TAT GAC CAG CAC TCT CCA GCC TCT CAC CGA 3' (SEQ ID NO:57)

In order to enable direct generation of anti-sense RNA probes for in situ hybridization, the phage T7 promotor (in italics) was fused to the first 23 nucleotides of JA24/JC24 and RA24/RC24 (in bold).

T7+JA24: 5' ACT TCG AAA TTA ATA CGA CTC ACT ATA GGG ACC GAC GTC GAC TAT CCA TGA AG 3' (SEQ ID NO:58)

T7+RA24: 5' ACT TCG AAA TTA ATA CGA CTC ACT ATA GGG AGC ACT CTC CAG CCT CTC ACC GA 3' (SEQ ID NO:59)

6.7.2. Tissue Mode QEA Results

Isolation of Human Placental Lactogen using QEA

Lactogen is one of the most highly expressed genes in the human placenta and has a known sequence. The sequence of lactogen was retrieved from GenBank and mock digestion reactions were performed, substantially as described in § 5.4.1, with a wide selection of possible RE pairs. These mock digestions showed that digesting placental cDNA with the restriction enzymes BssHIII and XbaI yields a lactogen fragment of 166 bp in length.

RNA Extraction and cDNA Synthesis

Isolation of total RNA and poly(A)$^4$ RNA from homogenized human placenta tissue was performed substantially as described in § 6.3. cDNA was prepared substantially as described in §§ 6.3 and 6.4.1.

Quantitative Expression Analysis

QEA reactions were performed by the preferred RE embodiment substantially as described in § 6.4.2. This included the following steps.

Adapter Annealing

Pairs of 12-base and 24-base primers were pre-annealed at a ratio of 2:1 (12 mer:24 mer) at a concentration of 5 picomoles 24 mer per microliter in 1× NEB2 buffer. The oligonucleotide mixture was heated to 50° C. for 10 minutes, and allowed to cool slowly to room temperature. For this experiment, 10 picomoles of RC8 and 5 picomoles of RC24, and 10 picomoles of JC7 and 5 picomoles of JC24 were separately pre-annealed. The sequences of RC8, RC24, JC7, and JC24 are set forth in Table 10 of § 6.9, infra.

Restriction-Digestion/Ligation Reaction

Reactions were prepared for use in a 8-well thermal cycler format. Placental cDNA was cut with BssHIII and XbaI, and pre-annealed adapters ligated onto the 4 base 5' overhangs that these enzymes generated. Added per reaction were:

1 Unit of BssHII (New England Biolabs, Beverly Mass.)

1 Unit of XbaI (New England Biolabs, Beverly Mass.)

1 μl of pre-annealed RC8/RC24

1 μl of pre-annealed JC7/JC24

1 μl Ligase/ATP (0.2 μl T4 DNA Ligase [1 Unit/μl]/0.8 μl 10 mM ATP—Life Technologies, Gaithersburg Md.)

0.5 μl 50 MM MgCl$_2$ 10 nanograms of placental cDNA

1 μl 10× NEB2 Buffer (New England Biolabs, Beverly Mass.) Total volume was brought to 10 μl with H$_2$O.

The temperature profile of FIG. 16A was performed using a PTC-100 Thermal Cycler (M J Research, Watertown Mass.).

Amplification Reaction

The products of the RE/ligation reaction were then amplified using RC24 and JC24 primers (see Table 10, infra). The PCR reaction mix included:

10 μl X 5× E-Mg (300 mM Tris-HCl pH 9.0, 75 mM (NH$_4$)$_2$SO$_4$)

100 picomoles RC24

100 picomoles JC24

1 μl 10 mM dNTP mix (Life Technologies, Gaithersburg Md.)

2.5 Units 50:1 Taq polymerase (Life Technologies, Gaithersburg Md.): Pfu polymerase (Stratagene, La Jolla Calif.) mix.

The total volume was brought to to 40 μl per reaction with H$_2$O.

40 μl preheated PCR reaction mix was added to each restriction-digestion/ligation reaction.

The temperature profile of FIG. 16B was performed using a PTC-100 Thermal Cycler (M J Research, Watertown Mass.).

QEA Analysis

The reaction products were separated on a 5% acrylamide sequencing gel and detected by silver staining. A prominent band of size 212 bp was seen. This was predicted to correspond to the 166 bp lactogen BssHII-XbaI fragment, with JC24 ligated to the BssHII site, and RC24 ligated to the XbaI site. To prove that this band did indeed correspond to lactogen, the 212 bp band was excised from the gel, re-amplified using JC24 and RC24, and the fragment was sequenced. Analysis of these sequencing results proved that the fragment was from lactogen. Moreover, the lactogen sequence ended at the expected 4 base remnant of the restriction site, immediately followed by either JC24 (at the BssHII end) or RC24 (at the XbaI end).

This result confirmed the experimental design methods of § 5.4.2 applied to selection of a QEA experiment to identify certain sequences of interest, in this case the human placental lactogen sequence, in a tissue cDNA sample. These design methods resulted in the selection of an experiment which successfully identified the gene intended.

Further QEA experiments were done according to the protocols of this section on human placental derived cDNA with differing enzyme combinations. One unit of each enzyme of the enzyme combinations listed in the first column of Table 9 were used in the restriction-digestion/ligation reaction protocol. Primers and linbers for each RE were chosen according to Table 10, with one appropriate "J" series linker and primer and one appropriate "R" series linker and primer used in each reaction. The reaction products were separated by electrophoresis on a 5% acrylamide gel and the bands detected by silver staining. Fragments from certain bands, listed in the second column of Table 9, were removed from the gel and sequenced. Sequencing identified the subsequences on the ends of the fragments and the lengths of the fragments. Each subsequence was characteristic of one of the REs used, confirming correct action of the ligation and amplification protocols. These end subsequences for each fragment are listed in the third column of Table 9, where a "1" indicates digestion by RE "Enz1" and a "2" indicated digestion by RE "Enz2". Multiple fragments with the same length but differing end subsequences are placed in separate rows in Table 9.

Mock digest reactions, as described in § 5.4.1, were performed using the CDS database selected according to § 6.1. These mock digestion reactions searched this CDS database for sequences having recognition sites for the REs and such that the recognition sites are spaced apart in order to produce the fragments of the determined lengths listed. This search identified the database accession numbers listed in the fourth column of Table 9. The gene responsible for each accession number was determined from a GenBank lookup and is listed in the fifth column of Table 9. Table 9 is further grouped into one row for each such gene. Multiple accession numbers associated with one gene reflect the redundancy present in current CDS DNA sequence databases.

For all fragments recovered from the gel, the sequence for the fragment corresponded to one of the genes identified by the mock digestion reaction as causing that fragment. This particular gene is indicated by displaying the gene name in underscore in the fifth column of Table 9. That the gene determined by sequencing the separated fragment matched the prediction of the database search confirms the efficacy of the experimental protocols and the computer implemented experimental analysis and ambiguity resolution methods of §§ 5.4.1 and 5.4.2 for tissue mode QEA. In fact, the mock digestion reactions provide a simple way of identifying possible ambiguities in DNA sequence databases.

TABLE 9

PLACENTA GENE CALLS

| RE Combinations (Enz1 & Enz2) | Fragment Length | End Subseq. | Database Acc. Numbers | Gene Causing Fragment |
|---|---|---|---|---|
| BglII & BspE1 | 97 | 1,2 | D23660, L20868, X73974 | Ribosomal Protein L4 |
| | 97 | 1,1 | X07767 | cAMP-Dependent Protein Kinase |
| | 97 | 1,2 | J03278, M21616 | PDGF Receptor |
| | 97 | 2,2 | M74096 | Long Chain Acyl-CoA Dehydrogenase |
| BamH1 & BspE1 | 112 | 1,2 | L26914, M93718, M95296 | Nitric Oxide Synthase |
| | 112 | 1,2 | L22453, M90054, X73460 | Ribosomal Protein L3a |
| BglII & BspE1 | 115 | 1,2 | MX20496 X05256 | Cathepsin L |
| BglII & NgoM1 | 137 | 1,2 | L18967 | TRP2 Dopachrome Tautomerase |
| | 137 | 2,2 | X55740 | 5'-Nucleotidase |
| | 137 | 1,2 | L10386 | Tranglutaminase E3 |
| | 137 | 1,2 | S69231 | Tyrosinease-Related Protein 2 |
| | 137 | 1,2 | X56998, X56999 | Ubiquitin |
| EcoR1 & Bcl1 | 139 | 1,2 | U14967 | Ribosomal Protein L21 |
| Bcl1 & NgoM1 | 144 | 1,2 | J02984 | Ribosomal Protein S15 |
| | 144 | 2,2 | L12700 | Engrailed-2 |
| | 144 | 1,2 | U04683, X80391 | Olfactory Receptor OR17-40 |
| BamH1 & BspE1 | 144 | 1,2 | X97234 | Ribosomal Protein L11 |
| | 144 | 1,2 | X14362 | C3B/C4B Receptor |
| EcoR1 & HindIII | 146 | 1,2 | M13932 | Ribosomal Protein S17 |
| BssHII & Xba1 | 166 | 1,2 | J00118, V00573 | Lactogen |
| Bcl1 & NgoM1 | 168 | 1,2 | S56985, X63527 | Ribosomal Protein L19 |
| BamH1 & BspE1 | 173 | 1,1 | S59493, U10323 | Nuclear Factor NF45 |
| BamH1 & BspE1 | 173 | 1,2 | M20882, M23575, M31125, M33666, M34420, M37399, M69245, M93061 | Pregnancy Sp. Glycoprotein beta 1 |
| BglII & NgoM1 | 192 | 1,2 | D29992, L27624 | Tissue Factor Pathway Inhibitor 2 |
| | 192 | 1,1 | D26350 | Inositol Triphosphatase Receptor |
| | 192 | 1,1 | L27711, L25876 | Protein Phosphatase CIP2/KAP1 |
| BglII & Age1 | 215 | 1,2 | M11353, M11354 | Histone H3.3 |

6.8. Colony Calling

Colony calling comprises the principal steps of cDNA library filter construction, PNA hybridization, and detection of hybridization. Determination of the sequence in a sample is done by the prior described computer implemented experimental analysis methods. Alternatively, cDNA library filters may be obtained from commercial sources in certain cases.

cDNA Library Filter Construction

This protocol comprises three steps: first, robotic picking of colonies into microtiter plates, second, PCR amplification of inserts, and third, spotting of amplified cDNA inserts onto filters.

1. Colony Picking
   a) Libraries are plated out at a density of 1,000–10,000 colonies per 100 mm Petri dish and are picked using a robot into 384 well microtiter plates containing 50 μl of TB medium with the appropriate antibiotic. There are several commercially available robots to do this task.

The preferable robot is from the Washington University Human Genome Sequencing Center (St. Louis, Mo.).

b) The picked colonies are grown for 8 hours at 37° C., and are frozen for archiving.

2. PCR amplification—PCR primer pairs designed for insert amplification are dispensed with a standard 25 μl PCR mix into 96 well microtiter plates. A 96 prong transfer tool picks and transfers samples to provide amplification templates from the 384 well colony into the 96 well PCR mixes. A standard 25 cycle amplification protocol generates 100–500 ng of insert DNA.

3. Spotting on filers—The PCR products are pooled back into a 384 well format microtiter plates identical to the colony plates above. Spotting onto filters is a service performed by Research Genetics (Huntsville, Ala.).

PNA Hybridization and Detection

PNAs are commercially available from Perseptive Biosystems (Bedford, Mass.). The protocol below uses 8 dyes on 16 different degenerate sets of PNA 8-mers containing as common subsequences the optimized 6-mer subsequences from Table 7. Thereby, complete classification and determination of expressed genes in a human tissue can be done with only 4 hybridizations generating a code of length 32. Actual conditions for stringency may vary depending on the PNA set used.

1. Hybridization—A pool of 8 PNAs are used, labeled with 8 different fluorochromes made up at a concentration of 0.1 μg/ml in 10 mM Phosphate buffer, pH 7.0, 1× Denhardt's solution (20 mg/ml Ficoll 400, polyvinylpyrollidone, and BSA). The arrayed filters are hybridized for 16 hrs at 25° C., and washed 3 times in the above buffer without PNAs at a temperature which maximizes signal/noise.

2. Visualization—A fluorescent detection system, such as used for DNA analysis, can be used to distinguish the dyes, and thus the PNAs, present at each filter hybridization position. PNA presence or absence defines a code for each hybridization position on the filter.

6.9. Preferred QEA Adapters and REs Pairs

Table 10 lists preferred primer-linker pairs that may be used as adapters for the preferred RE embodiment of QEA. The primers listed cover all possible double-digest RE combinations involving approximately 56 available RE having a 5' 4 bp overhang. There are 40 such REs available from New England Biolabs. For each QEA double digest, one primer and one linker from the "R" series and one primer and one linker from the "J" series are used together. This choice satisfies all adapter constraints previously described. Two pairs from the same series are not compatible during amplification.

TABLE 10

SAMPLE ADAPTERS

| Series | Adapter: Primer (longer strand) Linker (shorter strand) | RE |
|---|---|---|
| RA24 | 5' AGC ACT CTC CAG CCT CTC ACC GAA 3' (SEQ ID NO:1) | |
| RA1 | 3' AG TGG CTT TTAA (SEQ ID NO:2) | Tsp509I Mfel EcoRI |
| RA5 | 3' AG TGG CTT GTAC (SEQ ID NO:3) | NcoI BspHI |
| RA6 | 3' AG TGG CTT GGCC (SEQ ID NO:4) | XmaI NgoMI BspEI |

TABLE 10-continued

SAMPLE ADAPTERS

| Series | Adapter: Primer (longer strand) Linker (shorter strand) | RE |
|---|---|---|
| RA7 | 3' AG TGG CTT GCGC (SEQ ID NO:5) | BssHII AscI |
| RA8 | 3' AG TGG CTT GATC (SEQ ID NO:6) | AvrII NheI XbaI |
| RA9 | 3' AG TGG CTT CTAG (SEQ ID NO:7) | DpnII BamHI BclI |
| RA10 | 3' AG TGG CTT CGCG (SEQ ID NO:8) | KasI |
| RA11 | 3' AG TGG CTT CCGG (SEQ ID NO:9) | EagI Bsp120I NotI EaeI |
| RA12 | 3' AG TGG CTT CATG (SEQ ID NO:10) | BsiWI Acc65I BsrGI |
| RA14 | 3' AG TGG CTT AGCT (SEQ ID NO:11) | XhoI SalI |
| RA15 | 3' AG TGG CTT ACGT (SEQ ID NO:12) | ApaLI |
| RA16 | 3' AG TGG CTT AATT (SEQ ID NO:13) | AflII |
| RA17 | 3' AG TGG CTT AGCA (SEQ ID NO:14) | BssSI |
| RC24 | 5' AGC ACT CTC CAG CCT CTC ACC GAC 3' (SEQ ID NO:15) | |
| RC1 | 3' AG TCG CTG TTAA (SEQ ID NO:16) | Tsp509I EcoRI ApoI |
| RC3 | 3' AG TCG CTG TCGA (SEQ ID NO:17) | HindIII |
| RC5 | 3' AG TCG CTG GTAC (SEQ ID NO:18) | BspHI |
| RC6 | 3' AG TCG CTG GGCC (SEQ ID NO:19) | AgeI NgoMI BspEI SgrAI BsrFI BsaWI |
| RC7 | 3' AG TCG CTG GCGC (SEQ ID NO:20) | MluI BssHII AscI |
| RC8 | 3' AG TCG CTG GATC (SEQ ID NO:21) | SpeI NheI XbaI |
| RC9 | 3' AG TCG CTG CTAG (SEQ ID NO:22) | DpnII BglII BamHI BclI BstYI |
| RC10 | 3' AG TCG CTG CGCG (SEQ ID NO:23) | KasI |
| RC11 | 3' AG TCG CTG CCGG (SEQ ID NO:24) | Bsp120I NotI |
| RC12 | 3' AG TCG CTG CATG (SEQ ID NO:25) | Acc56I BsrGI |
| RC14 | 3' AG TCG CTG AGCT (SEQ ID NO:26) | SalI |
| RC15 | 3' AG TCG CTG ACGT (SEQ ID NO:27) | Ppu10I ApaLI |
| JA24 | 5' ACC GAC GTC GAC TAT CCA TGA AGA 3' (SEQ ID NO:28) | |
| JA1 | 3' GT ACT TCT TTAA (SEQ ID NO:29) | Tsp509I Mfel EcoRI |
| JA5 | 3' GT ACT TCT GTAC (SEQ ID NO:30) | NcoI BspHI |
| JA6 | 3' GT ACT TCT GGCC (SEQ ID NO:31) | XmaI NgoMI BspEI |
| JA7 | 3' GT ACT TCT GCGC (SEQ ID NO:32) | BssHII AscI |

TABLE 10-continued

SAMPLE ADAPTERS

| Series | Adapter: Primer (longer strand) Linker (shorter strand) | RE |
|---|---|---|
| JA8 | 3' GT ACT TCT GATC (SEQ ID NO:33) | AvrII NheI XbaI |
| JA9 | 3' GT ACT TCT CTAG (SEQ ID NO:34) | DpnII BamHI BclI |
| JA10 | 3' GT ACT TCT CGCG (SEQ ID NO:35) | KasI |
| JA11 | 3' GT ACT TCT CCGG (SEQ ID NO:36) | EagI Bsp120I NotI EaeI |
| JA12 | 3' GT ACT TCT CATG (SEQ ID NO:37) | BsiWI Acc65I BsrGI |
| JA14 | 3' GT ACT TCT AGCT (SEQ ID NO:38) | XhoI SalI |
| JA15 | 3' GT ACT TCT ACGT (SEQ ID NO:39) | ApaLI |
| JA16 | 3' GT ACT TCT AATT (SEQ ID NO:40) | AflII |
| JA17 | 3' GT ACT TCT AGCA (SEQ ID NO:41) | BssSI |
| JC24 | 5' ACC GAC GTC GAC TAT CCA TGA AGC 3' (SEQ ID NO:42) | |
| JC1 | 3' GT ACT TCG TTAA (SEQ ID NO:43) | Tsp509I EcoRI ApoI |
| JC3 | 3' GT ACT TCG TCGA (SEQ ID NO:44) | HindIII |
| JC5 | 3' GT ACT TCG GTAC (SEQ ID NO:45) | BspHI |
| JC6 | 3' GT ACT TCG GGCC (SEQ ID NO:46) | AgeI NgoMI BspEI SgrAI BsrFI BsaWI |
| JC7 | 3' GT ACT TCG GCGC (SEQ ID NO:47) | MluI BssHII AscI |
| JC8 | 3' GT ACT TCG GTAC (SEQ ID NO:48) | SpeI NheI XbaI |
| JC9 | 3' GT ACT TCG CTAG (SEQ ID NO:49) | DpnII BglII BamHI BclI BstYI |
| JC10 | 3' GT ACT TCG CGCG (SEQ ID NO:50) | KasI |
| JC11 | 3' GT ACT TCG CCGG (SEQ ID NO:51) | Bsp120I NotI |
| JC12 | 3' GT ACT TCG CATG (SEQ ID NO:52) | Acc56I BsrGI |
| JC14 | 3' GT ACT TCG AGCT (SEQ ID NO:53) | SalI |
| JC15 | 3' GT ACT TCG ACGT (SEQ ID NO:54) | Ppul0I ApaLI |

Tables 11 and 12 list the RE combinations that have been tested in QEA experiments on human placental and glandular cDNAs samples. The preferred double digests are those that give more than approximately 50 bands in the range of 100 to 700 bp. Table 11 lists the preferred RE combinations for human cDNA analyses.

TABLE 11

PREFERRED RE COMBINATIONS FOR HUMAN cDNA ANALYSIS

| | | |
|---|---|---|
| Acc56I & HindIII | Acc65I & NgoMI | BamHI & EcoRI |
| BglII & HindIII | BglII & NgoMI | BsiWI & BspHI |
| BspHI & BstYI | BspHI & NgoMI | BsrGI & EcoRI |
| EagI & EcoRI | EagI & HindIII | EagI & NcoI |
| HindIII & NgoMI | NgoMI & NheI | NgoMI & SpeI |
| BglII & BspHI | Bsp120I & NcoI | BssHII & NgoMI |
| EcoRI & HindIII | NgoMI & XbaI | |

Tables 12 lists other RE combinations tested and that can be used for human cDNA analyses.

TABLE 12

OTHER RE COMBINATIONS FOR HUMAN cDNA ANALYSIS

| | | |
|---|---|---|
| AvrII & NgoMI | BamHI & Bsp120I | BamHI & BspHI |
| BamHI & NcoI | BclI & BspHI | BclI & NcoI |
| BglII & BspEI | BglII & EcoRI | BglII & NcoI |
| BssHII & BsrGI | BstYI & NcoI | BamHI & HindIII |
| BglII & Bsp120I | BspHI & HindIII | |

Tables 13 and 14 list the RE combinations that have been tested in QEA experiments on mouse cDNA samples. The preferred double digests are those that give more than approximately 50 bands in the range of 100 to 700 bp. Table 13 lists the preferred RE combinations for mouse cDNA analyses.

TABLE 13

PREFERRED RE COMBINATIONS FOR MOUSE cDNA ANALYSIS

| | | |
|---|---|---|
| Acc56I & HindIII | Acc65I & NgoMI | AscI & HindIII |
| AvrII & NgoMI | BamHI & BspHI | BamHI & HindIII |
| BamHI & NcoI | BclI & NcoI | BglII & BspHI |
| BglII & HindIII | BglII & NcoI | BglII & NgoMI |
| Bsp120I & NcoI | Acc65I & BspHI | BspHI & Bsp120I |
| BspHI & BsrGI | BspHI & EagI | BspHI & NgoMI |
| BspHI & NotI | BssHII & HindIII | BstYI & HindIII |
| HindIII & NcoI | HindIII & NgoMI | NcoI & NotI |
| NgoMI & NheI | NgoMI & SpeI | NgoMI & XbaI |
| BclI & HindIII | | |

Table 14 lists other RE combinations tested and that can be used for mouse cDNA analyses.

TABLE 14

OTHER RE COMBINATIONS FOR MOUSE cDNA ANALYSIS

| | | |
|---|---|---|
| Acc65I & NcoI | BclI & BspHI | BsiWI & BspHI |
| BsiWI & NcoI | BspHI & HindIII | BsrGI & NcoI |
| BssHII & NgoMI | BstYI & BspHI | EagI & NcoI |
| HindIII & MluI | | |

Table 15 lists the data obtained from various RE combinations using mouse cDNA samples. The number of bands was observed from silver stained acrylamide separation gels.

TABLE 15

MOUSE cDNA RE DIGESTION RESULTS

| RE Combination | Number of Bands |
| --- | --- |
| Acc65I & HindIII | 200 |
| Acc65I & NgoMI | 150 |
| AscI & HindIII | 100 |
| AvrII & NgoMI | 50 |
| BamHI & BspHI | 200 |
| BamHI & HindIII | 150 |
| BamHI & NcoI | 150 |
| BclI & BspHI | 5 |
| BclI & HindIII | 150 |
| BclI & NcoI | 50 |
| BglII & BspHI | 50 |
| BglII & HindIII | 150 |
| BglII & NcoI | 50 |
| BglII & NgoMI | 50 |
| Bsp120I & NcoI | 50 |
| BspHI & Acc65I | 150 |
| BspHI & Bsp120I | 50 |
| BspHI & BsrGI | 200 |
| BspHI & EagI | 150 |
| BspHI & HindIII | 0 |
| BspHI & NgoMI | 150 |
| BspHI & NotI | 150 |
| BsrGI & NcoI | 10 |
| BssHII & HindIII | 100 |
| BssHII & NgoMI | 20 |
| BstYI & BspHI | 20 |
| BstYI & HindIII | 200 |
| EagI & NcoI | 10 |
| HindIII & MluI | 25 |
| HindIII & NcoI | 50 |
| HindIII & NgoMI | 150 |
| NcoI & NotI | 200 |
| NgoMI & NheI | 50 |
| NgoMI & SpeI | 200 |
| NgoMI & XbaI | 50 |
| TOTAL # BANDS | 3490 |

31 available REs that recognize a 6 bp recognition sequence and generate a 4 bp 5' overhang are: Acc65I, AflII, AgeI, ApaLI, ApoI, AscI, AvrI, BamHI, BclI, BglII, BsiWI, Bspl20I, BspEI, BspHI, BsrGI, BssHII, BstYI, EagI, EcoR1, HindIII, MfeI, MluI, NcoI, NgoMI, NheI, NotI, Ppu10I, SalI, SpeI, XbaI, and XhoI.

All of these enzymes have been tested in QEA protocols with the specified buffer conditions with the exception of AflII. All were useable except for MfeI, Ppu10I, SalI, and XhoI. All the other 26 enzymes have been tested and are usable in the RE implementation of QEA.

However certain pairs of these enzymes are less informative due to the fact that they produce identical overhangs, and thus their recognition sequences cannot be distinguished by QEA adapters. These pairs are Acc65I and (BsiWI or BsrGI); AgeI and (BspEI or NcoMI); ApoI and EcoRI; AscI and (BssHII or MluI); AvrI and (NheI, SpeI, or XbaI); BamHI and (BclI, BglII, or BstYI); BclI and (BglII or BstYI); BglII and BstYI; BsiWI and BsrGI; Bspl20I and EagI; BspEI and NcoMI; BspHI and NcoI; BssHII and MluI; NheI and (SpeI or XbaI); and SpeI and XbaI.

Thus 301 RE pairs have been tested and are useable in the RE embodiments of QEA.

6.10. Fluorescent Labels

Fluorochromes labels that can be used in the methods of the present invention include the classic fluorochromes as well as more specialized fluorochromes. The classic fluorochromes include bimane, ethidium, europium (III) citrate, fluorescein, La Jolla blue, methylcoumarin, nitrobenzofuran, pyrene butyrate, rhodamine, terbium chelate, and tetramethylrhodamine. More specialized fluorochromes are listed in Table 16 along with their suppliers.

TABLE 16

FLORESCENT LABELS

| Fluorochrome | Vendor | Absorption Maximum | Emission Maximum |
| --- | --- | --- | --- |
| Bodipy 493/503 | Molecular Probes | 493 | 503 |
| Cy2 | BDS | 489 | 505 |
| Bodipy FL | Molecular Probes | 508 | 516 |
| FTC | Molecular Probes | 494 | 518 |
| FluorX | BDS | 494 | 520 |
| FAM | Perkin-Elmer | 495 | 535 |
| Carboxy-rhodamine | Molecular Probes | 519 | 543 |
| EITC | Molecular Probes | 522 | 543 |
| Bodipy 530/550 | Molecular Probes | 530 | 550 |
| JOE | Perkin-Elmer | 525 | 557 |
| HEX | Perkin-Elmer | 529 | 560 |
| Bodipy 542/563 | Molecular Probes | 542 | 563 |
| Cy3 | BDS | 552 | 565 |
| TRITC | Molecular Probes | 547 | 572 |
| LRB | Molecular Probes | 556 | 576 |
| Bodipy LMR | Molecular Probes | 545 | 577 |
| Tamra | Perkin-Elmer | 552 | 580 |
| Bodipy 576/589 | Molecular Probes | 576 | 589 |
| Bodipy 581/591 | Molecular Probes | 581 | 591 |
| Cy3.5 | BDS | 581 | 596 |
| XRITC | Molecular Probes | 570 | 596 |
| ROX | Perkin-Elmer | 550 | 610 |
| Texas Red | Molecular Probes | 589 | 615 |
| Bodipy TR (618?) | Molecular Probes | 596 | 625 |
| Cy5 | BDS | 650 | 667 |
| Cy5.5 | BDS | 678 | 703 |
| DdCy5 | Beckman | 680 | 710 |
| Cy7 | BDS | 443 | 767 |
| DbCy7 | Beckman | 790 | 820 |

The suppliers listed in Table 16 are Molecular Probes (Eugene, Ore.), Biological Detection Systems ("BDS") (Pittsburgh, Pa.) and Perkin-Elmer (Norwalk, Conn.).

Means of utilizing these fluorochromes by attaching them to particular nucleotide groups are described in Kricka et al., 1995, Molecular Probing, Blotting, and Sequencing, chap. 1, Academic Press, New York. Preferred methods of attachment are by an amino linker or phosophoramidite chemistry.

7. Specific Embodiments, Citation of References

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for identifying, classifying, or quantifying one or more proteins in a sample comprising a plurality of amino acids having different amino acid sequences, said method comprising:
  (a) probing said sample with one or more recognition means, each recognition means recognizing a different target amino acid subsequence or a different set of target amino acid subsequences;
  (b) generating one or more output signals from said sample probed by said recognition means, each output signal being produced from a protein in said sample by recognition of one or more target amino acid subsequences in said protein by said recognition means and comprising a representation of (i) the length between occurrences of target amino acid subsequences in said protein, and (ii) the identities of said target amino acid subsequences in said protein or the identities of said sets of target amino acid subsequences among which are included the target amino acid subsequences in said protein; and
  (c) searching an amino acid sequence database to determine sequences that are predicted to produce or the absence of any sequences that are predicted to produce said one or more output signals produced by said protein, said database comprising a plurality of known amino acid sequences of proteins that may be present in the sample, a sequence from said database being predicted to produce said one or more output signals when the sequence from said database has both (i) the same length between occurrences of target amino acid subsequences as is represented by said one or more output signals, and (ii) the same target amino acid subsequences as are represented by said one or more output signals, or target amino acid subsequences that are members of the same sets of target amino acid subsequences represented by said one or more output signals, whereby said one or more proteins in said sample are identified, classified, or quantified.

2. The method of claim 1 wherein each recognition means recognizes one target amino acid subsequence, and wherein a sequence from said database is predicted to produce a particular output signal when the sequence from said database has both the same length between occurrences of target amino acid subsequences as is represented by the output signal and the same target amino acid subsequences as represented by the particular output signal.

3. The method of claim 1 wherein each recognition means recognizes a set of target amino acid subsequences, and wherein a sequence from said database is predicted to produce a particular output signal when the sequence from said database has both the same length between occurrences of target amino acid subsequences as is represented by the particular output signal, and the target amino acid subsequences are members of the sets of target amino acid subsequences represented by the particular output signal.

4. The method of claim 1 further comprising dividing said sample of proteins into a plurality of portions and performing the steps of claim 1 individually on a plurality of said portions, wherein a different one or more recognition means are used with each portion.

5. The method of claim 1 wherein the quantitative abundances of proteins in said sample are determined from the quantitative levels of the output signals produced by said proteins.

6. The method of claim 5 wherein the protein is prepared from a plant, a single celled animal, a multicellular animal, a bacterium, a virus, a fungus, or a yeast.

7. The method of claim 5 wherein the recognition means are one or more protein cleaving agents whose recognition sites are said target amino acid subsequences, and wherein the step of probing further comprises cleaving the sample into fragments with said one or more protein cleaving agents.

8. The method of claim 7 further comprising:
  (a) identifying a fragment of a protein in the sample which generates said one or more output signals; and
  (b) recovering said fragment.

9. The method of claim 8 wherein the output signals generated by said recovered fragment are not predicted to be produced by a sequence in said amino acid sequence database.

10. The method of claim 7 wherein the step of generating further comprises separating protein fragments by length.

11. The method of claim 10 wherein the step of generating further comprises detecting said separated protein fragments.

12. The method of claim 11 wherein the abundance of a protein comprising a particular amino acid sequence in the sample is determined from the level of the one or more output signals produced by said protein that are predicted to be produced by said particular amino acid sequence.

13. The method of claim 11 wherein said representation of the length between occurrences of target amino acid subsequences is the length of fragments determined by said separating and detecting steps.

14. The method of claim 11 wherein said separating is carried out by use of liquid chromatography or mass spectrometry.

15. The method of claim 11 wherein said separating is carried out by use of electrophoresis.

16. The method of claim 15 wherein said electrophoresis is carried out in a gel arranged in a slab or arranged in a capillary using a denaturing or non-denaturing medium.

17. The method of claim 1 wherein a predetermined one or more amino acid sequences in said database are of interest, and wherein the target amino acid subsequences are such that said sequences of interest are predicted to produce at least one output signal that is not predicted to be produced by other amino acid sequences in said database.

18. The method of claim 17 wherein the amino acid sequences of interest are a majority of the sequences in said database.

19. The method of claim 1 wherein the target amino acid subsequences are such that amino acid sequences in said database comprise on average a sufficient number of occurrences of target amino acid subsequences in order to on average be predicted to produce an output signal that is not predicted to be produced by any other amino acid sequence in said database.

20. The method of claim 1 wherein the target amino acid subsequences are selected according to the further steps comprising:
    (a) predicting a pattern of signals that can be produced and the sequences predicted to produce each such signal by simulating the steps of probing and generating using sequences in said database of amino acid sequences;
    (b) ascertaining an amount of information in said determined pattern of signals, said amount being indicated by the numerical value of an information measure, said information measure being computed from said determined pattern of signals and the sequences predicted to generate each such signal in said pattern; and
    (c) choosing the target amino acid subsequences in order to predict a new pattern that maximizes said amount of information indicated by the information measure.

21. The method of claim 20 wherein said choosing step selects target subsequences which comprise the recognition sites of the one or more protein cleaving agents.

22. The method of claim 20 wherein said choosing step selects target amino acid subsequences which comprise recognition sites of one or more protein cleaving agents and one or more additional amino acids, said additional amino acids contiguous with said recognition sites.

23. The method of claim 20 wherein a predetermined one or more of the amino acid sequences present in said database of amino acid sequences are of interest, and the information measure is the number of said sequences of interest which are predicted to produce at least one output signal that is not predicted to be produced by any other amino acid sequence present in said database.

24. The method of claim 23 wherein said amino acid sequences of interest are a majority of the amino acid sequences present in said database.

25. The method of claim 20 wherein said choosing step is by a method comprising searching all combinations of target amino acid subsequences of length less than approximately 10.

26. The method of claim 1 wherein the step of searching comprises:
    (a) predicting a pattern of signals that can be produced and the sequences predicted to produce each such signal by simulating the steps of probing and generating using sequences in said database of amino acid sequences; and
    (b) determining the one or more amino acid sequences in said database that are predicted to produce said one or more output signals by finding in said pattern those signals that comprise a representation of (i) the same lengths between occurrences of target amino acid subsequences as is represented by the output signals, and (ii) the same target amino acid subsequences as are represented by the output signals, or target amino acid subsequences that are members of the same sets of target amino acid subsequences represented by the output signals.

27. The method of claim 26 wherein the step of predicting comprises:
    (a) searching for occurrences of said target amino acid subsequences or sets of target amino acid subsequences in amino acid sequences in said database of amino acid sequences;
    (b) determining the lengths between occurrences of said target amino acid subsequences or sets of target amino acid subsequences in the amino acid sequences of said database; and
    (c) storing in said pattern of signals predicted to be produced from the sequences of said database information representing that said amino acid sequences can produce output signals comprising a representation of the identities of said target amino acid subsequences and of said lengths between occurrences of said target amino acid subsequences.

28. A method for identifying or classifying a protein in a sample comprising a plurality of proteins having different amino acid sequences, said method comprising:
    (a) probing said protein with a plurality of recognition means, each recognition means recognizing a target amino acid subsequence or a set of target amino acid subsequences, in order to produce an output set of signals, each signal of said output set representing whether said target amino acid subsequence or one of said set of target amino acid subsequences is present in said protein; and
    (b) searching a amino acid sequence database, said database comprising a plurality of known amino acid sequences of proteins that may be present in the sample, for sequences predicted to produce said output set of signals, a sequence from said database being predicted to produce an output set of signals when the sequence from said database (i) comprises the same target amino acid subsequences represented as present, or comprises target amino acid subsequences that are members of the sets of target amino acid subsequences represented as present by the output set of signals, and (ii) does not comprise the target amino acid subsequences not represented as present or that are members of the sets of target amino acid subsequences not represented as present by the output set of signals, whereby the protein is identified or classified.

29. The method of claim 28 wherein the set of signals are represented by a hash code which is a binary number.

30. The method of claim 28 wherein the step of probing produces an output set of signals further representing the numbers of occurrences of said target amino acid subsequences or of members of said sets of target amino acid subsequences in said protein.

31. The method of claim 31 wherein an amino acid sequence from said database is predicted to produce said output set of signals when the sequence from said database (i) comprises the same target amino acid subsequences with the same number of occurrences in said sequence, or comprises target amino acid subsequences that are members of the same sets of target amino acid subsequences with the same number of occurrences in said sequence, represented as present by said output set of signals, and (ii) does not comprise the target amino acid subsequences not represented as present or that are members of the sets of target amino acid subsequences not represented as present by said output set of signals.

32. The method of claim 32 wherein the target amino acid subsequences are selected according to the further steps comprising:
   (a) predicting a pattern of sets of signals that can be produced and the sequences predicted to produce each set of signals in said pattern by simulating the step of probing using sequences in said database of amino acid sequences;
   (b) ascertaining an amount of information in said determined pattern of sets of signals, said amount being indicated by the value of an information measure, said information measure being computed from said determined pattern of sets of signals and the sequences predicted to produce each such set of signals in said pattern; and
   (c) choosing the target amino acid subsequences in order to predict a new pattern that maximizes said amount of information indicated by the information measure.

33. The method of claim 31 wherein the step of searching comprises:
   (a) predicting a pattern of sets of one or more signals that can be produced and the sequences capable of generating each set of signals in said pattern by simulating the step of probing using sequences in said database of amino acid sequences; and
   (b) determining one or more amino acid sequences that are predicted to produce said output set of signals by finding in said pattern those sets of signals that comprise a representation of the presence of the same target amino acid subsequences as are represented as present or target amino acid subsequences that are members of the sets of target amino acid subsequences represented as present by the output set of signals and (ii) does not represent as present the target amino acid subsequences not represented as present or that are members of the sets of target amino acid subsequences not represented as present by the output set of signals.

34. The method of claim 33 wherein the information measure is the number of sets of signals in the pattern which are predicted to be produced by one or more sequences in said database.

35. The method of claim 33 wherein the information measure is the number of sets of signals in the pattern which are predicted to be produced by only one sequence in said database.

36. The method of claim 33 wherein said choosing step is by a method comprising searching all combinations of target amino acid subsequences of length less than approximately 10.

37. The method of claim 33 or 32 wherein the step of predicting by simulating the probing further comprises:
   (a) searching for said target amino acid subsequences or sequences in said sets of target amino acid subsequences in amino acid sequences in said database of amino acid sequences; and
   (b) storing in said pattern of sets of signals predicted to be produced from said sequences in said database information representing that said amino acid sequences can produce sets of signals comprising a representation of the identities of said target amino acid subsequences or said sets of target amino acid subsequences found in said searching step.

38. The method of claim 37 where the step of searching is carried out by a string search.

39. The method of claim 37 wherein the step of searching comprises counting the number of occurrences of said target subsequences in each amino acid sequence.

* * * * *

UNITED STATES PATENT AND TRADEMARK OFFICE
CERTIFICATE OF CORRECTION

PATENT NO. : 6,231,812 B1
DATED : May 15, 2001
INVENTOR(S) : Rothberg et al.

It is certified that error appears in the above-identified patent and that said Letters Patent is hereby corrected as shown below:

<u>Column 131,</u>
Line 4, delete "claim 31" and insert -- claim 30 --
Line 17, delete "claim 32" and insert -- claim 31 --

Signed and Sealed this

Eleventh Day of March, 2003

JAMES E. ROGAN
*Director of the United States Patent and Trademark Office*

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

AGCACTCTCC AGCCTCTCAC CGAA                                          24

(2) INFORMATION FOR SEQ ID NO:2:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

AGTGGCTTTT AA                                                       12

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

AGTGGCTTGT AC                                                       12

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

AGTGGCTTGG CC                                                       12

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
AGTGGCTTGC GC                                                         12
```

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
AGTGGCTTGA TC                                                         12
```

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
AGTGGCTTCT AG                                                         12
```

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
AGTGGCTTCG CG                                                         12
```

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
AGTGGCTTCC GG                                                         12
```

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
AGTGGCTTCA TG                                                         12
```

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AGTGGCTTAG CT        12

(2) INFORMATION FOR SEQ ID NO:12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AGTGGCTTAC GT        12

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGTGGCTTAA TT        12

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

AGTGGCTTAG CA        12

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

AGCACTCTCC AGCCTCTCAC CGAC        24

(2) INFORMATION FOR SEQ ID NO:16:

(i) SEQUENCE CHARACTERISTICS:
        (A) LENGTH: 12 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

AGTCGCTGTT AA                                                              12

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

AGTCGCTGTC GA                                                              12

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AGTCGCTGGT AC                                                              12

(2) INFORMATION FOR SEQ ID NO:19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AGTCGCTGGG CC                                                              12

(2) INFORMATION FOR SEQ ID NO:20:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AGTCGCTGGC GC                                                              12

(2) INFORMATION FOR SEQ ID NO:21:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AGTCGCTGGA TC                                                              12

(2) INFORMATION FOR SEQ ID NO:22:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:22:

AGTCGCTGCT AG                                                              12

(2) INFORMATION FOR SEQ ID NO:23:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:23:

AGTCGCTGCG CG                                                              12

(2) INFORMATION FOR SEQ ID NO:24:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

AGTCGCTGCC GG                                                              12

(2) INFORMATION FOR SEQ ID NO:25:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

AGTCGCTGCA TG                                                              12

(2) INFORMATION FOR SEQ ID NO:26:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

```
AGTCGCTGAG CT                                                    12

(2) INFORMATION FOR SEQ ID NO:27:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AGTCGCTGAC GT                                                    12

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

ACCGACGTCG ACTATCCATG AAGA                                       24

(2) INFORMATION FOR SEQ ID NO:29:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GTACTTCTTT AA                                                    12

(2) INFORMATION FOR SEQ ID NO:30:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

GTACTTCTGT AC                                                    12

(2) INFORMATION FOR SEQ ID NO:31:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GTACTTCTGG CC                                                    12

(2) INFORMATION FOR SEQ ID NO:32:
```

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:32:

GTACTTCTGC GC                                                              12

(2) INFORMATION FOR SEQ ID NO:33:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:33:

GTACTTCTGA TC                                                              12

(2) INFORMATION FOR SEQ ID NO:34:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:34:

GTACTTCTCT AG                                                              12

(2) INFORMATION FOR SEQ ID NO:35:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:35:

GTACTTCTCG CG                                                              12

(2) INFORMATION FOR SEQ ID NO:36:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:36:

GTACTTCTCC GG                                                              12

(2) INFORMATION FOR SEQ ID NO:37:

(i) SEQUENCE CHARACTERISTICS:
           (A) LENGTH: 12 base pairs
           (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:37:

GTACTTCTCA TG                                                              12

(2) INFORMATION FOR SEQ ID NO:38:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

GTACTTCTAG CT                                                              12

(2) INFORMATION FOR SEQ ID NO:39:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

GTACTTCTAC GT                                                              12

(2) INFORMATION FOR SEQ ID NO:40:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

GTACTTCTAA TT                                                              12

(2) INFORMATION FOR SEQ ID NO:41:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

GTACTTCTAG CA                                                              12

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:42:

ACCGACGTCG ACTATCCATG AAGC                                                  24

(2) INFORMATION FOR SEQ ID NO:43:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

GTACTTCGTT AA                                                               12

(2) INFORMATION FOR SEQ ID NO:44:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

GTACTTCGTC GA                                                               12

(2) INFORMATION FOR SEQ ID NO:45:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

GTACTTCGGT AC                                                               12

(2) INFORMATION FOR SEQ ID NO:46:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

GTACTTCGGG CC                                                               12

(2) INFORMATION FOR SEQ ID NO:47:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GTACTTCGGC GC                                                               12

(2) INFORMATION FOR SEQ ID NO:48:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

GTACTTCGGT AC                                        12

(2) INFORMATION FOR SEQ ID NO:49:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

GTACTTCGCT AG                                        12

(2) INFORMATION FOR SEQ ID NO:50:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

GTACTTCGCG CG                                        12

(2) INFORMATION FOR SEQ ID NO:51:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

GTACTTCGCC GG                                        12

(2) INFORMATION FOR SEQ ID NO:52:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

GTACTTCGCA TG                                        12

(2) INFORMATION FOR SEQ ID NO:53:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:53:

GTACTTCGAG CT                                                     12

(2) INFORMATION FOR SEQ ID NO:54:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

GTACTTCGAC GT                                                     12

(2) INFORMATION FOR SEQ ID NO:55:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

AGCACTCTCC AGCCTCTCAC CGAGCATG                                    28

(2) INFORMATION FOR SEQ ID NO:56:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

GGCGCGCCTG TAAAACGACG GCCAGTACCG ACGTCGACTA TCCATGAAG             49

(2) INFORMATION FOR SEQ ID NO:57:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

AAAACTGCAG GAAACAGCTA TGACCAGCAC TCTCCAGCCT CTCACCGA              48

(2) INFORMATION FOR SEQ ID NO:58:

(i) SEQUENCE CHARACTERISTICS:
        (A) LENGTH: 53 base pairs
        (B) TYPE: nucleic acid
        (C) STRANDEDNESS: single

```
              (D) TOPOLOGY: linear (ii) MOLECULE TYPE: DNA (xi) SEQUENCE DESCRIPTION: SEQ ID NO:58:

ACTTCGAAAT TAATACGACT CACTATAGGG ACCGACGTCG ACTATCCATG AAG                    53

(2) INFORMATION FOR SEQ ID NO:59:

(i) SEQUENCE CHARACTERISTICS:
              (A) LENGTH: 53 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:59:

ACTTCGAAAT TAATACGACT CACTATAGGG AGCACTCTCC AGCCTCTCAC CGA                    53
```